(12) United States Patent
Theodorescu et al.

(10) Patent No.: US 10,689,392 B2
(45) Date of Patent: Jun. 23, 2020

(54) ANTI-CANCER COMPOUNDS TARGETING RAL GTPASES AND METHODS OF USING THE SAME

(71) Applicant: The Regents of the University of Colorado, a body corporate, Denver, CO (US)

(72) Inventors: Dan Theodorescu, Englewood, CO (US); Michael Fitzpatrick Wempe, Aurora, CO (US); David Ross, Niwot, CO (US); Samy Meroueh, Westfield, IN (US); Martin A. Schwartz, Earlysville, VA (US); Phillip Reigan, Denver, CO (US)

(73) Assignees: THE REGENTS OF THE UNIVERSITY OF COLORADO, A BODY CORPORATE, Denver, CO (US); INDIANA UNIVERSITY RESEARCH AND TECHNOLOGY CORPORATION, Indianapolis, IN (US); UNIVERSITY OF VIRGINIA PATENT FOUNDATION, Charlottesville, VA (US)

(*) Notice: Subject to any disclaimer, the term of this patent is extended or adjusted under 35 U.S.C. 154(b) by 0 days.

(21) Appl. No.: 15/142,011

(22) Filed: Apr. 29, 2016

(65) Prior Publication Data
US 2016/0280715 A1 Sep. 29, 2016

Related U.S. Application Data

(63) Continuation of application No. 14/366,035, filed as application No. PCT/US2012/071341 on Dec. 21, 2012, now Pat. No. 9,353,121.

(60) Provisional application No. 61/578,869, filed on Dec. 21, 2011.

(51) Int. Cl.
| C07D 491/052 | (2006.01) |
| A61K 31/4162 | (2006.01) |
| A61K 31/351 | (2006.01) |
| A61K 31/437 | (2006.01) |
| A61K 31/505 | (2006.01) |
| A61K 31/5513 | (2006.01) |
| A61K 45/06 | (2006.01) |

(52) U.S. Cl.
CPC ........ *C07D 491/052* (2013.01); *A61K 31/351* (2013.01); *A61K 31/4162* (2013.01); *A61K 31/437* (2013.01); *A61K 31/505* (2013.01); *A61K 31/5513* (2013.01); *A61K 45/06* (2013.01)

(58) Field of Classification Search
None
See application file for complete search history.

(56) References Cited

U.S. PATENT DOCUMENTS

| 4,555,396 | A | 11/1985 | Frank et al. |
| 5,750,550 | A * | 5/1998 | Eissenstat ............... C07C 69/38 514/373 |
| 6,143,471 | A | 11/2000 | Takata et al. |
| 8,642,660 | B2 | 2/2014 | Goldfarb |
| 9,353,121 | B2 | 5/2016 | Theodorescu et al. |
| 2007/0105105 | A1 | 5/2007 | Clelland et al. |
| 2007/0105114 | A1 | 5/2007 | Li et al. |
| 2007/0155766 | A1 | 7/2007 | Zheng et al. |
| 2009/0163545 | A1 | 6/2009 | Goldfarb |
| 2009/0221559 | A1 | 9/2009 | Bonfanti et al. |
| 2009/0221568 | A1 | 9/2009 | Shaw et al. |
| 2011/0003298 | A1 | 1/2011 | Liew |
| 2011/0257184 | A1 | 10/2011 | Qu et al. |
| 2012/0214824 | A1 | 8/2012 | Tait et al. |
| 2012/0252792 | A1 | 10/2012 | Neubig et al. |

FOREIGN PATENT DOCUMENTS

| CN | 103910737 | 7/2014 | |
| JP | H10-279480 | 10/1998 | |
| JP | 2007507204 A | 3/2007 | |
| WO | 2005012875 A2 | 2/2005 | |
| WO | WO 2006/126625 | * 5/2006 | ......... A61K 31/4152 |
| WO | WO 2007/081966 | 7/2007 | |
| WO | WO 2008/143894 | 11/2008 | |
| WO | WO 2011/010715 | 1/2011 | |
| WO | WO 2013/096852 | 6/2013 | |
| WO | WO 2013/152313 | 10/2013 | |
| WO | WO 2013/182472 | 12/2013 | |

OTHER PUBLICATIONS

Shi, Daqing. Three-Component One-Pot Synthesis of 1,4-Dihydropyrano[2,3-c]pyrazole Derivatives in Aqueous Media. Synthetic Communications. 34(24), 2004, 4557-4563.*
Dawane, B.S. One-pot multicomponent synthesis and antimicrobial evaluation of some novel pyrano-[2,3-c]-pyrazoles derivatives. Der Pharma Chemica, 2011, 3(3): 300-305.*
Abdelrazek, Fathy M. Synthesis and Molluscicidal Activity of Some 1,3,4-Triaryl-5-chloropyrazole, Pyrano[2,3-c]pyrazole, Pyrazolylphthalazine and Pyrano[2,3-d]thiazole Derivatives. Arch. Pharm. Chem. LifeSci. 2006, 339, 305-312.*
Database Registry Chemical Abstracts Service, Columbus, Ohio, Accession No. RN 2749-59-9, Entered STN: Nov. 16, 1984.*
Database Registry Chemical Abstracts Service, Columbus, Ohio, Accession No. RN 361185-42-4, Entered STN: Oct. 9, 2001.*
Ito, Nobuyuki. Cancer Science 94(1), (2003) 3-8.*
DeWald, H. A. Pyrazolodiazepines. 3. 4-Aryl-1,6,7,8-tetrahydro-1,3-dialkylpyrazolo[3,4-e][1,4]diazepines as Antidepressant Agents. J. Med. Chem. 1981, 24, 982-987.*
Database Registry Chemical Abstracts Service, Columbus, Ohio, Accession No. RN 362503-73-9, Entered STN: Oct. 16, 2001.*

(Continued)

*Primary Examiner* — Samantha L Shterengarts
(74) *Attorney, Agent, or Firm* — Greenberg Traurig, LLP; Jonathan D. Ball; Evelyn M. Kwon

(57) ABSTRACT

The invention provides methods of inhibiting the growth or metastasis of a cancer in a mammal by inhibiting a Ral GTPase in the mammal. The invention also provides small molecule inhibitors of Ral GTPases useful in the methods of the invention and pharmaceutical compositions containing the therapeutically effective compounds of the invention, and methods of using the same.

9 Claims, 12 Drawing Sheets

(56) References Cited

OTHER PUBLICATIONS

Varga, Laszlo. Solution-Phase Parallel Synthesis of a Pyridinium Pyrazol-3-olate Inner Salt Library Using a Three-Component Reaction. J. Comb. Chem. 2006, 8, 338-343.*
Nakagawa, Hidehiko. Hydroxyl radical scavenging by edaravone derivatives: Efficient scavenging by 3-methyl-1-(pyridin-2-yl)-5-pyrazolone with an intramolecular base. Bioorganic & Medicinal Chemistry Letters 16 (2006) 5939-5942.*
WO 2006126625, English Translation, Jun. 17, 2019.*
"Accession No. RN 53316-58-8," Database Registry, Chemical Abstracts Service, Columbus, Ohio, Nov. 16, 1984, 3 pages.
"Accession No. RN 168429-49-0," Database Registry, Chemical Abstracts Service, Columbus, Ohio, Oct. 5, 1995, 2 pages.
Abdelrazek et al. "Synthesis and Molluscicidal Activity of Some 1,3,4-Triaryl-5-chloropyrazole, Pyrazolylphthalazine and Pyrano[2,3-d]thiazole Derivatives," Arch Pharm Chemistry in Life Sciences, Jun. 2006, vol. 339, No. 6, pp. 305-312.
Al-Matar et al., "Green One Pot Solvent-Free Synthesis of Pyrano[2,3-c]-Pyrazoles and Pyrazolo[1,5-a]Pyrimidines," Molecules, 2010, vol. 15, pp. 6619-6629.
Albadi et al., "CuO—CeO2 nanocomposite: a highly efficient recyclable catalyst for the multicomponent synthesis of 4H-benzo[b]pyran derivatives," Chinese Chemical Letters, 2013, vol. 24, pp. 821-824.
Al-Duaij, "An Eco-friendly Method for Novel Scaffolds: Novel N2-Substituted Fused Pyrazolo (4',3':5,6) Pyrano (2,3-d) Pyrimidine Terminated by Hydroxy Group," J. Chem. Chem. Eng., 2013, vol. 7, pp. 821-828.
Al-Mutairi et al., "Microwave versus ultrasound assisted synthesis of some new heterocycles based on pyrazolone moiety," Journal of Saudi Chemical Society, 2010, vol. 14, pp. 287-299.
Babaie et al., "Nanosized magnesium oxide as a highly effective heterogeneous base catalyst for the rapid synthesis of pyranopyrazoles via a tandem four-component reaction," Arabian Journal of Chemistry, 2011, vol. 4, pp. 159-162.
Balaskar et al., "Greener approach towards the facile synthesis of 1,4-dihydropyrano[2,3-c]pyrazol-5-yl cyanide derivatives at room temperature," Chinese Chemical Letters, 2010, vol. 21, pp. 1175-1179.
Bhosale et al., "One-pot three-component condensation for the synthesis of 1,4-dihydropyrano[2,3-c]pyrazoles using cesium fluoride as an efficient catalyst," J. Chem. Pharm. Res., 2014, vol. 6(4), pp. 733-737.
Chobe et al. "Green approach towards synthesis of substituted pyrazole-1,4-dihydro,9-oxa,1,2,6,8-tetrazacyclopentano[b]naphthalene-5-one derivatives as antimycobacterial agents," Medicinal Chemistry Research, Feb. 2013, vol. 22, No. 11, pp. 5197-5203.
Dilthey et al. "Die Reäktionsfahigkeit [alfpha]-und[gamma]-ständiger Methylgruppen in Pyryliumsalzen. (Uber Pyryliumverbindungen, XIII.)," Berichte Der Deutschen Chemischen Gesellschaft, Jan. 1924, pp. 1653-1656.
Elinson et al., "Solvent-free and 'on-water' multicomponent assembling of aldehydes, 3-methyl-2-pyrazoline-5-one, and malononitrile: fast and efficient approach to medicinally relevant pyrano[2,3-c]pyrazole scaffold,", American Chemical Society, 2015, 35 pages.
Eskandari et al., "Novel silica sodium carbonate (SSC): Preparation, characterization and its first catalytic application to the synthesis of new dihydropyrano[2,3-c]pyrazoles," Catalysis Communications, 2014, vol. 54, pp. 124-130.
Farahi et al., "An environmentally friendly synthesis of 1,4-dihydropyrano[2,3-c]pyrazole derivatives catalyzed by tungstate sulfuric acid," Chinese Chemical Letters, 2014, vol. 25, pp. 1580-1582.
Gujar et al., "Molecular sieves: an efficient and reusable catalyst for multi-component synthesis of dihydropyrano[2,3-C]pyrazole derivatives," Tetrahedron Letters, 2014, vol. 55, pp. 6030-6033.
Guo et al., "D,L-Proline-Catalyzed One-Pot Synthesis of Pyrans and Pyrano[2,3-c]pyrazole Derivatives by a Grinding Method under Solvent-Free Conditions," Synthetic Communications: An International Journal for Rapid Communication of Synthetic Organic Chemistry, 2007, vol. 37, pp. 2111-2120.
Hafiz et al., "Synthesis of New Substituted 1,3-Diphenyl-5-chloropyrazoles," J. Chem. Res. (S), 1998, pp. 690-691.
Hamad et al. "Distinct requirements for Ras oncogenesis in human versus mouse cells," Genes & Development, Aug. 2002, vol. 16, No. 16, pp. 2045-2057.
Hasaninejad et al., "Silica bonded n-propyl-4-aza-1-azoniabicyclo[2.2.2]octane chloride (SB-DABCO): A highly efficient, reusable and new heterogeneous catalyst for the synthesis of 4H-benzo[b]pyran derivatives," Applied Catalysis A: General, 402, 2011, pp. 11-22.
Ilovaisky et al., "Green Approach to the Design of Functionalized Medicinally Privileged 4-Aryl-1,4-dihydropyrano[2,3-c]-pyrazole-5-carbonitrile Scaffold," J. Heterocyclic Chem., 2014, vol. 51, pp. 523-526.
Jin et al., "A Clean and Simple Synthesis of 6-Amino-4-Aryl-5-Cyano-3-Methyl-in Water," Synthetic Communications: An International Journal for Rapid Communication of Synthetic Organic Chemistry, 2005, vol. 35, pp. 137-143.
Kangani et al., "Green synthesis of 1,4-dihydropyrano[2,3-c]pyrazole derivatives using maltose as biodegradable catalyst," Res Chem Intermed, 2015, vol. 41, pp. 2513-2519.
Karimi-Jaberi et al., "Trichloroacetic acid as a solid heterogeneous catalyst for the rapid synthesis of dihydropyrano[2,3-c]pyrazoles under solvent free conditions," Heterocycl. Commun., 2011, vol. 17(5-6), pp. 177-179.
Khoobi et al., "New tetracyclic tacrine analogs containing pyrano[2,3-c]pyrazole: Efficient Synthesis, biological assessment and docking simulation study," American Chemical Society, 2015, 15 pages.
Khurana et al., "Rapid Synthesis of Polyfunctionalized Pyrano[2,3-c]pyrazoles via Multicomponent Condensation in Room-Temperature Ionic Liquids," Synthetic Communications: An International Journal for Rapid Communication of Synthetic Organic Chemistry, 2011, vol. 41, pp. 405-410.
Kiyani et al., "One-pot, four-component synthesis of pyrano [2,3-c]pyrazoles catalyzed by sodium benzoate in aqueous medium," Current Chemistry Letters, 2013, vol. 2, pp. 197-206.
Kshirsagar et al., "Mg—Al Hydrotalcite as a First Heterogeneous Basic Catalyst for the Synthesis of 4H-Pyrano [2,3-c]pyrazoles Through a Four-Component Reaction," Synthetic Communications: An International Journal for Rapid Communication of Synthetic Organic Chemistry, 2011, vol. 41, pp. 1320-1325.
Lehmann et al., "Three-Component Combinatorial Synthesis of Novel Dihydropyrano[2,3-c]pyrazoles", J. Comb. Chem., 2008, vol. 10, pp. 364-367.
Lim et al. "Activation of RalA is critical for Ras-induced tumorigenesis of human cells," Cancer Cell, Jun. 2005, vol. 7, pp. 533-545.
Makawana et al. "Microwave assisted synthesis and antimicrobial evaluation of new fused pyran derivatives bearing 2-morpholinoquinoline nucleus," bioorganic & Medicinal Chemistry Letters, Jul. 2011, vol. 21, No. 20, pp. 6166-6169.
Mamaghani et al., An efficient and eco-friendly synthesis and evaluation of antibactrial activity of pyrano[2,3-c]pyrazole derivatives, Med Chem Res, Sep. 25, 2014, 11 pages.
Mohamed et al., "Facile synthesis of fused nitrogen containing heterocycles as anticancer agents," Der Pharma Chemica, 2010, vol. 2(1), pp. 400-417.
Muramulla et al., "A new catalytic mode of the modularly designed organocatalysts (MDOs): enantioselective synthesis of dihydropyrano[2,3-c]pyrazoles," Tetrahedron Letters, 2011, vol. 52, pp. 3905-3908.
Paul et al., "Uncapped SnO2 quantum dot catalyzed cascade assembling of four components: a rapid and green approach to the pyrano[2,3-c]pyrazole and spiro-2-oxindole derivatives," Tetrahedron, 2014, vol. 70, pp. 6088-6099.
Pavlova et al., "Synthesis and cytotoxic activity of heterocyclization products of 1,1-dicyano-2-hetaryl-2-trifluoromethylethylenes," Russian Chem. Bulletin, Int'l Edition, Jan. 2010, vol. 59(1), pp. 162-176.
Reddy et al., "Glycine-Catalyzed Efficient Synthesis of Pyranopyrazoles via One-Pot Multicomponent Reaction," Synthetic Communications: An International Journal for Rapid Communication of Synthetic Organic Chemistry, 2010, vol. 40(19), pp. 2930-2934.

(56) References Cited

OTHER PUBLICATIONS

Ren et al., "Solvent-Free, One-Pot Synthesis of Pyrano[2,3-c]pyrazole Derivatives in the Presence of KF•2H20 by Grinding," Synthetic Communications: An International Journal for Rapid Communication of Synthetic Organic Chemistry, 2005, vol. 35(19), pp. 2509-2513.
Saad et al. "Synthesis of New Substituted 1, 3-Diphenyl-5-chloropyrazoles," Journal of Chemical Research, Jan. 1998, pp. 2946-2957.
Sheibani et al., "Three-Component Reaction to Form 1,4-Dihydropyrano[2,3-c]pyrazol-5-yl Cyanides," Synthetic Communications: An International Journal for Rapid Communication of Synthetic Organic Chemistry, 2009, vol. 40(2), pp. 257-265.
Shi et al., "Three-Component One-Pot Synthesis of 1,4-Dihydropyrano[2,3-c]pyrazole Derivatives in Aqueous Media," Synthetic Communications: An International Journal for Rapid Communication of Synthetic Organic Chemistry, 2004, vol. 34(24), pp. 4557-4563.
Smith et al. "The Metastasis-Associated Gene CD24 Is Regulated by Ral GTPase and Is a Mediator of Cell Proliferation and Survival in Human Cancer," Cancer Research, Feb. 15, 2006, vol. 66, No. 4, pp. 1917-1922.
Sohal et al., "Glycerol mediated, one-pot, multicomponent synthesis of dihydroppyrano[2,3-c]pyrazoles," European J. Chem., 2013, vol. 4(4), pp. 450-453.
Sohal et al., "Catalyst free, one-pot, facile synthesis of novel pyrazolo-1,4-dihydropyridine derivative form pyranopyrazoles," European J. Chem., 2014, vol. 5(2), pp. 227-232.
Tamaddon et al., "A four-component synthesis of dihydropyrano[2,3-c]pyrazoles in a new water-based worm-like micellar medium," Tetrahedron Letters, 2014, vol. 55, pp. 3588-3591.
Yan et al. "Discovery and characterization of small molecules that target the GTPase Ral," Nature, Nov. 20, 2014, vol. 515, No. 7527, pp. 443-447.
Yang et al., Synthesis and bioactivity of lignin related high-added-value 2H,4H-dihydro-pyrano[2,3-c]pyrazoles and 1H,4H-dihydro-pyrano[2,3-c]pyrazoles, Industrial Crops and Products, 2014, vol. 52, pp. 413-419.
International Search Report and Written Opinion for International Patent Application No. PCT/US2012/071341, dated Mar. 14, 2013, 7 pages.
International Report on Patentability for International Patent Application No. PCT/US2012/071341, dated Jul. 3, 2014, 6 pages.
Official Action (English translation) for Chinese Patent Application No. 201280070263.9, dated Sep. 16, 2015, 8 pages.
Official Action (English translation) for Chinese Patent Application No. 201280070263.9, dated Jun. 7, 2016, 6 pages.
Extended Search Report for European Patent Application No. 12859252.4, dated Apr. 16, 2015 8 pages.
International Search Report and Written Opinion for International Patent Application No. PCT/US15/40021, dated Oct. 7, 2015, 7 pages.
Official Action for U.S. Appl. No. 14/366,035, dated Feb. 12, 2015, 27 pages.
Official Action for U.S. Appl. No. 14/366,035, dated Jul. 28, 2015, 9 pages.
Notice of Allowance for U.S. Appl. No. 14/366,035, dated Feb. 1, 2016, 7 pages.
U.S. Appl. No. 15/324,629, filed Jan. 6, 2017, Theodorescu.
Neel et al., "The RalGEF-Ral Effector Signaling Network: The Road Less Traveled for Anti-Ras Drug Discovery," Genes & Cancer. 2011, vol. 2(3), pp. 275-287.
Otto, "Darstellung einiger 4H-Pyrano[2.3-c]pyrazolderiyate," Archiv der Pharmazie, 1974, pp. 444-447.
Tacconi et al., "A New Route to 4H-Pyrano[2,3-c] Pyrazoles," Journal of Drakt. Chemie., 1980, pp. 831-834.
Official Action for Australia Patent Application No. 2012358317, dated Dec. 2, 2016 5 pages.
Notice of Allowance for Australia Patent Application No. 2012358317, dated Dec. 4, 2017 3 pages.

English Translation of Official Action for China Patent Application No. 201280070263.9, dated Dec. 27, 2016 5 pages.
Notice of Allowance (with English translation) for Chinese Patent Application No. 201280070263.9, dated Sep. 22 2017.
Official Action for European Patent Application No. 12859252.4, dated Mar. 10, 2017 8 pages.
Official Action with English Translation for Japan Patent Application No. 2014-548963, dated Mar. 7, 2017 6 pages.
Official Action for Canadian Patent Application No. 2954560, dated Nov. 22, 2017 4 pages.
International Preliminary Report on Patentability for International (PCT) Patent Application No. PCT/US2015/040021, dated Jan. 19, 2017 6 pages.
Extended Search Report for European Patent Application No. 15819681.6, dated Nov. 28, 2017 11 pages.
Official Action for U.S. Appl. No. 15/324,629 dated Oct, 12, 2017 7 pages, Restriction Requirement.
Official Action for U.S. Appl. No. 15/324,629 dated Jan. 8, 2018 8 pages.
Intention to Grant for European Patent Application No. 12859252.4, dated Jan. 23, 2018 5 pages.
Official Action (with English Translation) for Japanese Patent Application No. 2014-548963, dated Jan. 30, 2018 3 pages.
Official Action (with English translation) for Korean Patent Application No. 10-2017-7002960 dated Mar. 28 2018 8 pages.
U.S. Appl. No. 16/241,587, filed Jan. 7, 2019, Theodorescu et al.
Selim et al., "Activated Nitrites in Heterocyclic Synthesis: Synthesis of Pyrano[2,3-C] Pyrazole Derivatives," Oriental Journal of Chemistry, vol. 10, No. 3, 1994, pp. 199-204, abstract only.
Ramtekkar et al., "Computer-Aided Drug Design of Pyranopyrazoles and Related Compounds for Checkpoint Kinase-1," Letter in Drug Design & Discovery, vol. 6, 2006, pp. 579-584.
Official Action for Canadian Patent Application No. 2859985, dated Oct. 11, 2018, 6 pages.
Official Action (with English translation) for Korean Patent Application No. 10-2017-7002960 dated Nov. 28, 2018 12 pages.
Official Action (with English translation) for Japanese Patent Application No. 2014-548963, dated Jul. 17, 2018, 6 pages.
Notice of Allowance for U.S. Appl. No. 15/324,629 dated Sep. 17, 2018 9 pages.
Notice of Preliminary Rejection in corresponding Korean Patent Application No. 10-2014-7020271, dated May 28, 2019 (7 pages).
Canadian Office Action in corresponding Canadian Patent Application No. 2,859,985, dated Oct. 11, 2018 (6 pages).
Interview Record in corresponding Canadian Patent Application No. 2,859,985, dated Apr. 10, 2019 regarding reference D14.
Reference D14—Compounds from SciFinder in corresponding Canadian Patent Application No. 2,859,985.
Chien, et al., "RAL GTPases are linchpin modulators of human tumor-cell proliferation and survival," EMBO Reports, vol. 4, No. 8, pp. 801-806 (2003).
Dawane, et al., "One-pot multicomponent synthesis and antimicrobial evaluation of some novel pyrano-[2,3-c]-pyrazoles derivatives," Scholars Research Library, vol. 3(3), pp. 302-305 (2011).
Yu, et al., "Identification of Small Molecular Weight Inhibitors of Src Homology 2 Domain-Containing Tyrosine Phosphatase 2 (SHP-2) via in Silico Database Screening Combined with Experimental Assay," J. Med. Chem, vol. 51, pp. 7396-7404 (2008).
"Accession No. RN 309920-83-0," Database Registry, Chemical Abstracts Service, Columbus Ohio, Entered STN: Dec. 20, 2000.
"Accession No. RN 311326-67-7," Database Registry, Chemical Abstracts Service, Columbus Ohio, Entered STN: Dec. 27, 2000.
International Search Report in corresponding PCT Patent Application No. PCT/US15/40021, dated Oct. 7, 2015 (2 pages).
Search Report with English translation and search strategy in corresponding Japanese Patent Application No. 2017-500822, dated Mar. 7, 2019 (20 pages), identifying JP 2007507204 which claims the benefit of PCT/US2004/024424 (WO 2005/012875).
English translation of Office Action in corresponding Japanese Patent Application No. 2017-500822, dated Oct. 15, 2019 (15 pages).

(56) References Cited

OTHER PUBLICATIONS

"Accession No. RN 168429-51-4," Database Registry, Chemical Abstracts Service, Columbus Ohio, Entered STN: Oct. 5, 1995, p. 1, in Interview Record (CA 2,859,985).
"Accession No. RN 168429-53-6," Database Registry, Chemical Abstracts Service, Columbus Ohio, Entered STN: Oct. 5, 1995, p. 1, in Interview Record (CA 2,859,985).
Interview Record in corresponding Canadian Patent Application No. 2,859,985, held Jan. 2, 2020 (1 page).
Office Action in corresponding Canadian Patent Application No. 2,859,985, dated Nov. 25, 2019 (4 pages).

* cited by examiner

ANTI-CANCER COMPOUNDS TARGETING RAL GTPASES AND METHODS OF USING THE SAME

CROSS REFERENCE TO RELATED APPLICATION

The present application is a continuation of U.S. patent application Ser. No. 14/366,035, filed Jun. 17, 2014, which is a national stage application under 35 U.S.C. 371 of PCT Application No. PCT/US2012/071341 having an international filing date of Dec. 21, 2012, which designated the United States, which PCT application claimed the benefit of U.S. Application Ser. No. 61/578,869, filed Dec. 21, 2011. These applications are incorporated herein by reference in their entirety.

GOVERNMENT INTEREST

This invention was made with Government support under grant numbers CA075115, CA104106 and CA143971 awarded by the National Institutes of Health. The U.S. Government has certain rights in the invention.

TECHNICAL FIELD

The invention relates to therapeutic compounds, pharmaceutical compositions containing the same and their use in the prevention or treatment of cancer.

BACKGROUND OF INVENTION

Ras is mutated in cancer more frequently than any other oncogene. Hence, Ras has been a focus for the development of rationally designed anti-cancer drugs, yet to date none have been successfully developed. In 1989, several groups showed that posttranslational modification of Ras proteins by farnesyl lipids is essential for Ras membrane association and transformation. Farnesyltransferase (FTase) was then purified and characterized and shortly thereafter, a second prenyltransferase, geranylgeranyltransferase type I (GGTase-I), that modifies Ras with a geranylgeranyl lipid was discovered. GGTase-I inhibitors (GGTIs) were studied and at least one such inhibitor, GGTI-2417, has been shown to inhibit the in vitro growth and survival of the MiaPaCa2 pancreatic cell line. But, these inhibitory effects were modest and no clinical trials with GGTIs have followed.

RalA and RalB are paralogs in the family of Ras monomeric G proteins that have approximately 85% amino acid identity, and play a role in the regulation of endocytosis, exocytosis, actin cytoskeletal dynamics, and transcription. Like Ras, Ral proteins have also been implicated in tumorigenesis and metastasis. Ral GTPases may be activated in a Ras-dependent manner, via several guanidine nucleotide exchange factors, including RalGDS. Activation of the Ral pathway has been shown to be a requirement for transformation of human cells (Rangaraj an A, Hong S J, Gifford A, Weinberg R A. *Species-and cell type-specific requirements for cellular transformation*. Cancer Cell 2004; 6:171-83; Hamad N M, Elconin J H, Karnoub A E, et al. *Distinct requirements for Ras oncogenesis in human versus mouse cells*. Genes Dev 2002; 16:2045-57), and Ras-mediated transformation depends on activation of RalA (Lim K H, Baines A T, Fiordalisi J J, et al. *Activation of RalA is critical for Ras-induced tumorigenesis of human cells*. Cancer Cell 2005; 7:533-45). RalA and RalB also play a role in the transcriptional regulation of CD24, a metastasis-associated gene in bladder and other cancers (Smith S C, Oxford G, Wu Z, et al. *The metastasis associated gene CD24 is regulated by Ral GTPase and is a mediator of cell proliferation and survival in human cancer*. Cancer Res 2006; 66:1917-22).

Thus, Ral GTPases present a compelling therapeutic target for the prevention and treatment of solid tumors and the metastasis of these cancers, and there exists a need for effective methods of inhibiting Ral GTPases for the treatment and prevention of cancer.

SUMMARY OF INVENTION

The present invention provides molecules that can inhibit Ral GTPases, as well as therapeutic uses of these molecules to prevent or slow the growth and metastasis of cancer in a mammal.

The present inventors have used novel computational algorithms to identify a pocket in the RalA protein crystal structure that is located far from the nucleotide binding site and that is present in the GDP (inactive) but not GTP (active) conformation of the protein. A threaded 3D model of RalB based on that of RalA (RalB has not been crystalized) was used to show that this pocket was common to both RalA and RalB paralogs such that small molecule binding to this allosteric site traps RalA or RalB in their inactive conformation. Computational screening of 500,000 chemical entities identified 88 high stringency candidates that dock into this pocket.

An unbiased screen with the GDP loaded RalB protein using a 92,167-member encoded bead based combinatorial library identified 11 compounds that bound to inactive RalB. Computational determination of putative docking sites of these compounds yielded a single site, present in both Ral paralogs, identical to the pocket found by computational screening using the RalA structure.

Hence, these two complementary approaches used by the present inventors identified a similar target site, present in both paralogs, that is distinct from the nucleotide binding pocket in these proteins. These analyses identified Ral GTPase inhibitors that disrupt Ral protein binding with Ral-associated proteins exo84, sec5 and RalBP1. The identified Ral GTPase inhibitors can be used to block the associated conformational change of RalA upon GTP binding, thus preventing effector engagement and downstream signaling. These inhibitors bind in Ral protein pockets located away from the nucleotide binding cavity that is located in the active site of the enzyme. Additionally, other Ral binding proteins that bind with Ral through other binding sites on the Ral protein, including proteins such as filamin A, PLD1 and ZONAB, may be prevented from binding with Ral in the presence of the identified inhibitor compounds of this invention.

Compounds were evaluated in vitro for their efficacy in inhibiting the growth of human cancer cells, and particularly, cancers of the bladder, pancreas, prostate, colon, skin and lung, leading to the therapeutic methods of the present invention.

Thus, the present invention provides compounds that can inhibit Ral GTPases. The invention also provides pharmaceutical compositions containing these compounds. The invention also provides methods of using these compounds and pharmaceutical compositions to treat or prevent cancer.

One embodiment is a compound of the invention having Ral GTPase inhibitory activity and having the following chemical structure (Formula 1):

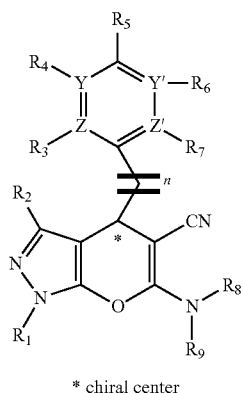

* chiral center 6-amino-1,3-disubstituted-4-phenyl-1,4-dihydropyrano[2,3-c]pyrazole-5-carbonitriles and pharmaceutically acceptable enantiomers, diastereomers, racemates, and salts thereof, wherein:
n=0-5
X, Y, Y', Z and Z' are individually selected from C, N, or N-oxide;
$R_1$-$R_9$ are independently (including when X, Y or Z are C) selected from hydrogen, halogen, —OH, —O—$R_{10}$, $C_1$-$C_{24}$ alkyl, $C_3$-$C_{24}$ alkenyl, $C_4$-$C_{24}$ dienyl, $C_6$-$C_{24}$ trienyl, $C_8$-$C_{24}$ tetraenyl, $C_6$-$C_{18}$ aryl, substituted $C_6$-$C_{18}$ aryl, $C_1$-$C_{14}$-alkoxy, carboxy, cyano, $C_1$-$C_{14}$ alkanoyloxy, alkylthio, alkylsulfonyl, $C_2$-$C_{14}$ alkoxycarbonyl, $C_2$-$C_{14}$ alkanoylamino, S—$R_{10}$, —$SO_2$—$R_{10}$, —$NHSO_2R_{10}$ and —$NHCO_2R_{10}$; and,
$R_{10}$ is phenyl or naphthyl, optionally substituted with one to three groups selected from $C_1$-$C_6$ alkyl, $C_6$-$C_{10}$ aryl, $C_1$-$C_6$ alkoxy, halogen, and $C_4$-$C_{20}$ hydroxyheteroaryl, wherein the heteroatoms are selected from the group consisting of sulfur, nitrogen, and oxygen.

Another embodiment is a compound of the invention having Ral GTPase inhibitory activity and having the structure:

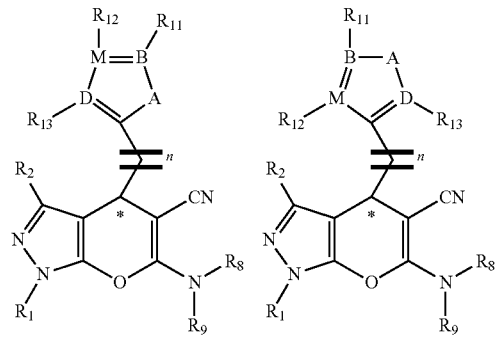

* chiral center    * chiral center and pharmaceutically acceptable enantiomers, diastereomers, racemates, and salts thereof, wherein:
n=0-5;
A, B, M, and D are individually selected from C, N, or N-oxide;

$R_1$, $R_2$, $R_8$, $R_9$, $R_{11}$, $R_{12}$, $R_{13}$ are independently (including when B, M or D are carbon) selected from hydrogen, halogen, —OH, —O—$R_{14}$, $C_1$-$C_{24}$ alkyl, $C_3$-$C_{24}$ alkenyl, $C_4$-$C_{24}$ dienyl, $C_6$-$C_{24}$ trienyl, $C_8$-$C_{24}$ tetraenyl, $C_6$-$C_{18}$ aryl, substituted $C_6$-$C_{18}$ aryl, $C_1$-$C_{14}$-alkoxy, carboxy, cyano, $C_1$-$C_{14}$ alkanoyloxy, $C_1$-$C_{14}$ alkylthio, $C_1$-$C_{14}$ alkylsulfonyl, $C_2$-$C_{14}$ alkoxycarbonyl, $C_2$-$C_{14}$ alkanoylamino, S—$R_{14}$, —$SO_2$—$R_{12}$, —$NHSO_2R_{14}$ and —$NHCO_2R_{14}$; and,
$R_{14}$ is phenyl or naphthyl substituted with one to three groups selected from $C_1$-$C_6$-alkyl, $C_6$-$C_{10}$ aryl, $C_1$-$C_6$ alkoxy and halogen, and $C_4$-$C_{20}$ hydroxyheteroaryl wherein the heteroatoms are selected from the sulfur, nitrogen, and oxygen.

Another embodiment is a compound of the invention having Ral GTPase inhibitory activity and having a structure selected from:

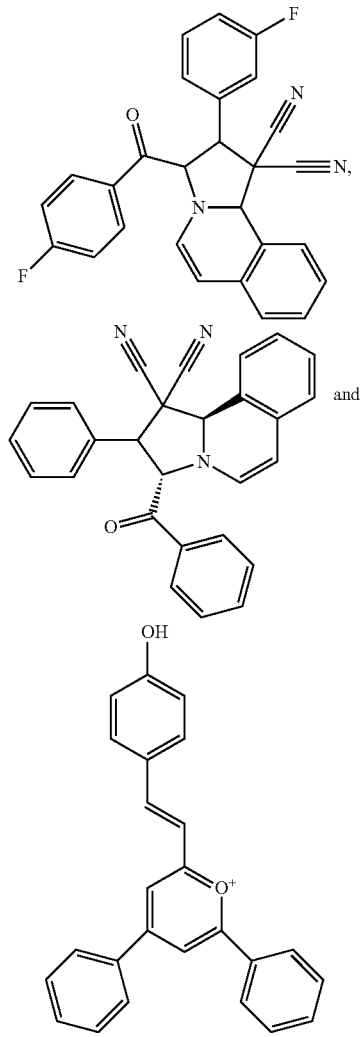

and pharmaceutically acceptable enantiomers, diastereomers, racemates, and salts thereof.

One embodiment of the invention is a method of treating a cancer by administering to a mammal in need of such treatment, a therapeutically-effective amount of a compound that inhibits Ral GTPase enzymatic activity. In one aspect of this embodiment, the compound inhibits at least one paralog of Ral GTPAse (either RalA or RalB), thereby inhibiting the growth or metastasis of a cancer. In a preferred aspect of this embodiment, the compound inhibits both RalA and RalB paralogs. In another aspect of this embodiment, the compound is at least one of the compounds of the invention that also include any one of the chemical structures:

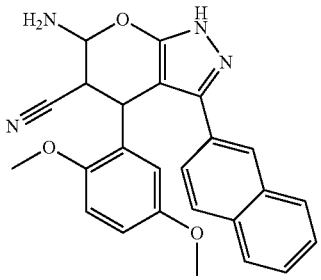 [SMILES: COc1ccc(OC)c(C2c3c(-c4ccc5ccccc5c4)n[nH]c3OC(N)C2C#N)c1]

RBC8 (6-amino-4-(2,5-dimethoxyphenyl)-3-(naphthalen-2-yl)-1,4-dihydropyrano[2,3-c]pyrazole-5-carbonitrile);

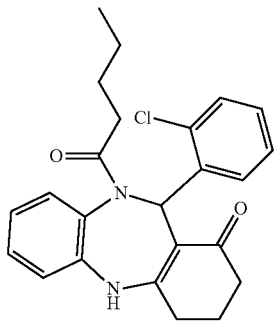 [SMILES: CCCCC(=O)N1c2ccccc2NC2=C(C(=O)CCC2)C1c1ccccc1Cl]

RBC 10 (11-(2-chlorophenyl)-10-pentanoyl-2,3,4,5,10,11-hexahydro-1H-dibenzo[b,e][1,4]diazepin-1-one);

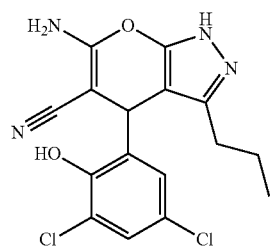 [SMILES: CCCc1n[nH]c2c1C(c1cc(Cl)cc(Cl)c1O)C(C#N)=C(N)O2]

RBC6 (6-amino-4-(3,5-dichloro-2-hydroxyphenyl)-3-propyl-1,4-dihydropyrano[2,3-c]pyrazole-5-carbonitrile);

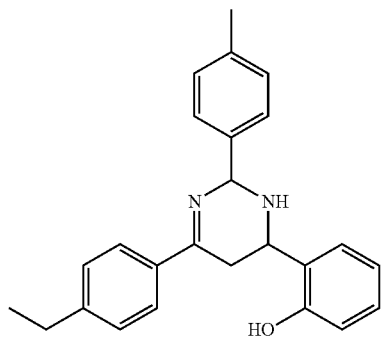 [SMILES: CCc1ccc(C2=NC(c3ccc(C)cc3)NC(c3ccccc3O)C2)cc1]

RBC84 (2-(6-(4-ethylphenyl)-2-p-tolyl-2,3,4,5-tetrahydropyrimidin-4-yl)phenol); and,

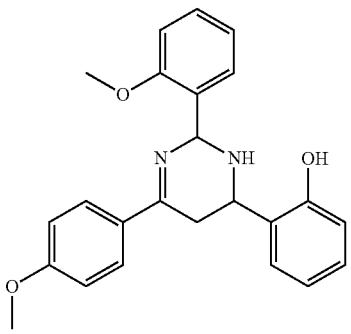 [SMILES: COc1ccc(C2=NC(c3ccccc3OC)NC(c3ccccc3O)C2)cc1]

RBC83 (2-(2-(2-methoxyphenyl)-6-(4-methoxyphenyl)-2,3,4,5-tetrahydropyrimidin-4-yl)phenol), and pharmaceutically acceptable enantiomers, diastereomers, racemates, and salts thereof.

In a specific embodiment of these methods of treating or preventing a cancer in a mammal, the compound is administered to the mammal within a pharmaceutical composition of the invention.

Thus, another aspect of the invention is a pharmaceutical composition containing one or more of the compounds of the invention with at least one pharmaceutically-acceptable carrier.

Another embodiment of the invention is a method of preventing or treating metastatic cancers, particularly metastatic pancreas, prostate, lung, bladder, skin and/or colon cancers, by administering a therapeutically effective amount of at least one compound of the invention to a mammal in need of such treatment or suspected of having a cancer or a metastasis of a cancer.

Another embodiment of the invention is a method of treating cancer by administering a therapeutically effective combination of at least one of the compounds of the invention and one or more other known anti-cancer or anti-inflammatory treatments. For example, other anti-cancer treatments may include prenyltransferase inhibitors, including geranylgeranyltransferase type I (GGTase-I) inhibitors, surgery, chemotherapy, radiation, immunotherapy, or combinations thereof.

Also provided herein are methods for the prevention, treatment or prophylaxis of cancer in a mammal comprising administering to a mammal in need thereof, therapeutically-effective amounts of any of the pharmaceutical compositions of the invention.

Also provided herein are methods for preventing the metastasis of a cancer in a mammal comprising administering to the mammal, therapeutically-effective amounts of at least one compound of the invention, including, for example, pharmaceutical compositions containing at least one compound of the invention.

Also provided herein are pharmaceutical packages comprising therapeutically-effective amounts of at least one compound of the invention within a pharmaceutical composition. The pharmaceutical compositions may be administered separately, simultaneously or sequentially with other compounds or therapies used in the prevention, treatment or amelioration of cancer in a mammal. These packages may also include prescribing information and/or a container. If present, the prescribing information may describe the administration, and/or use of these pharmaceutical compositions alone or in combination with other therapies used in the prevention, treatment or amelioration of cancer in a mammal.

Another embodiment of this invention is a method of testing the susceptibility of a mammal having lung cancer to treatment with a putative inhibitor of Ral GTPase activity by testing the mammal for a response to administration of the putative inhibitor indicative of growth inhibition or reduction in cancer cell number or tumor volume in the mammal.

Other aspects of the invention will be set forth in the accompanying description of embodiments, which follows and will be apparent from the description or may be learned by the practice of the invention. However, it should be understood that the following description of embodiments is given by way of illustration only since various changes and modifications within the spirit and scope of the invention will become apparent to those skilled in the art and are encompassed within the scope of this invention.

DESCRIPTION OF EMBODIMENTS

Figure 1:
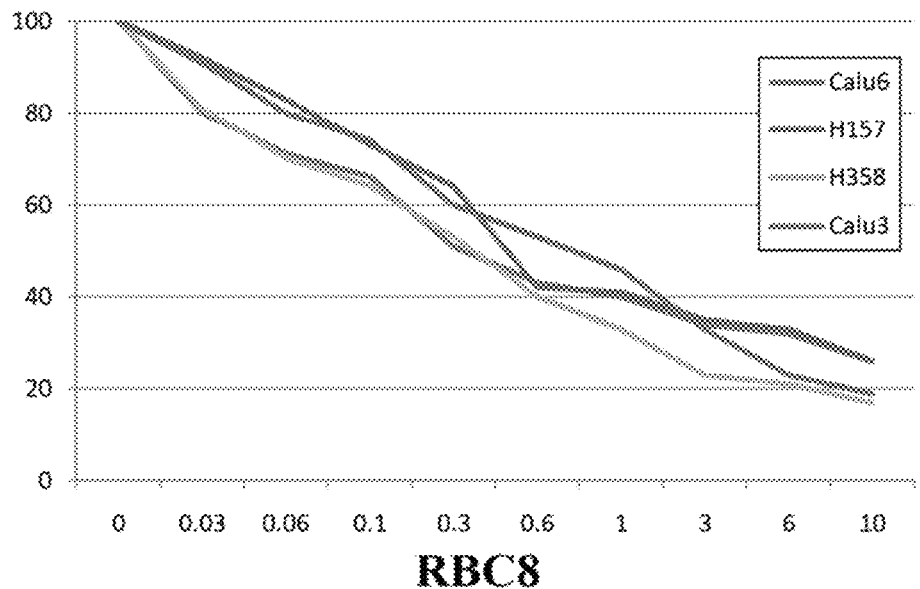
FIG. 1 shows the dose-inhibition activity of two compounds of the invention, RBC8 and RBC10, on growth of human lung cancer cell lines.
Figure 1:
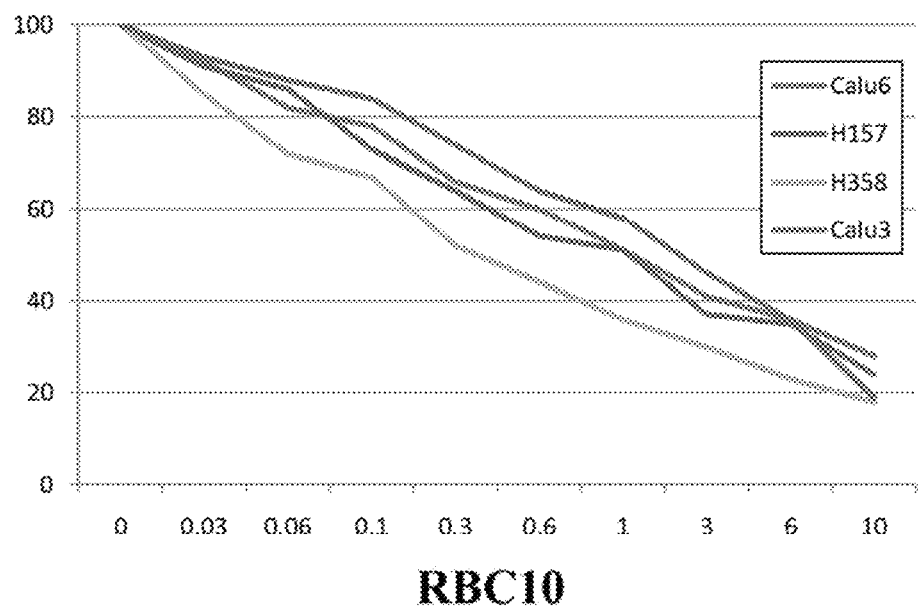

Based on their compelling clinical significance in tumor establishment and metastasis, the present inventors have identified and used Ral GTPases as molecular targets. As with all GTPases, activity of Ral is dependent upon cycling between an inactive (GDP-bound) and an active (GTP-bound) conformation. Active Ral proteins mediate downstream processes through their own set of effectors, including Ral Binding Protein 1 (RalBP1, RLIP76 or RIP1(37)), Sec5/Exo85, filamin, and phospholipase Dl. Thus, compounds that bind Ral-GDP and not Ral-GTP may be used to sterically inhibit effector binding and/or block conformational changes associated with the GTP bound state, leading to blockade of signal transmission with consequent decreased growth and apoptosis of Ral-dependent cancer cells. These compounds were identified by parallel use of virtual and physical screening of combinatorial chemical libraries.

Computational approaches developed by the inventors were used to analyze the three-dimensional structure of RalA to identify potential sites that can be exploited to selectively inhibit RalA protein interactions with effector proteins. These analyses included the use of RalA-GDP, and RalA-GTP in complex with exo84 and sec5. The potential protein binding sites are characterized by crevasses and depressions, present in Ral-GDP but not in Ral-GTP, that are sufficiently large to accommodate a molecule that can in turn be used to block the associated conformational change of RalA upon GTP binding, thus preventing effector engagement and downstream signaling. These pockets are located away from the nucleotide binding cavity that is located in the active site of the enzyme.

Computational screening of commercially available compound libraries was used to identify small molecules that dock in these allosteric protein pockets. To do so, RalA-GDP was set up for docking, and the ChemDiv library (v2006.5 including 500,000 compounds but excluding those possessing reactive groups, known ADME/toxicity, or physicochemical properties that lie outside 'drug-likeness' parameters (Lipinski's rule of 5 and Veber's Rule of 2)) at pH 7 was downloaded from the ZINC database (Irwin J J, Shoichet B K. ZINC—*A free database of commercially available compounds for virtual screening*. J Chem Inf Model 2005; 45:177-82) and docked onto the identified allosteric sites. Ligand molecules were assigned Gasteiger charges and polar hydrogen atoms by the ligand preparation module provided in the AutoDockTools. AutoDock4 was used to evaluate ligand binding energies over the conformational search space using the Lamarckian genetic algorithm. The top 88 compounds, ranked using methods developed for accurate prediction of free binding energy were selected for evaluation.

Because the crystal structure of RalB is not defined, the inventors screened GDP-loaded RalB protein against a 92,167-member encoded bead-based library. The screen was performed as a direct binding assay of FLAG-RalB at 500 nM to pools of beads. Each pool contained multiple copies of encoded immobilized compounds. A visible blue color developed upon FLAG-RalB binding by an ELISA, with mouse anti-FLAG, goat anti-mouse alkaline phosphatase conjugate, and the precipitating substrate BCIP. Blue beads were physically separated and decoded by mass spectroscopy. This search resulted in the identification of eleven compounds for further evaluation.

The inventors constructed the 3D structure of RalB using threading algorithms from the known RalA crystal structure (Nicely N I, Kosak J, de Serrano V, Mattos C. *Crystal structures of Ral-GppNHp and Ral-GDP reveal two binding sites that are also present in Ras and Rap*. Structure (Camb) 2004; 12:2025-36). "In silico" molecular modeling of the identified theoretical low-energy binding pockets was used to identify combinatorial hits on the surface of the simulated RalB. Surprisingly, the hits identified using this approach were bound to the same homologous pocket on RalA that was identified by the computational modeling approach. Thus, the two different approaches to model the RalA and RalB paralogs identified an identical molecular target site present in both proteins, which is distinct from the nucleotide (GDP) binding site.

Based on this in silico modeling, putative Ral inhibitors were designed and purchased or synthesized where necessary. Functional characterization was then used to evaluate putative GTPase inhibitors in living cells. Two complementary screens were developed to determine which of the 99 compounds that likely bound to the molecular target site would block Ral activity. Both assays were cell based to assure that any observed functional effects required drug penetration into a living cell.

The biochemical secondary screen was an ELISA, based on the canonical principle of binding of the activated (GTP-bound) forms of either RalA or RalB to RalBP1. The ELISA assay was adapted from the widely used Ral activation pull-down assays (Oxford G, Owens C R, Titus B J, et al. RalA and RalB: antagonistic relatives in cancer cell migration. Cancer Res 2005; 65:7111-20). A recombinant GST-His6-RalBP1 fusion protein purified from bacteria by GST affinity and then adsorbed via a His6 tag directly onto metal-chelate derivatized 96-well microplates was used in conjunction with stably transfected UMUC3 cell lines expressing either FLAG-RalA or FLAG-RalB. The ectopic protein functions as a reporter for Ral activation and the FLAG tag allows highly sensitive and specific detection of the protein. No commercial antibodies for either RalA or RalB were suitable as detection reagents in the ELISA format, so the inventors resorted to stable expression of FLAG-Ral in UMUC3. Robust signal to noise ratio (>100:1) was possible using anti-FLAG primary antibody and HRP-conjugated anti-mouse secondary antibody with signal proportional to input protein from 0.3 up to 10 mcg of total cell lysate. This permits use of lysates from cells cultured in 96 well microplates, where enough total cell protein can be recovered for analysis.

The functional secondary screen was based on the mediation of lipid raft trafficking by RalA when cells are re-plated. Thus, blocking RalA (siRNA depletion or dominant negative) inhibits the spread of normal, anchorage-dependent murine embryo fibroblasts (MEF) on fibronectin-coated cover slips. Importantly, Cav1$^{-/-}$ MEF Ss, are resistant to RalA depletion and hence these cells and their wild type counterparts were used to screen the putative Ral GTPase inhibitors identified in silico.

Compounds that showed activity in the computational and combinatorial screens as well as the ELISA and cell spreading assays were selected for dose response evaluation. Successful candidate compounds were found to have IC50's in the ELISA and cell spreading assay in the 1-2 µM range and successfully bound to RalB. Successful compounds were further evaluated in vitro using human cancer cells lines and their pharmacokinetics were evaluated in vivo using a mouse model.

Hence, the present invention provides Ral GTPase inhibiting compounds. These compouds can disrupt Ral protein binding with Ral-associated proteins exo84, sec5 and RalBP1. The identified Ral GTPase inhibitors can be used to block the associated conformational change of Ral proteins upon GTP binding, thus preventing effector engagement and downstream signaling. These inhibitors may also disrupt Ral protein binding to proteins that bind with Ral through other binding sites on the Ral protein, including proteins such as filamin A, PLD1 and ZONAB.

Thus, the present invention also provides methods of inhibiting the growth and/or metastasis of cancer in a mammal by inhibiting a Ral GTPase in the mammal. In a preferred embodiment, the Ral GTPase is at least one of the RalA and the RalB paralogs.

In another aspect, the invention is a method of inhibiting the growth and/or metastasis of cancer in a mammal by administering at least one compound of the invention, or pharmaceutically-acceptable salts thereof to the mammal.

The term "paralog" is used to denote genes in an organism that have been duplicated to occupy different positions in the same genome.

As used herein, the term "compound" means a chemical or biological molecule such as a simple or complex organic molecule, a peptide, a protein or an oligonucleotide.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Pharmaceutically-acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically-acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds, suitable for use in contact with the tissues of human beings and animals without excessive toxicity, irritation, allergic response, or other problems or complications, commensurate with a reasonable benefit/risk ratio.

Pharmaceutically-acceptable salt forms of compounds provided herein are synthesized from the compounds of the invention which contain a basic or acidic moiety by conventional chemical methods. Generally, such salts are, for example, prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in at page 1418 of Remington's Pharmaceutical Sciences, 17th ed., Mack Publishing Company, Easton, Pa., 1985.

The term "therapeutically-effective amount" or "therapeutic amount" of a compound of this invention means an amount effective to inhibit the formation or progression of cancer following administration to a mammal having a cancer.

The term "solvate" refers to the compound formed by the interaction of a solvent and a compound. Suitable solvates are pharmaceutically acceptable solvates, such as hydrates, including monohydrates and hemi-hydrates.

It will be appreciated by those skilled in the art that compounds of the invention having a chiral center may exist in, and may be isolated in, optically active and racemic forms. It is to be understood that the compounds of the present invention encompasses any racemic, optically-active, regioisomeric or stereoisomeric form, or mixtures thereof, which possess the therapeutically useful properties described herein. Where the compounds of the invention have at least one chiral center, they may exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diasteromers by standard techniques, such as the formation of stereoisomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers and enantiomers thereof are encompassed within the scope of the present invention.

It is well known in the art how to prepare optically active forms (for example, by resolution of the racemic form by recrystallization techniques, by synthesis from optically-active starting materials, by chiral synthesis, or by chromatographic separation using a chiral stationary phase). It is also to be understood that the scope of this invention encompasses not only the various isomers, which may exist but also the various mixtures of isomers, which may be formed. The resolution of the compounds of the present invention, their starting materials and/or the intermediates may be carried out by known procedures, e.g., as described in the four volume compendium Optical Resolution Procedures for Chemical Compounds: Optical Resolution Information Center, Manhattan College, Riverdale, N.Y., and in Enantiomers, Racemates and Resolutions, Jean Jacques, Andre Collet and Samuel H. Wilen; John Wiley & Sons, Inc., New York, 1981, which is incorporated in its entirety by this reference. Basically, the resolution of the compounds is based on the differences in the physical properties of diastereomers by attachment, either chemically or enzymatically, of an enantiomerically pure moiety resulting in forms that are separable by fractional crystallization, distillation or chromatography.

The compounds used in making the pharmaceutical compositions of the present invention may be purchased commercially. The compounds of the present invention, including the salts of these compounds, may also be prepared in ways well known to those skilled in the art of organic synthesis. The compounds of the invention may be prepared using the reactions performed in solvents appropriate to the reagents and materials employed and suitable for the transformation being effected. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used.

The pharmaceutical compositions of the invention contain one or more compounds of the invention and a pharmaceutically-acceptable carrier, which are media generally accepted in the art for the delivery of biologically active agents to animals, in particular, mammals. Pharmaceutically-acceptable carriers are formulated according to a number of factors well within the purview of those of ordinary skill in the art to determine and accommodate. These include, without limitation: the type and nature of the active agent being formulated; the subject to which the agent-containing composition is to be administered; the intended route of administration of the composition; and, the therapeutic indication being targeted. Pharmaceutically-acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically-acceptable carriers, and factors involved in their selection, are found in a variety of readily available sources, such as Remington's Pharmaceutical Sciences, 17th ed., Mack Publishing Company, Easton, Pa., 1985.

This invention further provides methods of treating a mammal afflicted with a cancer or preventing the metastasis of such cancer in a mammal, which includes administering to the mammal a pharmaceutical composition provided herein. Such compositions generally comprise a therapeutically effective amount of a compound of the invention in an amount effective to prevent, ameliorate, lessen or inhibit the cancer. Such amounts typically comprise from about 0.1 to about 100 mg of the compound per kilogram of body weight of the mammal to which the composition is administered. Therapeutically effective amounts can be administered according to any dosing regimen satisfactory to those of ordinary skill in the art.

Administration may be, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffering agents. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as, but not limited to, lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

A preferred formulation of the invention is a mono-phasic pharmaceutical composition suitable for parenteral or oral administration for the prevention, treatment or prophylaxis of a cancer, consisting essentially of a therapeutically-effective amount of a compound of the invention, and a pharmaceutically acceptable carrier.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn may depend upon crystal size and crystalline form. Alternatively, delayed absorption of a parenterally-administered drug is accomplished by dissolving or suspending the drug in an oil vehicle.

Injectable depot forms are made by forming microencapsulated matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the therapeutic compounds of the present invention.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical or transdermal administration of compounds of this invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required.

The ointments, pastes, creams and gels may contain, in addition to an active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical formulations include those suitable for administration by inhalation or insufflation or for nasal or intraocular administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more of the anti-cancer compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the invention may be administered by means of nose drops or a liquid spray, such as by means of a plastic bottle atomizer or metered-dose inhaler. Typical of atomizers are the Mistometer (Wintrop) and Medihaler (Riker).

Drops, such as eye drops or nose drops, may be formulated with an aqueous or nonaqueous base also comprising one or more dispersing agents, solubilizing agents or suspending agents. Liquid sprays are conveniently delivered from pressurized packs. Drops can be delivered by means of a simple eye dropper-capped bottle or by means of a plastic bottle adapted to deliver liquid contents dropwise by means of a specially shaped closure.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The dosage formulations provided by this invention may contain the therapeutic compounds of the invention, either alone or in combination with other therapeutically active ingredients, and pharmaceutically acceptable inert excipients. The term 'pharmaceutically acceptable inert excipients' includes at least one of diluents, binders, lubricants/glidants, coloring agents and release modifying polymers.

Suitable antioxidants may be selected from amongst one or more pharmaceutically acceptable antioxidants known in the art. Examples of pharmaceutically acceptable antioxidants include butylated hydroxyanisole (BHA), sodium ascorbate, butylated hydroxytoluene (BHT), sodium sulfite, citric acid, malic acid and ascorbic acid. The antioxidants may be present in the dosage formulations of the present invention at a concentration between about 0.001% to about 5%, by weight, of the dosage formulation.

Suitable chelating agents may be selected from amongst one or more chelating agents known in the art. Examples of suitable chelating agents include disodium edetate (EDTA), edetic acid, citric acid and combinations thereof. The chelating agents may be present in a concentration between about 0.001% and about 5%, by weight, of the dosage formulation.

The dosage form may include one or more diluents such as lactose, sugar, cornstarch, modified cornstarch, mannitol, sorbitol, and/or cellulose derivatives such as wood cellulose and microcrystalline cellulose, typically in an amount within the range of from about 20% to about 80%, by weight.

The dosage form may include one or more binders in an amount of up to about 60% w/w. Examples of suitable binders include methyl cellulose, hydroxypropyl cellulose, hydroxypropylmethyl cellulose, polyvinyl pyrrolidone, eudragits, ethyl cellulose, gelatin, gum arabic, polyvinyl alcohol, pullulan, carbomer, pregelatinized starch, agar, tragacanth, sodium alginate, microcrystalline cellulose and the like.

Examples of suitable disintegrants include sodium starch glycolate, croscarmellose sodium, crospovidone, low substituted hydroxypropyl cellulose, and the like. The concentration may vary from 0.1% to 15%, by weight, of the dosage form.

Examples of lubricants/glidants include colloidal silicon dioxide, stearic acid, magnesium stearate, calcium stearate, talc, hydrogenated castor oil, sucrose esters of fatty acid, microcrystalline wax, yellow beeswax, white beeswax, and the like. The concentration may vary from 0.1% to 15%, by weight, of the dosage form.

Release modifying polymers may be used to form extended release formulations containing the therapeutic compounds of the invention. The release modifying polymers may be either water-soluble polymers, or water insoluble polymers. Examples of water-soluble polymers include polyvinylpyrrolidone, hydroxy propylcellulose, hydroxypropyl methylcellulose, vinyl acetate copolymers, polyethylene oxide, polysaccharides (such as alginate, xanthan gum, etc.), methylcellulose and mixtures thereof. Examples of water-insoluble polymers include acrylates such as methacrylates, acrylic acid copolymers; cellulose derivatives such as ethylcellulose or cellulose acetate; polyethylene, and high molecular weight polyvinyl alcohols.

Also encompassed by the present invention are methods for screening potential therapeutic agents that may prevent, treat or inhibit the metastasis of lung cancer, by inhibiting a Ral GTPase comprising: (a) combining a Ral GTPase and a potential therapeutic compound under conditions in which they interact, and; (b) monitoring the enzymatic activity of the Ral GTPase; wherein a potential therapeutic compound is selected for further study when it inhibits the enzymatic activity compared to a control sample to which no potential therapeutic compound has been added. In one embodiment, the potential therapeutic compound is selected from the group consisting of a pharmaceutical agent, a cytokine, a small molecule drug, a cell-permeable small molecule drug, a hormone, a combination of interleukins, a lectin, a bispecific antibody, and a peptide mimetic.

One embodiment of the invention relates to a compound of the invention for use in the treatment or prevention of cancer, or a metastasis of a cancer, in a mammal. A related embodiment of the invention relates to a composition of the invention for use in the treatment or prevention of cancer, or a metastasis of a cancer, in a mammal.

Another embodiment of the invention relates to the use of any of the compounds or compositions of the invention in the preparation of a medicament for the inhibition of the growth or metastasis of a cancer in a mammal.

Each publication or patent cited herein is incorporated herein by reference in its entirety.

EXAMPLES

The following examples are provided to illustrate certain aspects, embodiments, and configurations of the disclosure and are not to be construed as limitations on the disclosure, as set forth in the appended claims.

Example 1

Screening of Putative Ral GTPase Inhibitors

Because the crystal structure of RalB is not defined, the inventors screened GDP-loaded RalB protein against a 92,167-member encoded bead-based library. The screen was performed as a direct binding assay of FLAG-RalB at 500 nM to pools of beads. Each pool contained multiple copies of encoded immobilized compounds. A visible blue color developed upon FLAG-RalB binding by an ELISA, with mouse anti-FLAG, goat anti-mouse alkaline phosphatase conjugate, and the precipitating substrate BCIP. Blue beads were physically separated and decoded by mass spectroscopy. This search resulted in the identification of eleven compounds for further evaluation.

The inventors constructed the 3D structure of RalB using threading algorithms from the known RalA crystal structure (Nicely N I, Kosak J, de Serrano V, Mattos C. *Crystal structures of Ral-GppNHp and Ral-GDP reveal two binding sites that are also present in Ras and Rap*. Structure (Camb) 2004; 12:2025-36). "In silico" molecular modeling of the identified theoretical low-energy binding pockets was used to identify combinatorial hits on the surface of the simulated RalB. Surprisingly, the hits identified using this approach were bound to the same homologous pocket on RalA that was identified by the computational modeling approach. Thus, the two different approaches to model the RalA and RalB paralogs identified an identical molecular target site present in both proteins, which is distinct from the nucleotide (GDP) binding site.

Based on this in silico modeling, putative Ral inhibitors were designed and purchased or synthesized where necessary. Functional characterization was then used to evaluate putative GTPase inhibitors in living cells. Two complementary screens were developed to determine which of the 99 compounds that likely bound to the molecular target site would block Ral activity. Both assays were cell based to assure that any observed functional effects required drug penetration into a living cell. For example, FIG. 1 shows the dose-inhibition activity of two compounds of the invention, RBC8 and RBC10, on growth of human lung cancer cell lines. Calu-6: human lung adenocarcinoma. H157: squamous cell carcinoma. H358: bronchioalveolar carcinoma. Calu-3: human airway epithelial cell line of serous gland origin. 88 of the screened compounds are shown in Table 1.

TABLE 1
Chemical Structures of Screened Compounds
| Study ID | Structure |
|---|---|
| RLA001 | 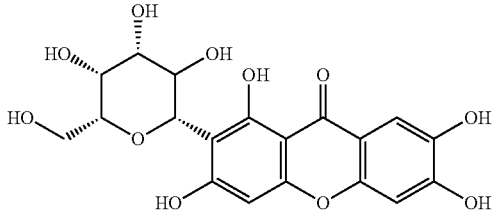 |
| RLA002 | 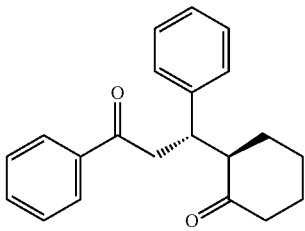 |
| RLA003 | 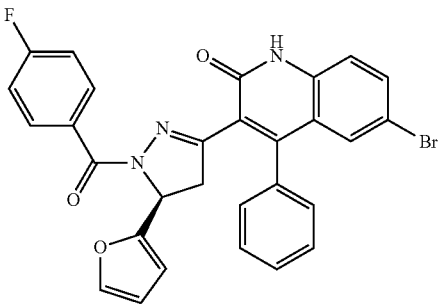 |
| RLA004 | 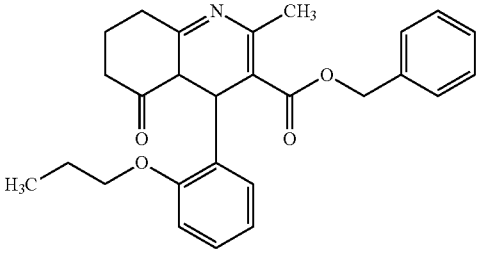 |
| RLA005 | 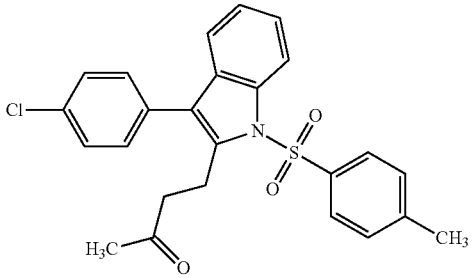 |
| RLA006 | 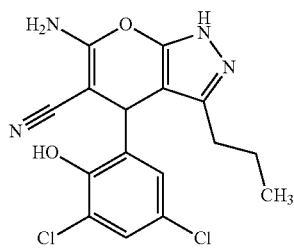 |

TABLE 1-continued
Chemical Structures of Screened Compounds
| Study ID | Structure |
|---|---|
| RLA007 | 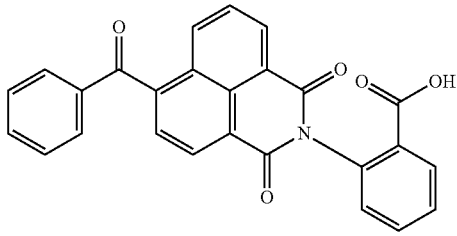 |
| RLA008 | 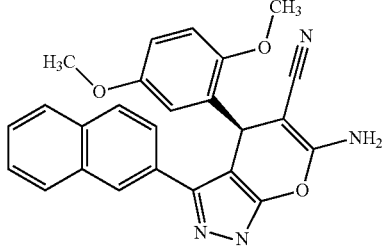 |
| RLA009 | 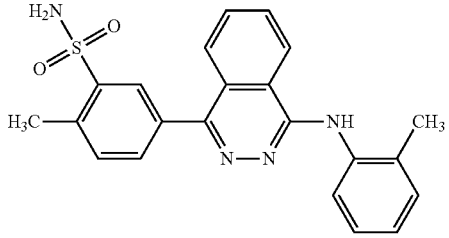 |
| RLA010 | 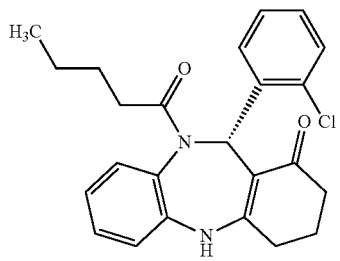 |
| RLA011 | 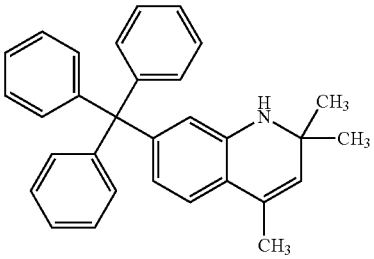 |

TABLE 1-continued

Chemical Structures of Screened Compounds

| Study ID | Structure |
|---|---|
| RLA012 | 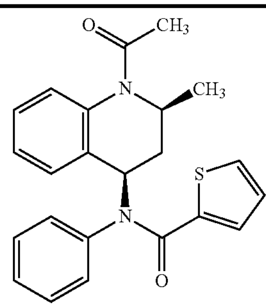 |
| RLA013 | 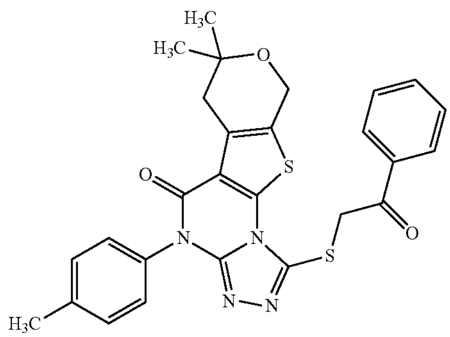 |
| RLA014 | 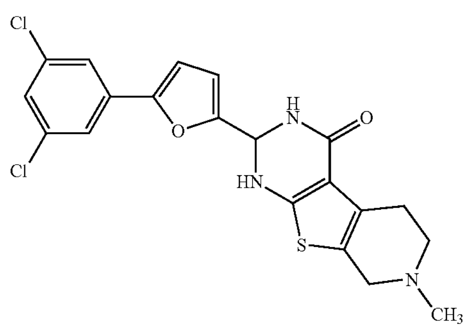 |
| RLA015 | 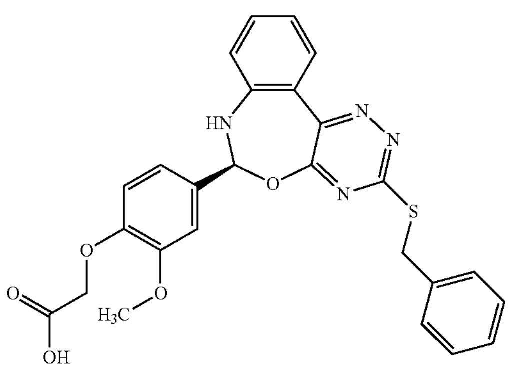 |
| RLA016 | 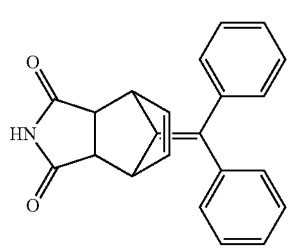 |

TABLE 1-continued

Chemical Structures of Screened Compounds

| Study ID | Structure |
|---|---|
| RLA017 | 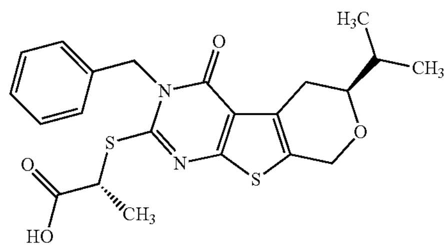 |
| RLA018 | 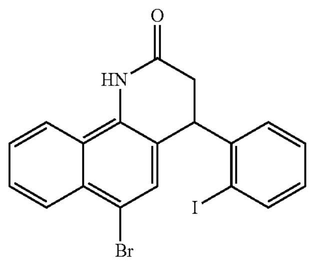 |
| RLA019 | 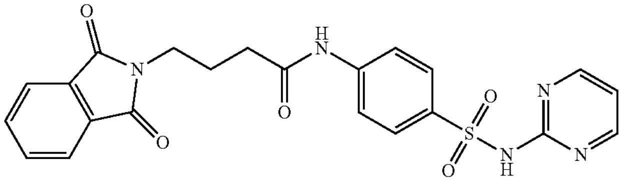 |
| RLA020 | 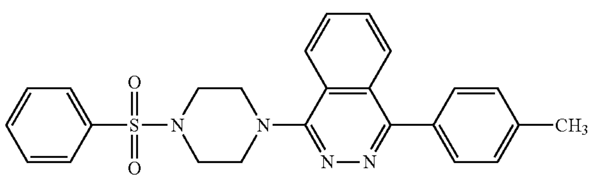 |
| RLA021 | 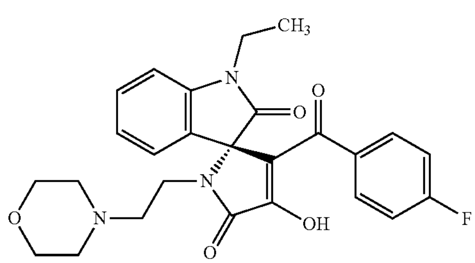 |
| RLA022 | 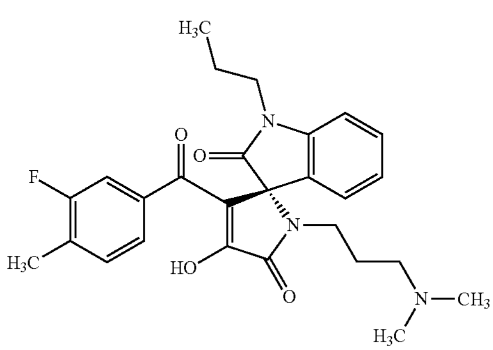 |

TABLE 1-continued
Chemical Structures of Screened Compounds
| Study ID | Structure |
|---|---|
| RLA023 | 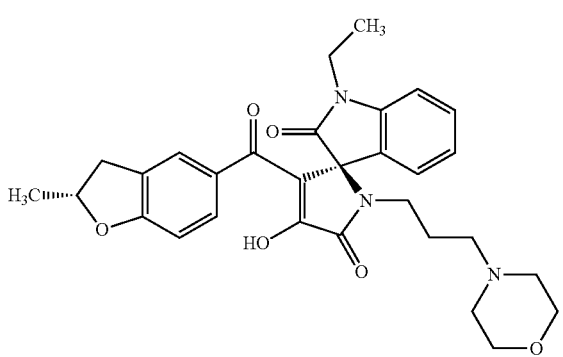 |
| RLA024 | 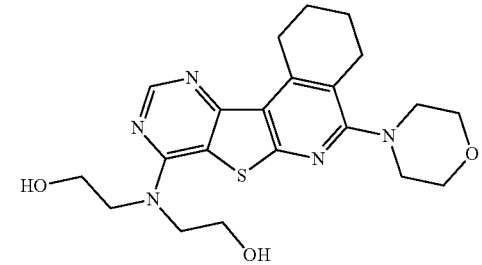 |
| RLA025 | 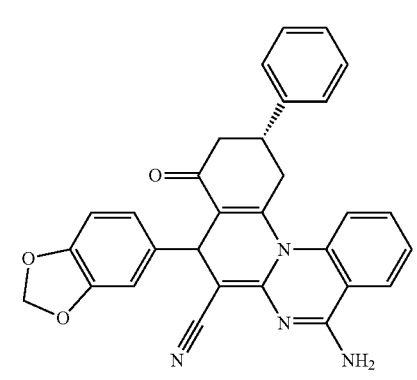 |
| RLA026 | 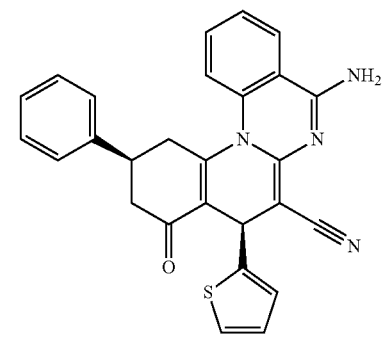 |

TABLE 1-continued
Chemical Structures of Screened Compounds
| Study ID | Structure |
|---|---|
| RLA027 | 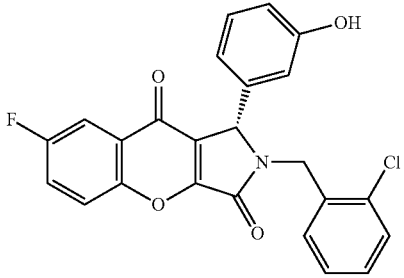 |
| RLA028 | 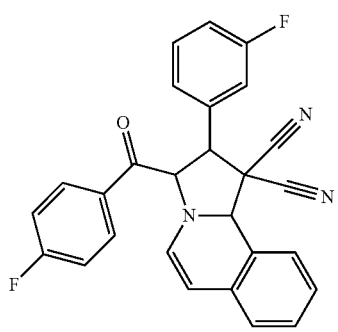 |
| RLA029 | 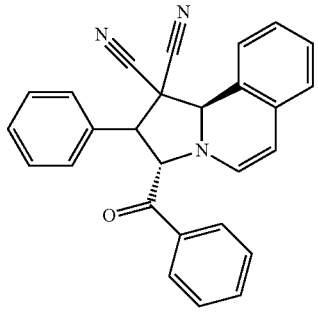 |
| RLA030 | 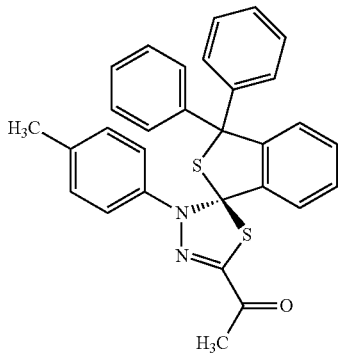 |
| RLA031 | 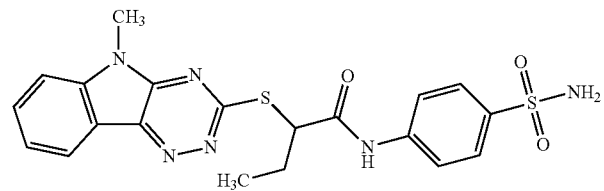 |

TABLE 1-continued

| Chemical Structures of Screened Compounds | |
|---|---|
| Study ID | Structure |
| RLA032 | |
| RLA033 | |
| RLA034 | |
| RLA035 | |
| RLA036 | |

TABLE 1-continued
Chemical Structures of Screened Compounds
| Study ID | Structure |
|---|---|
| RLA037 | 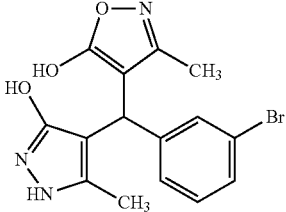 |
| RLA038 | 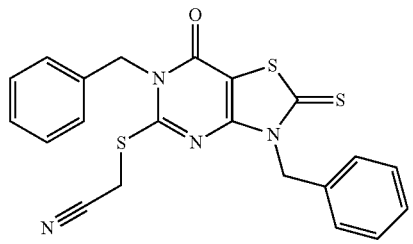 |
| RLA039 | 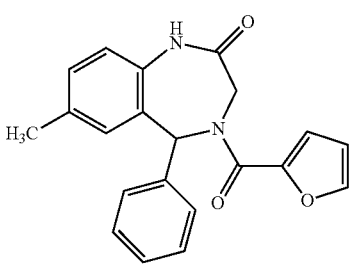 |
| RLA040 | 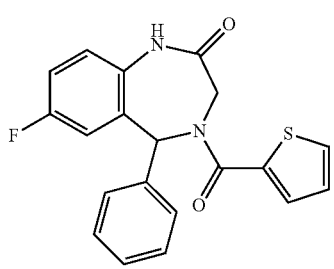 |
| RLA041 | 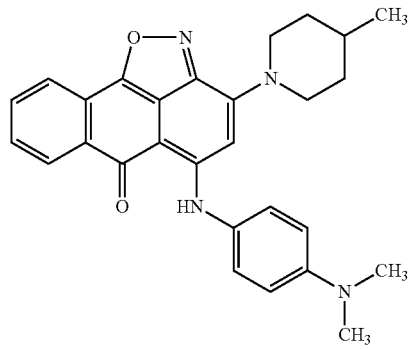 |

TABLE 1-continued
| Study ID | Structure |
|---|---|
| RLA042 | 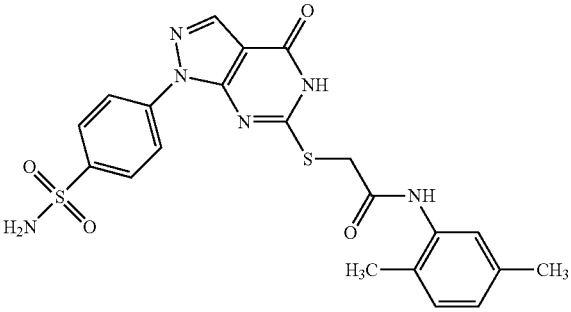 |
| RLA043 | 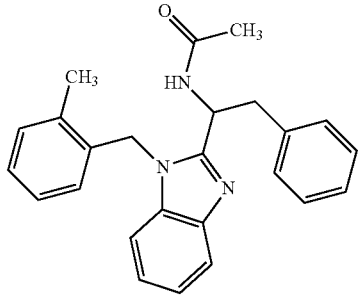 |
| RLA044 | 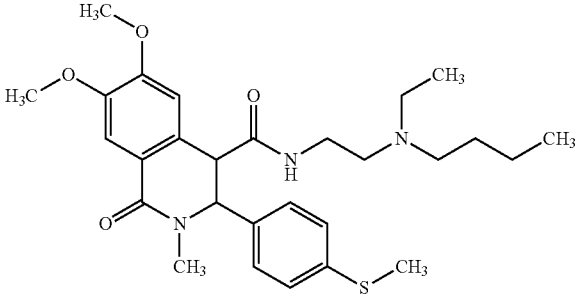 |
| RLA045 | 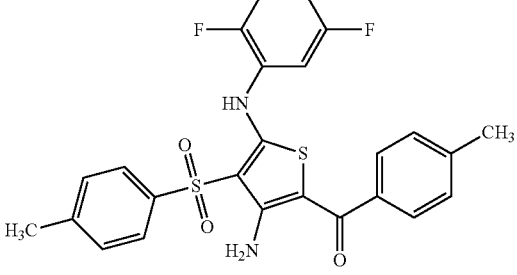 |
| RLA046 | 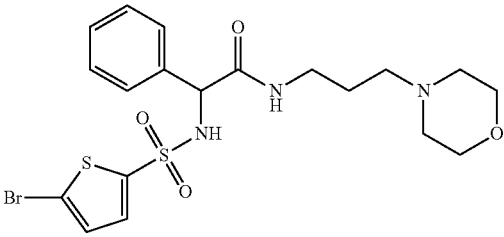 |

TABLE 1-continued
Chemical Structures of Screened Compounds
| Study ID | Structure |
|---|---|
| RLA047 | 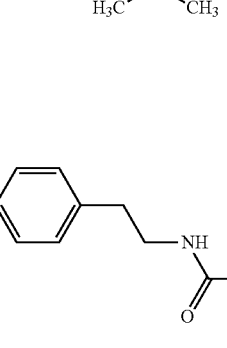 |
| RLA048 | 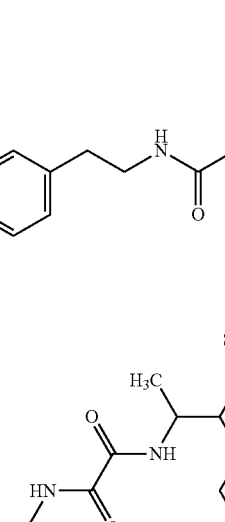 |
| RLA049 | 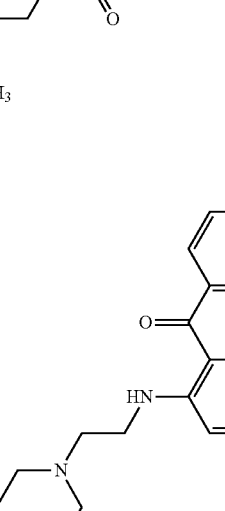 |
| RLA050 | 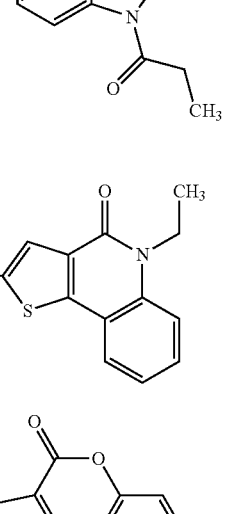 |
| RLA051 | 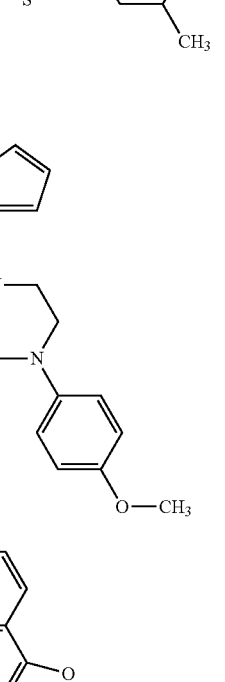 |

TABLE 1-continued
Chemical Structures of Screened Compounds
| Study ID | Structure |
|---|---|
| RLA052 | 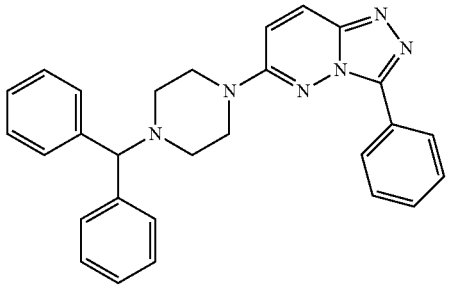 |
| RLA053 | 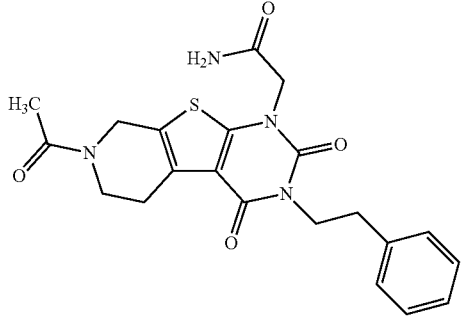 |
| RLA054 | 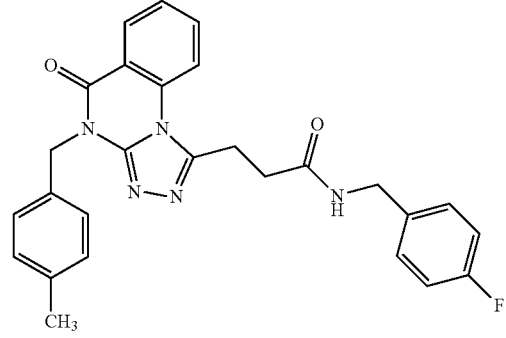 |
| RLA055 | 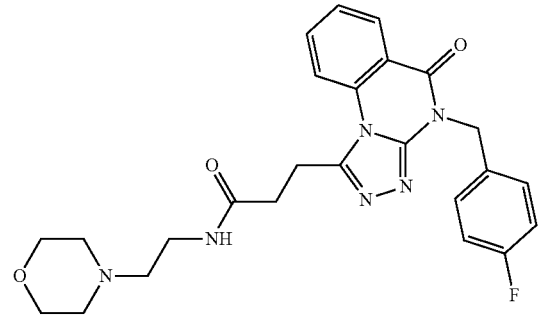 |

TABLE 1-continued

Chemical Structures of Screened Compounds

| Study ID | Structure |
|---|---|
| RLA056 | 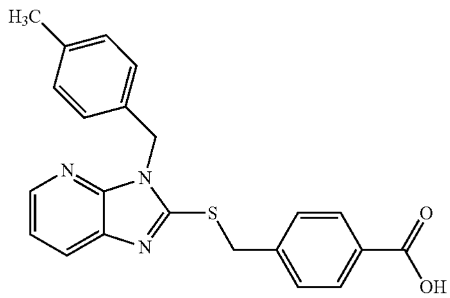 |
| RLA057 | 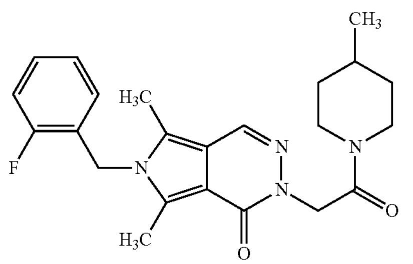 |
| RLA058 | 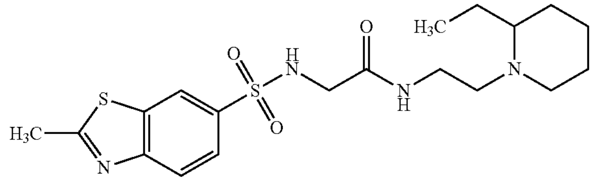 |
| RLA059 | 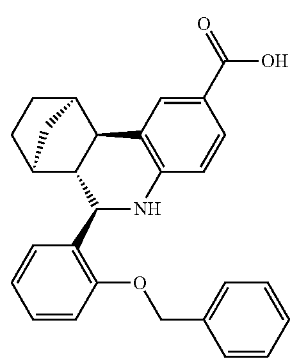 |
| RLA060 | 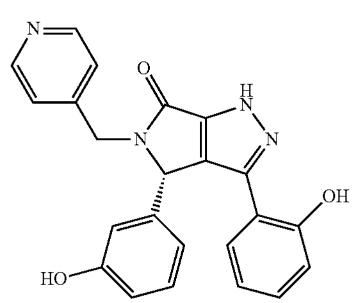 |

TABLE 1-continued
Chemical Structures of Screened Compounds
| Study ID | Structure |
|---|---|
| RLA061 | 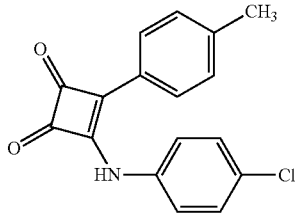 |
| RLA062 | 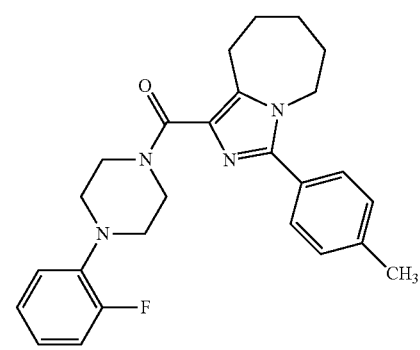 |
| RLA063 | 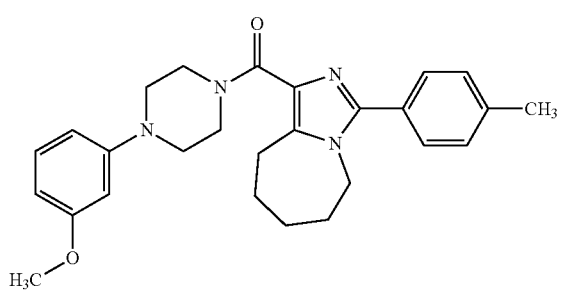 |
| RLA064 | 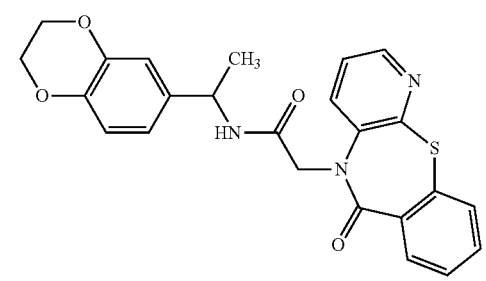 |
| RLA065 | 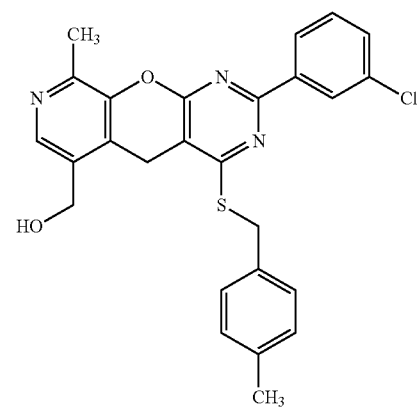 |

TABLE 1-continued

Chemical Structures of Screened Compounds

| Study ID | Structure |
|---|---|
| RLA066 | 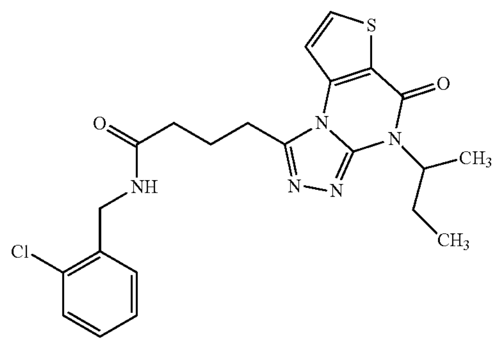 |
| RLA067 | 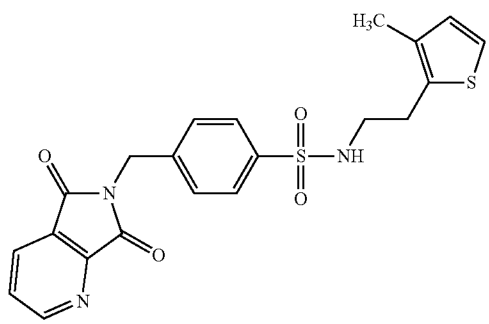 |
| RLA068 | 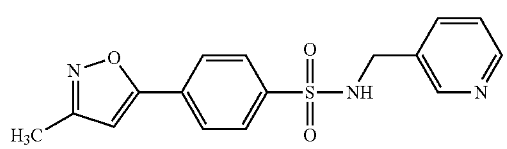 |
| RLA069 | 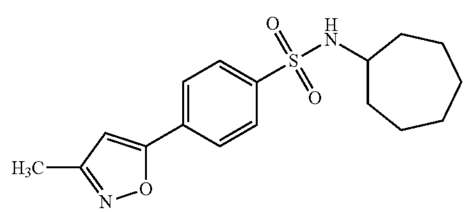 |
| RLA070 | 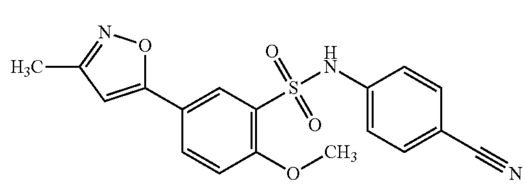 |
| RLA071 | 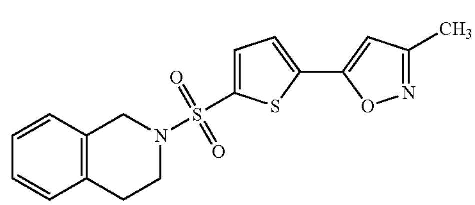 |

TABLE 1-continued

Chemical Structures of Screened Compounds

| Study ID | Structure |
|---|---|
| RLA072 | 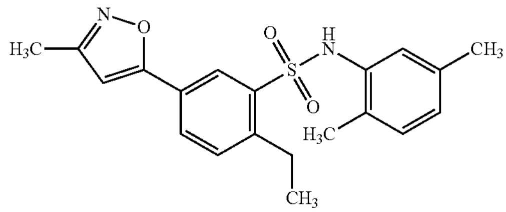 |
| RLA073 | 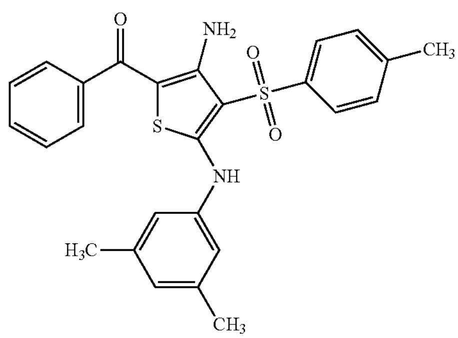 |
| RLA074 | 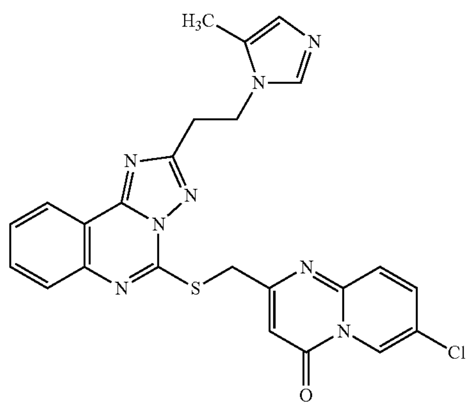 |
| RLA075 | 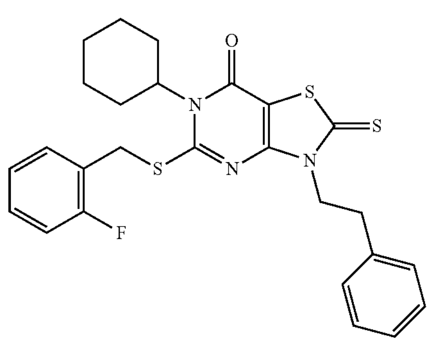 |
| RLA076 | 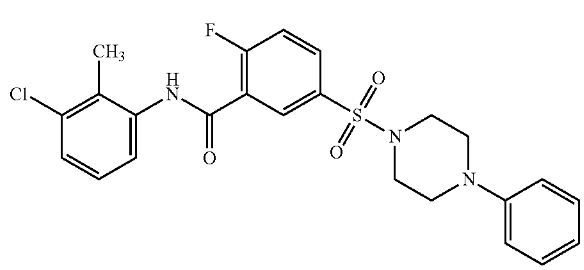 |

TABLE 1-continued

Chemical Structures of Screened Compounds

| Study ID | Structure |
|---|---|
| RLA077 | 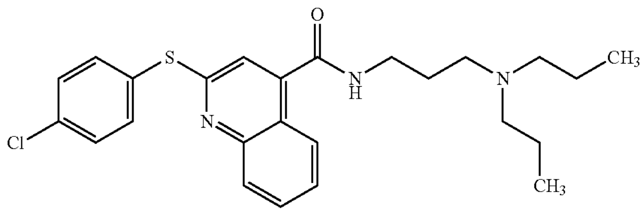 |
| RLA078 | 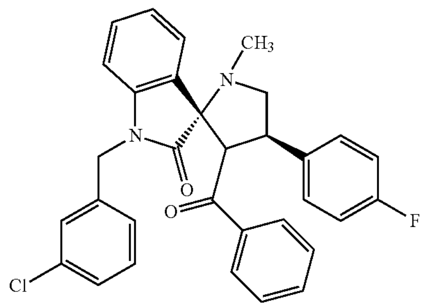 |
| RLA079 | 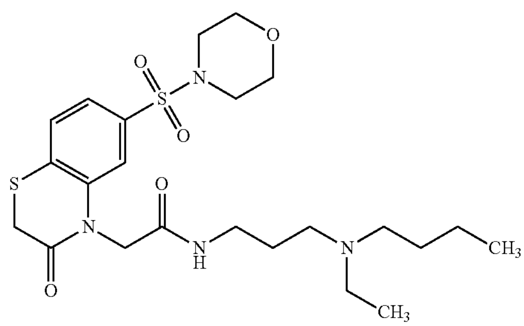 |
| RLA080 | 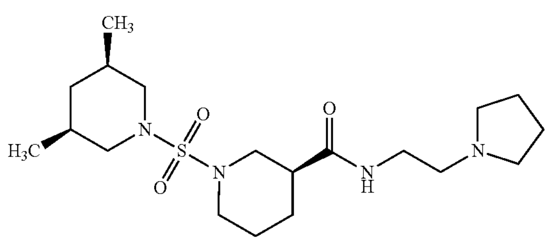 |
| RLA081 | 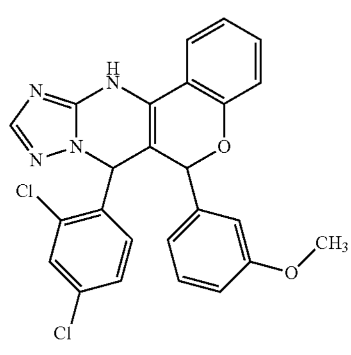 |

51
TABLE 1-continued
Chemical Structures of Screened Compounds
| Study ID | Structure |
|---|---|
| RLA082 | 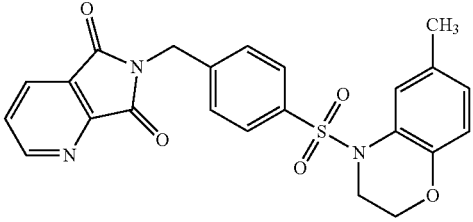 |
| RLA083 | 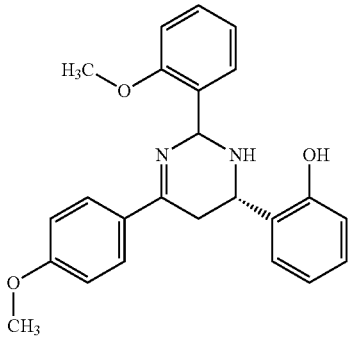 |
| RLA084 | 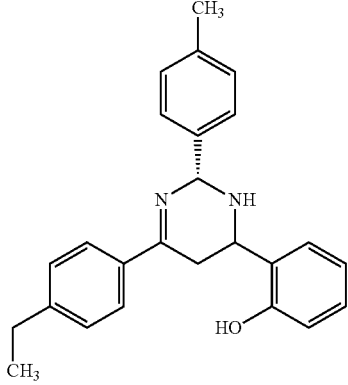 |
| RLA085 | 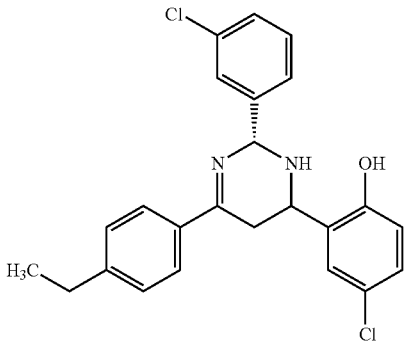 |

TABLE 1-continued
Chemical Structures of Screened Compounds
| Study ID | Structure |
|---|---|
| RLA086 | 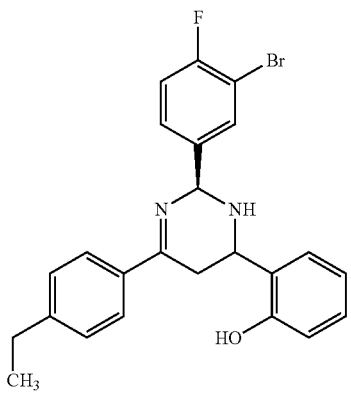 |
| RLA087 | 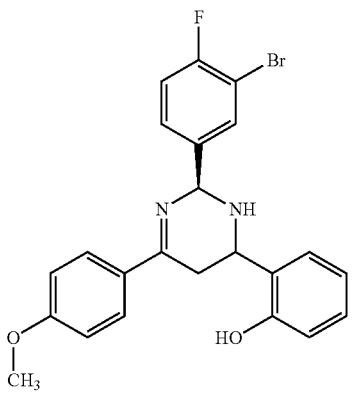 |
| RLA088 | 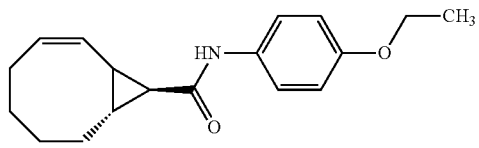 |

Example 2

Synthesis of Putative Ral GTPase Inhibitors

Certain embodiments of the invention are illustrated by the following synthetic schemes.

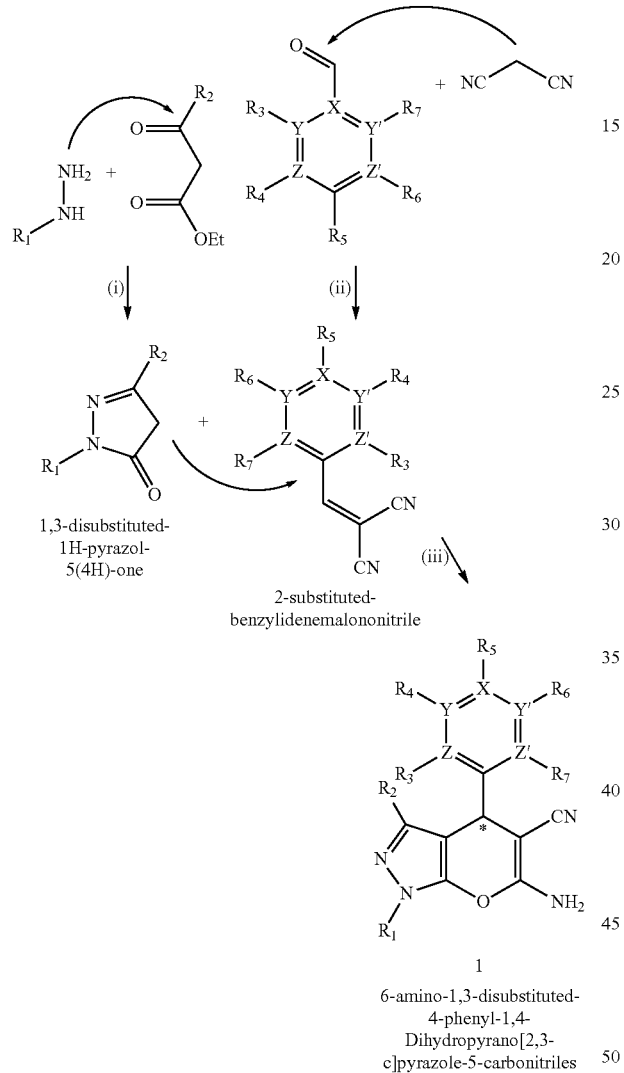

Scheme 1 General pathway to prepare Formula 1 related compounds 1,3-disubstituted-1H-pyrazol-5(4H)-one 2-substituted-benzylidenemalononitrile 6-amino-1,3-disubstituted-4-phenyl-1,4-Dihydropyrano[2,3-c]pyrazole-5-carbonitriles 1

*denotes a chiral center

Scheme 2 General pathway to prepare Formula 2 related compounds

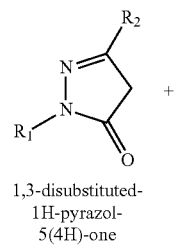

1,3-disubstituted-1H-pyrazol-5(4H)-one

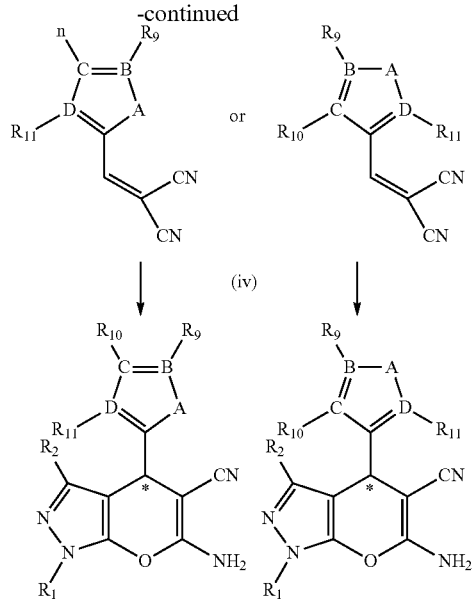

*chiral center

Chemical Synthesis Examples

General Procedure A; 3-methyl-1-phenyl-1H-pyrazol-5(4H)-one UC-E1

A solution of ethyl acetoacetate (9.02 mL, 71.2 mmol, 1.1 equ.) in ethanol (130 mL) was treated at 0° C. with phenylhydrazine (7.00 g, 64.7 mmol, 1.0 equ.). The mixture was allowed to come to slowly ward to ambient temperature and then heated to 60° C. (3 h). The solvent was removed under vacuum and the residue purified by column chromatography on silica gel (ethyl acetate:hexanes; 1:1) to give 3-methyl-1-phenyl-1H-pyrazol-5(4H)-one (7.60 g, 43.6 mmol, 67%) as a light yellow powder. $^1$H-NMR (400 MHz) CDCl$_3$: 7.87-7.85 (d, 2H), 7.41-7.37 (t, 2H), 7.19-7.16 (t, 1H), 3.42 (s, 2H), 2.19 (s, 3H), $^{13}$C-NMR (100 MHz) CDCl$_3$: 170.5, 156.2, 138.0, 128.8, 125.0, 118.8, 43.0, 17.0; LC/MS-MS: 175.0→77.1 m/z; GS1 and GS2 at 30, DP=56, CE=25, CXP=4, $t_R$=3.52 min.

1,3-dimethyl-1H-pyrazol-5(4H)-one UC-E2

Following the 'general procedure A'; ethyl acetoacetate (15.1 mL, 119 mmol, 1.1 equ.) in ethanol (200 mL) was treated at 0° C. with methylhydrazine (5.00 g, 109 mmol, 1.0 equ.) to afford 1,3-dimethyl-1H-pyrazol-5(4H)-one (8.02 g, 71.5 mmol, 66%) after purification by crystallization (DCM and n-hexanes) as a white off solid. $^1$H-NMR (400 MHz) CDCl$_3$: 3.25 (s, 3H), 3.16 (s, 2H), 2.08 (s, 3H), $^{13}$C-NMR (100 MHz) CDCl$_3$: 172.2, 155.4, 138.0, 41.3, 31.0, 16.8.

1-methyl-3-phenyl-1H-pyrazol-5(4H)-one UC-E3

According to General Procedure A; ethyl benzoylacetate (18.4 mL, 95.5 mmol, 1.1 equ.) in ethanol (180 mL) was treated at 0° C. with methylhydrazine (4.57 mL, 86.8 mmol, 1.0 equ.) to give 1-methyl-3-phenyl-1H-pyrazol-5(4H)-one (11.0 g 63.1 mmol, 73%) after purification by crystallization (ethanol) as a light yellow solid. $^1$H-NMR (400 MHz)

CDCl$_3$: 7.67-7.65 (m, 2H), 7.42-7.41 (m, 3H), 3.60 (s, 2H), 3.41 (s, 3H), $^{13}$C-NMR (100 MHz) CDCl$_3$: 171.8, 154.2, 131.0, 130.3, 128.8, 125.6, 37.9, 31.4. LC/MS-MS: 175.0→77.2 m/z; GS1 and GS2 at 30, DP=66, CE=43, CXP=4, t$_R$=3.45 min.

1,3-diphenyl-1H-pyrazol-5(4H)-one UC-E4

According to General Procedure A; ethyl benzoylacetate (12.2 mL, 71.2 mmol, 1.1 equ.) in ethanol (130 mL) was treated at 0° C. with phenylhydrazine (7.00 g, 71.2 mmol, 1.0 equ.) to give 1,3-diphenyl-1H-pyrazol-5(4H)-one (6.75 g, 28.6 mmol, 44%) after purification by column chromatography on silica gel (hexanes:ethyl acetate; 4:1) and crystallization (ethanol) as a white off solid. $^1$H-NMR (400 MHz) DMSO: 11.84 (s, 1H), 7.84-7.82 (d, 4H), 7.50-7.40 (m, 4H), 7.34-7.27 (m, 2H), 6.02 (s, 1H), $^{13}$C-NMR (100 MHz) DMSO: 154.2, 150.0, 139.3, 133.8, 129.3, 129.0, 128.2, 126.1, 125.5, 121.5, 85.5; LC/MS-MS: 237.0→77.1 m/z; GS1 and GS2 at 30, DP=81, CE=68, CXP=4, t$_R$=4.15 min.

1-benzyl-3-phenyl-1H-pyrazol-5(4H)-one UC-E5

A solution of ethyl benzoylacetate (4.80 mL, 28.2 mmol, 1.1 equ.) in ethanol (60 mL) was treated at 0° C. with benzlhydrazine (5.00 g, 25.6 mmol, 1.0 equ.). The mixture was slowly warmed to ambient temperature and heated to 60° C. (16 h). The reaction mixture was concentrated and diluted with ethanol (100 mL) and then 3.0 g of sodium ethoxide added and stirred (40 h). The solid was filtered off and the solvent removed in vacuo. The residue was purified by column chromatography on silica gel (4:1 n-hexanes:ethyl acetate to 100% ethyl acetate) to give 1-benzyl-3-phenyl-1H-pyrazol-5(4H)-one (0.255 g, 1.02 mmol, 4%) as a light orange solid. $^1$H-NMR (400 MHz) DMSO: 11.17 (s, 1H), 7.71-7.70 (d, 2H), 7.37-7.31 (m, 4H), 7.27-7.20 (m, 4H), 5.85 (s, 1H), 5.13 (s, 2H), $^{13}$C-NMR (100 MHz) DMSO: 153.6, 148.6, 138.3, 134.4, 128.8, 128.8, 127.6, 127.6, 125.1, 83.7, 50.0; LC/MS-MS: 251.1→91.1 m/z; GS1 and GS2 at 30, DP=2, CE=33, CXP=14, t$_R$=4.01 min.

3-(3,4-dimethoxyphenyl)-1-methyl-1H-pyrazol-5(4H)-one UC-E6

Using General Procedure A; ethyl 3,4-dimethoxybenzoylacetate (5.00 g, 19.8 mmol, 1.1 equ.) in ethanol (60 mL) was treated at 0° C. with methylhydrazine (0.95 mL, 19.8 mmol, 1.0 equiv.) to give 3-(3,4-dimethoxyphenyl)-1-methyl-1H-pyrazol-5(4H)-one (1.86 g, 7.94 mmol, 44%) after purification by chromatography on silica gel (hexanes:ethyl acetate; 4:1 to 1:1) as a light yellow powder. $^1$H-NMR (400 MHz) CDCl$_3$: 7.35-7.35 (d, 1H), 7.06-7.04 (dd, 1H), 6.87-6.85 (d, 1H), 3.94 (s, 3H), 3.92 (s, 3H), 3.57 (s, 2H), 3.39 (s, 3H), $^{13}$C-NMR (100 MHz) CDCl$_3$: 171.6, 154.1, 151.1, 149.4, 124.1, 119.6, 110.7, 107.3, 55.9, 55.9, 38.0, 31.3; LC/MS-MS: 235.1→219.0 m/z; GS1 and GS2 at 30, DP=66, CE=33, CXP=14, t$_R$=3.26 min.

3-(3,4-dimethoxyphenyl)-1-phenyl-1H-pyrazol-5(4H)-one UC-E7

Using General Procedure A; ethyl 3,4-dimethoxybenzoylacetate (3.00 g, 11.9 mmol, 1.1 equ.) in ethanol (60 mL) was treated at 0° C. with phenylhydrazine (1.17 mL, 10.8 mmol, 1.0 equ.) to afford 3-(3,4-dimethoxyphenyl)-1-phenyl-1H-pyrazol-5(4H)-one (920 mg, 2.32 mmol, 22%) after purification by crystallization (ethanol) as a yellow powder. $^1$H-NMR (400 MHz) CDCl$_3$: 8.00-7.97 (d, 1H), 7.48-7.42 (m, 3H), 7.25-7.21 (t, 1H), 7.17-7.14 (dd, 1H), 6.91-6.89 (d, 1H), 3.98 (s, 3H), 3.95 (s, 3H), 3.83 (s, 2H), $^{13}$C-NMR (100 MHz) CDCl$_3$: 170.1, 154.4, 151.4, 149.4, 138.1, 128.8, 125.2, 123.8, 120.1, 119.1, 110.7, 107.6, 56.0, 56.0, 39.7; LC/MS-MS: 297.0→218.2 m/z; GS1 and GS2 at 30, DP=96, CE=37, CXP=18, t$_R$=3.98 min.

3-(4-methoxyphenyl)-1-phenyl-1H-pyrazol-5(4H)-one UC-E8

Using General Procedure A; ethyl-4-methoxybenzoylacetate (7.00 g, 27.8 mmol, 1.1 equ.) in ethanol (100 mL) was treated at 0° C. with phenylhydrazine (2.50 mL, 25.3 mmol, 1.0 equ.) to give 3-(4-methoxyphenyl)-1-phenyl-1H-pyrazol-5(4H)-one (5.21 g, 19.6 mmol, 78%) after crystallization (ethanol) as a light yellow solid. $^1$H-NMR (400 MHz) CDCl$_3$: 7.99-7.97 (d, 1H), 7.66-7.64 (d, 2H), 7.44-7.40 (t, 2H), 7.22-7.18 (t, 1H), 6.94-6.92 (d, 2H), 3.82 (s, 3H), 3.68 (s, 3H), $^{13}$C-NMR (100 MHz) CDCl$_3$: 170.1, 161.5, 154.4, 138.2, 128.8, 127.5, 125.0, 123.5, 118.8, 114.2, 55.3, 39.6; LC/MS-MS: 267.0→77.2 m/z; GS1 and GS2 at 30, DP=81, CE=65, CXP=4, t$_R$=4.15 min.

3-(4-methoxyphenyl)-1-methyl-1H-pyrazol-5(4H)-one UC-E9

Using General Procedure A; ethyl-4-methoxybenzoylacetate (7.00 g, 27.8 mmol, 1.1 equ.) in ethanol (100 mL) was treated at 0° C. with methyllhydrazine (1.30 mL, 25.2 mmol, 1.0 equ.) to give 3-(4-methoxyphenyl)-1-methyl-1H-pyrazol-5(4H)-one (3.00 g, 14.7 mmol, 58%) after crystallization from ethanol as a light yellow solid. $^1$H-NMR (400 MHz) DMSO: 10.94 (s, 1H), 7.63-7.60 (d, 2H), 6.92-6.90 (d, 2H), 5.70 (s, 1H), 3.76 (s, 3H), 3.54 (s, 3H), $^{13}$C-NMR (100 MHz) CDCl$_3$: 161.1, 153.4, 147.9, 126.3, 114.6, 114.4, 83.1, 59.7, 31.3; LC/MS-MS: 205.0→190.1 m/z; GS1 and GS2 at 30, DP=51, CE=29, CXP=12, t$_R$=3.44 min.

6-amino-3-methyl-1,4-diphenyl-1,4-dihydropyrano[2,3-c]pyrazole-5-carbonitrile UC-E10

To a stirred solution of benzaldehyde (290 μL, 2.87 mmol), malononitrile (190 mg, 2.87 mmol) and 3-methyl-1-phenyl-1H-pyrazol-5(4H)-one (500 mg, 2.87 mmol) in anhydrous DCM (60 mL) was added anhydrous Na$_2$SO$_4$ (407 mg, 2.87 mmol) and ethylhydrocupreine hydrochloride (46 mg, 0.122 mmol). The reaction mixture was stirred at room temperature (25 h). After filtration and washing with DCM, the solvent was removed under reduced pressure. The crude mixture was subjected to flash column chromatography over silica gel (hexanes:ethyl acetate; 1:1) to give 6-amino-3-methyl-1,4-diphenyl-1,4-dihydropyrano[2,3-c]pyrazole-5-carbonitrile (270 mg, 0.822 mmol, 29%) as white solid. $^1$H-NMR (400 MHz) CDCl$_3$: 7.69-7.66 (d, 2H), 7.50-7.46 (t, 2H), 7.39-7.26 (m, 6H), 4.68 (s, 1H), 4.67 (s, 2H), 1.91 (s, 3H), $^{13}$C-NMR (100 MHz) CDCl$_3$: 158.1, 146.4, 143.8, 141.9, 137.5, 129.2, 128.8, 127.8, 127.5, 126.7, 121.2, 119.0, 98.3, 64.0, 37.4, 12.8; LC/MS-MS: 329.1→263.1 m/z; GS1 and GS2 at 30, DP=56, CE=31, CXP=18, t$_R$=4.18 min.

6-amino-4-(4-fluorophenyl)-3-methyl-1-phenyl-1,4-dihydropyrano[2,3-c]pyrazole-5-carbonitrile UC-E11

A mixture of the 4-fluourobenzaldehyde (356 mg, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of the 3-methyl-1-phenyl-1H-pyrazol-5(4H)-one (500 mg, 2.87 mmol, 1 equ.). The reaction mixture was concentrated and the precipitate filtered and re-crystallized from ethanol to give 6-amino-4-(4-fluorophenyl)-3-methyl-1-phenyl-1,4-dihydropyrano[2,3-c]pyrazole-5-carbonitrile (85.0 mg, 0.245 mmol, 9%) as a white solid. $^1$H-NMR (400 MHz) CDCl$_3$: 7.68-7.66 (d, 2H), 7.50-7.46 (t, 2H), 7.34-7.32 (t, 1H), 7.28-7.22 (m, 2H) 7.08-7.04 (t, 2H), 4.68 (s, 3H), 1.91 (s, 3H), $^{13}$C-NMR (100 MHz) CDCl$_3$: 158.0, 146.2, 143.7, 137.8, 137.5, 129.4, 129.2, 126.8, 121.2, 118.8, 115.8, 115.6, 98.1, 63.8, 36.7, 12.8; LC/MS-MS: 347.1→281.1 m/z; GS1 and GS2 at 30, DP=11, CE=31, CXP=18, $t_R$=4.16 min.

6-amino-1,3-dimethyl-4-phenyl-1,4-dihydropyrano[2,3-c]pyrazole-5-carbonitrile UC-E12

A mixture of benzaldehyde (290 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 1,3-dimethyl-1H-pyrazol-5(4H)-one (322 mg, 2.87 mmol, 1 equiv.). The reaction mixture was concentrated after 19 h and washed with ethanol and hexanes. The crude material was purified by column chromatography on SiO$_2$ (25% ethyl acetate in n-hexanes to 100% ethyl acetate) and then re-crystallized from ethanol to give 6-amino-1,3-dimethyl-4-phenyl-1,4-dihydropyrano[2,3-c]pyrazole-5-carbonitril (263 mg, 0.988 mmol, 34%) as a yellow powder. $^1$H-NMR (400 MHz) DMSO: 7.34-7.32 (m, 2H), 7.25-7.23 (t, 1H), 7.19-7.17 (d, 2H), 7.05 (s, 2H), 4.57 (s, 1H), 3.60 (s, 3H), 1.66 (s, 3H), $^{13}$C-NMR (100 MHz) DMSO: 159.9, 144.6, 144.4, 142.9, 128.8, 128.0, 127.3, 120.6, 96.5, 58.7, 37.5, 33.8, 12.8; LC/MS-MS: 267.0→201.3 m/z; GS1 and GS2 at 30, DP=61, CE=29, CXP=12, $t_R$=3.74 min.

6-amino-1-methyl-3,4-diphenyl-1,4-dihydropyrano[2,3-c]pyrazole-5-carbonitrile UC-E13

A mixture consisting of benzaldehyde (290 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 1-methyl-3-phenyl-1H-pyrazol-5(4H)-one (500 mg, 2.87 mmol, 1 equ.). The reaction mixture was concentrated after 21 h and washed with ethanol and hexanes; re-crystallized from ethanol, and washed with hexanes and ethanol to give 6-amino-1-methyl-3,4-diphenyl-1,4-dihydropyrano[2,3-c]pyrazole-5-carbonitrile (282 mg, 8.58 mmol, 30%) as a white solid. $^1$H-NMR (400 MHz) DMSO: 7.41-7.38 (m, 2H), 7.28-7.24 (m, 2H), 7.21-7.18 (m, 6H), 4.88 (s, 1H), 4.77 (s, 2H), 3.83 (s, 3H), $^{13}$C-NMR (100 MHz) DMSO: 158.1, 146.0, 144.8, 144.6, 133.2, 128.7, 128.5, 127.9, 127.8, 127.1, 126.4, 120.5, 95.7, 59.9, 38.2, 34.5; LC/MS-MS: 329.1→263.1 m/z; GS1 and GS2 at 30, DP=71, CE=31, CXP=18, $t_R$=4.00 min.

6-amino-1,3,4-triphenyl-1,4-dihydropyrano[2,3-c]pyrazole-5-carbonitrile UC-E14

A mixture of benzaldehyde (290 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 1,3-diphenyl-1H-pyrazol-5(4H)-one (678 mg, 2.87 mmol, 1 equ.). The precipitate was filtered off and washed with ethanol and hexanes, and re-crystallized from ethanol to give 6-amino-1,3,4-triphenyl-1,4-dihydropyrano[2,3-c]pyrazole-5-carbonitrile (330 mg, 0.845 mmol, 29%) as a white solid. $^1$H-NMR (400 MHz) CDCl$_3$: 7.82-7.80 (d, 2H), 7.55-7.50 (m, 4H), 7.41-7.37 (t, 1H), 7.32-7.22 (m, 8H), 4.96 (s, 1H), 4.68 (s, 2H), $^{13}$C-NMR (100 MHz) CDCl$_3$: 157.5, 147.7, 144.9, 142.6, 137.5, 132.2, 129.3, 128.8, 128.2, 128.2, 127.5, 127.4, 127.1, 126.9, 121.6, 118.9, 97.5, 64.8, 38.2; LC/MS-MS: 391.1→325.0 m/z; GS1 and GS2 at 30, DP=91, CE=33, CXP=22, $t_R$=4.33 min.

6-amino-3-(4-methoxyphenyl)-1,4-diphenyl-1,4-dihydropyrano[2,3-c]pyrazole-5-carbonitrile UC-E15

A mixture of benzaldehyde (290 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 3-(4-methoxyphenyl)-1-phenyl-1H-pyrazol-5(4H)-one (764 mg, 2.87 mmol, 1 equ.). The reaction mixture was concentrated after 19 h and washed with ethanol and hexanes, re-crystallized from ethanol, and washed with hexanes and ethanol to give 6-amino-3-(4-methoxyphenyl)-1,4-diphenyl-1,4-dihydropyrano[2,3-c]pyrazole-5-carbonitrile (695 mg, 1.65 mmol, 58%) as a white solid. $^1$H-NMR (400 MHz) DMSO: 7.94-7.92 (d, 2H), 7.58-7.53 (m, 2H), 7.41-7.37 (t, 1H), 7.27-7.16 (m, 7H), 6.83-6.81 (d, 2H), 5.04 (s, 1H), 3.71 (s, 3H), $^{13}$C-NMR (100 MHz) DMSO: 159.5, 159.0, 146.6, 145.6, 144.5, 137.9, 129.8, 128.9, 128.3, 128.0, 127.3, 127.1, 125.1, 121.1, 120.3, 114.1, 97.5, 59.8, 55.5, 37.9; LC/MS-MS: 421.2→355.0 m/z; GS1 and GS2 at 30, DP=71, CE=33, CXP=24, $t_R$=4.28 min.

6-amino-3-(4-methoxyphenyl)-1-methyl-4-phenyl-1,4-dihydropyrano[2,3-c]pyrazole-5-carbonitrile UC-E16

A mixture of benzaldehyde (290 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 3-(4-methoxyphenyl)-1-methyl-1H-pyrazol-5(4H)-one (583 mg, 2.87 mmol, 1 equ.). The reaction mixture was concentrated after 24 h. The crude material was purified by column chromatography (25% ethyl acetate in hexanes to 100% ethyl acetate), then re-crystallized from ethanol and washed with hexanes and ethanol to give 6-amino-3-(4-methoxyphenyl)-1-methyl-4-phenyl-1,4-dihydropyrano[2,3-c]pyrazole-5-carbonitrile (80.9 mg, 8%, 0.226 mmol) as a yellow solid. $^1$H-NMR (400 MHz) DMSO: 7.42-7.40 (d, 2H), 7.23-7.21 (m, 2H), 7.15-7.13 (d, 3H), 7.06 (s, 1H), 6.77-6.75 (d, 2H), 4.93 (s, 1H), 3.76 (s, 3H), 3.69 (s, 3H), $^{13}$C-NMR (100 MHz) DMSO: 159.1, 159.0, 145.9, 144.8, 144.5, 128.8, 127.8, 127.7, 127.1, 125.8, 120.5, 113.9, 95.0, 59.9, 55.4, 38.2, 34.4; LC/MS-MS: 359.1→293.0 m/z; GS1 and GS2 at 30, DP=76, CE=31, CXP=20, $t_R$=3.96 min.

6-amino-3-(3,4-dimethoxyphenyl)-1-methyl-4-phenyl-1,4-dihydropyrano[2,3-c]pyrazole-5-carbonitrile UC-E17

A mixture of benzaldehyde (145 µL, 1.44 mmol, 1.0 equ.), malononitrile (90.0 mg, 1.44 mmol, 1.0 equ.) and triethylamine (200 µL, 1.44 mmol, 1.0 equ.) in ethanol (5.0 mL) was stirred for 1 min, followed by the addition of 3-(3,4- dimethoxyphenyl)-1-methyl-1H-pyrazol-5(4H)-one (336 mg, 1.44 mmol, 1 equ.). The reaction mixture was concentrated after 24 h. The crude material was purified by column chromatography. (25% ethyl acetate in hexanes to 100% ethyl acetate), then re-crystallized from ethanol and washed with hexanes and ethanol to give 6-amino-3-(3,4-dimethoxyphenyl)-1-methyl-4-phenyl-1,4-dihydropyrano[2,3-c]pyrazole-5-carbonitrile (48.5 mg, 9%, 0.124 mmol) as a yellow solid. $^1$H-NMR (400 MHz) CDCl$_3$: 7.29-7.28 (d, 2H), 7.23-7.21 (d, 2H), 7.00-6.98 (d, 1H), 6.88 (s, 1H), 6.72-6.70 (d, 2H), 4.84 (s, 1H), 4.75 (s, 2H), 3.82 (s, 6H), 3.60 (s, 3H), $^{13}$C-NMR (100 MHz) CDCl$_3$: 157.6, 148.7, 148.6, 146.1, 145.7, 143.1, 128.9, 127.5, 127.4, 125.6, 119.3, 119.3, 110.9, 109.7, 94.7, 64.4, 55.7, 55.6, 38.3, 34.1; LC/MS-MS: 389.1→323.0 m/z; GS1 and GS2 at 30, DP=66, CE=31, CXP=22, $t_R$=3.82 min.

6-amino-4-(4-fluorophenyl)-1,3-dimethyl-1,4-dihydropyrano[2,3-c]pyrazole-5-carbonitrile UC-E18

A mixture of 4-fluorobenzaldehyde (300 µL, 2.87 mmol, 1.0 equ.), malononitrile (190 mg, 2.87 mmol, 1.0 equ.) and triethylamine (400 mL, 2.87 mmol, 1.0 equ.) in ethanol (8.0 mL) was stirred for 1 min, followed by the addition of 1,3-dimethyl-1H-pyrazol-5(4H)-one (322 mg, 2.87 mmol, 1 equ.). The reaction mixture was concentrated after 24 h and washed with ethanol and hexanes, and re-crystallized from ethanol to give 6-amino-4-(4-fluorophenyl)-1,3-dimethyl-1,4-dihydropyrano[2,3-c]pyrazole-5-carbonitrile (335 mg, 41%, 1.17 mmol) as a white solid. $^1$H-NMR (400 MHz) DMSO: 7.23-7.20 (m, 2H), 7.16-7.12 (m, 2H), 7.07 (s, 2H), 4.61 (s, 1H), 3.60 (s, 3H), 1.67 (s, 3H), $^{13}$C-NMR (100 MHz) DMSO: 162.7, 159.9, 144.6, 142.9, 140.7, 129.9, 120.6, 115.6, 115.4, 96.3, 59.6, 56.4, 36.7, 33.8, 12.8; LC/MS-MS: 285.1→219.1 m/z; GS1 and GS2 at 30, DP=61, CE=27, CXP=14, $t_R$=3.80 min.

6-amino-4-(4-fluorophenyl)-1-methyl-3-phenyl-1,4-dihydropyrano[2,3-c]pyrazole-5-carbonitrile UC-E19

A mixture of the 4-fluorobenzaldehyde (300 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 1-methyl-3-phenyl-1H-pyrazol-5(4H)-one (500 mg, 2.87 mmol, 1 equ.). The reaction mixture was concentrated after 20 h in vacuo and washed with ethanol and hexanes, and re-crystallized from ethanol to give 6-amino-4-(4-fluorophenyl)-1-methyl-3-phenyl-1,4-dihydropyrano[2,3-c]pyrazole-5-carbonitrile (182 mg, 0.525 mmol, 18%) as a light yellow solid. $^1$H-NMR (400 MHz) DMSO: 7.50-7.48 (d, 2H), 7.22-7.18 (m, 5H), 7.11 (s, 2H), 7.05-6.98 (t, 2H) 5.04 (s, 1H), 3.78 (s, 3H), $^{13}$C-NMR (100 MHz) DMSO: 162.5, 159.1, 146.0, 144.6, 140.9, 133.1, 129.8, 128.5, 127.9, 126.5, 120.4, 115.5, 115.3, 95.5, 59.7, 37.4, 34.5; LC/MS-MS: 347.1→281.0 m/z; GS1 and GS2 at 30, DP=66, CE=31, CXP=14, $t_R$=4.00 min.

6-amino-4-(4-fluorophenyl)-1,3-diphenyl-1,4-dihydropyrano[2,3-c]pyrazole-5-carbonitrile UC-E20

A mixture of 4-fluorobenzaldehyde (300 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 1,3-diphenyl-1H-pyrazol-5(4H)-one (678 mg, 2.87 mmol, 1 equ.). The precipitate formed was filtered out and washed with ethanol and hexanes, and re-crystallized from ethanol to afford 6-amino-4-(4-fluorophenyl)-1,3-diphenyl-1,4-dihydropyrano[2,3-c]pyrazole-5-carbonitrile (240 mg, 0.588 mmol, 20%) as a white powder. $^1$H-NMR (400 MHz) DMSO: 7.94-7.92 (d, 2H), 7.61-7.55 (m, 4H), 7.42-7.38 (t, 1H), 7.28-7.24 (m, 7H), 7.06-7.02 (t, 2H), 5.15 (s, 1H), $^{13}$C-NMR (100 MHz) DMSO: 162.6, 159.0, 146.8, 145.6, 140.6, 137.8, 132.5, 130.0, 129.9, 129.8, 128.6, 128.6, 127.3, 127.0, 121.3, 120.2, 115.6, 115.4, 97.9, 59.6, 37.0; LC/MS-MS: 410.4→242.2 m/z; GS1 and GS2 at 30, DP=21, CE=47, CXP=16, $t_R$=4.63 min.

6-amino-3-(3,4-dimethoxyphenyl)-4-(4-fluorophenyl)-1-methyl-1,4-dihydropyrano[2,3-c]pyrazole-5-carbonitrile, UC-E21

A mixture of 4-fluorobenzaldehyde (300 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 3-(3,4-dimethoxyphenyl)-1-methyl-1H-pyrazol-5(4H)-one (672 mg, 2.87 mmol, 1 equ.). The precipitate formed was filtered out and washed with ethanol and hexanes, and re-crystallized from ethanol to give 6-amino-3-(3,4-dimethoxyphenyl)-4-(4-fluorophenyl)-1-methyl-1,4-dihydropyrano[2,3-c]pyrazole-5-carbonitrile (782 mg, 1.93 mmol, 67%) as a white powder. $^1$H-NMR (400 MHz) DMSO: 7.20-7.18 (m, 2H), 7.09-7.03 (m, 5H), 6.96-6.95 (d, 1H), 6.80-6.78 (d, 2H), 5.02 (s, 1H), 3.77 (s, 3H), 3.69 (s, 3H), 3.62 (s, 3H)$^{13}$C-NMR (100 MHz) DMSO: 162.6, 159.0, 148.7, 146.0, 144.6, 141.0, 141.0, 129.8, 129.7, 125.9, 120.4, 119.0, 115.7, 115.4, 111.8, 109.8, 94.7, 55.8, 55.7, 37.3, 34.4; LC/MS-MS: 407.1→341.1 m/z; GS1 and GS2 at 30, DP=71, CE=33, CXP=22, $t_R$=3.86 min.

6-amino-4-(4-fluorophenyl)-3-(4-methoxyphenyl)-1-phenyl-1,4-dihydropyrano[2,3-c]pyrazole-5-carbonitrile UC-E22

A mixture of 4-fluorobenzaldehyde (300 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 3-(4-methoxyphenyl)-1-phenyl-1H-pyrazol-5(4H)-one (764 mg, 2.87 mmol, 1 equ.). The precipitate formed was filtered off and washed with ethanol and hexanes, and re-crystallized from ethanol to afford 6-amino-4-(4-fluorophenyl)-3-(4-methoxyphenyl)-1-phenyl-1,4-dihydropyrano[2,3-c]pyrazole-5-carbonitrile (800 mg, 1.83 mmol, 64%) as white solid. $^1$H-NMR (400 MHz) DMSO: 7.93-7.91 (d, 2H), 7.55-7.53 (m, 4H), 7.41-7.37 (t, 1H), 7.26-7.23 (m, 4H), 7.07-7.05 (t, 2H), 6.84-6.82 (d, 2H), 5.11 (s, 1H), 3.72 (s, 3H)$^{13}$C-NMR (100 MHz) DMSO: 162.6, 159.6, 159.0, 146.6, 145.5, 140.7, 140.6, 137.9, 130.0, 129.9, 129.8, 128.3, 127.1, 125.0, 121.1, 120.2, 115.6, 115.4, 114.1, 97.3, 59.6, 55.5, 37.0; LC/MS-MS: 439.2→373.0 m/z; GS1 and GS2 at 30, DP=61, CE=35, CXP=24, $t_R$=4.28 min.

6-amino-3-(3,4-dimethoxyphenyl)-4-(4-fluorophenyl)-1-phenyl-1,4-dihydropyrano[2,3-c]pyrazole-5-carbonitrile UC-E23

A mixture of 4-fluorobenzaldehyde (70.0 µL, 0.675 mmol, 1.0 equ.), malononitrile (45.0 mg, 0.675 mmol, 1.0 equ.) and triethylamine (90.0 µL, 0.675 mmol, 1.0 equ.) in ethanol (3.0 mL) was stirred for 1 min, followed by the addition of the 3-(3,4-dimethoxyphenyl)-1-phenyl-1H-pyrazol-5(4H)-one (200 mg, 0.675 mmol, 1 equ.). The reaction mixture was concentrated after 19 h and the crude material was purified by column chromatography (25% ethyl acetate in hexanes to 100% ethyl acetate). The yellow solid was further purified by re-crystallization from ethanol to give 6-amino-3-(3,4-dimethoxyphenyl)-4-(4-fluorophenyl)-1-phenyl-1,4-dihydropyrano[2,3-c]pyrazole-5-carbonitrile (164 mg, 0.350 mmol, 12%) as a white solid. $^1$H-NMR (400 MHz) CDCl$_3$: 7.80-7.78 (d, 2H), 7.52-7.48 (t, 2H), 7.38-7.35 (t, 1H), 7.25-7.21 (m, 2H), 7.05-6.95 (m, 4H), 6.75-6.73 (d, 1H), 4.91 (s, 1H), 4.84 (s, 1H), 3.84 (s, 3H), 3.71 (s, 3H), $^{13}$C-NMR (100 MHz) CDCl$_3$: 163.2, 157.8, 149.2, 148.7, 147.5, 144.9, 138.6, 137.4, 129.3, 129.1, 129.0, 127.1, 125.0, 121.5, 119.8, 119.0, 115.9, 115.7, 110.8, 109.9, 96.6, 64.0, 55.8, 55.7, 37.5; LC/MS-MS: 469.3→403.1 m/z; GS1 and GS2 at 30, DP=6, CE=35, CXP=26, $t_R$=4.16 min.

6-amino-4-(4-fluorophenyl)-3-(4-methoxyphenyl)-1-methyl-1,4-dihydropyrano[2,3-c]pyrazole-5-carbonitrile UC-E24

A mixture of 4-fluorobenzaldehyde (300 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 3-(4-methoxyphenyl)-1-methyl-1H-pyrazol-5(4H)-one (586 mg, 2.87 mmol, 1 equ.). The reaction mixture was concentrated after 19 h and the precipitate formed was washed with ethanol and hexanes, re-crystallized from ethanol, and washed with hexanes and ethanol to give 6-amino-4-(4-fluorophenyl)-3-(4-methoxyphenyl)-1-methyl-1,4-dihydropyrano[2,3-c]pyrazole-5-carbonitrile (350 mg, 0.930 mmol, 32%) as a white solid. $^1$H-NMR (400 MHz) DMSO: 7.43-7.40 (d, 2H), 7.20-7.16 (m, 2H), 7.10 (s, 2H), 7.06-7.02 (t, 2H), 6.78-6.76 (d, 2H), 4.99 (s, 1H), 3.75 (s, 3H), 3.69 (s, 3H), $^{13}$C-NMR (100 MHz) DMSO: 162.5, 159.1, 145.8, 144.6, 141.0, 141.0, 129.8, 129.7, 127.8, 125.7, 120.5, 115.6, 115.4, 113.9, 94.9, 59.7, 55.4, 37.4, 34.4; LC/MS-MS: 377.1→311.1 m/z; GS1 and GS2 at 30, DP=66, CE=33, CXP=20, $t_R$=3.98 min.

6-amino-4-(4-methoxyphenyl)-3-methyl-1-phenyl-1,4-dihydropyrano[2,3-c]pyrazole-5-carbonitrile UC-E25

A mixture of anisaldehyde (350 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 6-amino-4-(4-methoxyphenyl)-3-methyl-1-phenyl-1,4-dihydropyrano[2,3-c]pyrazole-5-carbonitrile (500 mg, 2.87 mmol, 1 equ.). The reaction mixture was concentrated after 24 h and the precipitate was washed with ethanol and hexanes, and re-crystallized from ethanol to give 6-amino-4-(4-methoxyphenyl)-3-methyl-1-phenyl-1,4-dihydropyrano[2,3-c]pyrazole-5-carbonitrile (800 mg, 78%, 2.23 mmol) as a white solid. $^1$H-NMR (400 MHz) DMSO: 7.80-7.78 (d, 2H), 7.51-7.47 (t, 2H), 7.32-7.28 (t, 1H), 7.18-7.16 (m, 4H), 6.91-6.89 (d, 2H), 4.62 (s, 1H), 3.74 (s, 3H), 1.79 (s, 3H), $^{13}$C-NMR (100 MHz) DMSO: 159.7, 158.6, 145.7, 144.2, 138.0, 136.0, 129.7, 129.2, 126.5, 120.5, 120.3, 114.3, 99.3, 59.0, 55.4, 36.4, 13.0; LC/MS-MS: 359.2→293.0 m/z; GS1 and GS2 at 30, DP=71, CE=29, CXP=20, $t_R$=4.14 min.

6-amino-4-(4-methoxyphenyl)-1,3-dimethyl-1,4-dihydropyrano[2,3-c]pyrazole-5-carbonitrile UC-E26

A mixture of anisaldehyde (350 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 1,3-dimethyl-1H-pyrazol-5(4H)-one (321 mg, 2.87 mmol, 1 equ.). The reaction mixture was concentrated after 24 h and the crude material was purified by column chromatography (25% ethyl acetate in hexanes to 100% ethyl acetate). The yellow solid was washed with ethanol and hexanes, and re-crystallized from ethanol to give 6-amino-4-(4-methoxyphenyl)-1,3-dimethyl-1,4-dihydropyrano[2,3-c]pyrazole-5-carbonitrile (370 mg, 1.25 mmol, 44%) as a white solid. $^1$H-NMR (400 MHz) CDCl$_3$: 7.12-7.10 (d, 2H), 6.85-6.83 (d, 2H), 4.61 (s, 2H), 4.55 (s, 1H), 3.79 (s, 3H), 3.69 (s, 3H), 1.80 (s, 3H)$^{13}$C-NMR (100 MHz) CDCl$_3$: 158.8, 157.9, 144.5, 144.4, 134.5, 128.8, 119.3, 114.0, 96.4, 64.2, 55.2, 36.7, 33.7, 12.7; LC/MS-MS: 297.0→231.2 m/z; GS1 and GS2 at 30, DP=61, CE=27, CXP=16, $t_R$=3.71 min.

6-amino-4-(4-methoxyphenyl)-1-methyl-3-phenyl-1,4-dihydropyrano[2,3-c]pyrazole-5-carbonitrile UC-E27

A mixture of anisaldehyde (350 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 1-methyl-3-phenyl-1H-pyrazol-5(4H)-one (500 mg, 2.87 mmol, 1 equ.). The reaction mixture was concentrated after 24 h and the precipitate was washed with ethanol and hexanes, and product re-crystallized from ethanol to give 6-amino-4-(4-methoxyphenyl)-1-methyl-3-phenyl-1,4-dihydropyrano[2,3-c]pyrazole-5-carbonitrile (210 mg, 20%, 0.586 mmol) as a white solid. $^1$H-NMR (400 MHz) DMSO: 7.50-7.48 (d, 2H), 7.21-7.17 (m, 3H), 7.05-7.02 (m, 4H), 6.76-6.74 (d, 2H), 4.91 (s, 1H), 3.76 (s, 3H), 3.64 (s, 3H), $^{13}$C-NMR (100 MHz) DMSO: 158.9, 158.3, 146.0, 144.6, 136.9, 133.2, 128.9, 128.5, 127.8, 126.4, 120.6, 114.1, 95.9, 60.3, 55.3, 37.5, 34.5; LC/MS-MS: 359.2→293.0 m/z; GS1 and GS2 at 30, DP=66, CE=29, CXP=20, $t_R$=3.98 min.

6-amino-4-(4-methoxyphenyl)-1-methyl-3-phenyl-1,4-dihydropyrano[2,3-c]pyrazole-5-carbonitrile UC-E28

A mixture of anisaldehyde (350 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) is stirred for 1 min, followed by the addition of 1,3-diphenyl-1H-pyrazol-5(4H)-one (678 mg, 2.87 mmol, 1 equ.). The reaction mixture was concentrated after 24 h and the precipitate was washed with ethanol and hexanes. The product was re-crystallized from ethanol to afford 6-amino-4-(4-methoxyphenyl)-1-methyl-3-phenyl-1,4-dihydropyrano[2,3-c]pyrazole-5-carbonitrile (1.05 g, 87%, 2.50 mmol) as a white solid. $^1$H-NMR (400 MHz) DMSO: 7.94-7.92 (d, 2H), 7.63-7.61 (d, 2H), 7.57-7.53 (t, 2H), 7.40-7.36 (t, 1H), 7.29-7.23 (m, 3H) 7.15 (s, 2H), 7.13-7.11 (d, 2H), 6.78-6.76 (d, 2H), 5.02 (s, 1H), 3.65 (s, 3H), $^{13}$C-NMR (100 MHz) DMSO: 158.9, 158.4, 146.7, 145.6, 137.9, 136.5, 132.6, 129.8, 129.0, 128.7, 128.5, 127.2, 127.0, 121.2, 120.3, 114.2, 98.3, 60.2, 55.3, 37.1; LC/MS-MS: 421.2→355.0 m/z; GS1 and GS2 at 30, DP=81, CE=35, CXP=24, $t_R$=4.32 min.

6-amino-3,4-bis(4-methoxyphenyl)-1-phenyl-1,4-dihydropyrano[2,3-c]pyrazole-5-carbonitrile UC-E29

A mixture of anisaldehyde (350 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 3-(4-methoxyphenyl)-1-phenyl-1H-pyrazol-5(4H)-one (764 mg, 2.87 mmol, 1 equ.). The reaction mixture was concentrated after 24 h and the precipitate was washed with ethanol and hexanes, and then re-crystallized from ethanol to give 6-amino-3,4-bis(4-methoxyphenyl)-1-phenyl-1,4-dihydropyrano[2,3-c]pyrazole-5-carbonitrile (1.06 g, 2.35 mmol, 82%) as a white solid. $^1$H-NMR (400 MHz) DMSO: 7.93-7.91 (d, 2H), 7.56-7.52 (m, 4H), 7.38-7.35 (t, 1H), 7.15-7.11 (m, 4H), 6.83-6.78 (m, 4H), 4.98 (s, 1H), 3.70 (s, 3H), 3.66 (s, 3H), $^{13}$C-NMR (100 MHz) DMSO: 159.5, 158.9, 158.4, 146.6, 145.5, 137.9, 136.6, 129.8, 129.0, 128.3, 127.0, 125.2, 121.0, 120.4, 114.2, 114.1, 97.7, 60.3, 55.5, 55.3, 37.1; LC/MS-MS: 452.3→89.1 m/z; GS1 and GS2 at 30, DP=36, CE=39, CXP=4, $t_R$=3.47 min.

6-amino-3,4-bis(4-methoxyphenyl)-1-methyl-1,4-dihydropyrano[2,3-c]pyrazole-5-carbonitrile UC-E30

A mixture of anisaldehyde (350 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 3-(4-methoxyphenyl)-1-methyl-1H-pyrazol-5(4H)-one (689 mg, 2.87 mmol, 1 equiv.). The reaction mixture was concentrated after 24 h and the precipitate was washed with ethanol and hexanes, and then re-crystallized from ethanol to give 6-amino-3,4-bis(4-methoxyphenyl)-1-methyl-1,4-dihydropyrano[2,3-c]pyrazole-5-carbonitrile (690 mg, 1.78 mmol, 62%) as a white solid. $^1$H-NMR (400 MHz) DMSO: 7.42-7.40 (d, 2H), 7.05-7.03 (d, 2H), 7.00 (s, 2H), 6.78-6.75 (dd, 4H), 4.86 (s, 1H), 3.73 (s, 3H), 3.68 (s, 3H), 3.66 (s, 3H), $^{13}$C-NMR (100 MHz) DMSO: 159.0, 158.9, 158.3, 145.9, 144.5, 136.9, 128.9, 127.7, 125.9, 120.6, 114.1, 113.9, 95.3, 60.3, 55.4, 55.3, 37.5, 34.3; LC/MS-MS: 389.2→323.0 m/z; GS1 and GS2 at 30, DP=66, CE=29, CXP=22, $t_R$=3.94 min.

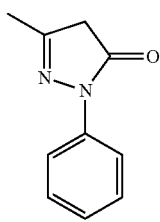

Chemical Formula: $C_{10}H_{10}N_2O$
Molecular Weight: 174.20

General Procedure A; 3-methyl-1-phenyl-1H-pyrazol-5(4H)-one

A solution of ethyl acetoacetate (9.02 mL, 71.2 mmol, 1.1 equ.) in ethanol (130 mL) was treated at 0° C. with phenylhydrazine (7.00 g, 64.7 mmol, 1.0 equ.). The mixture was allowed to come to slowly ward to ambient temperature and then heated to 60° C. (3 h). The solvent was removed under vacuum and the residue purified by column chromatography on silica gel (ethyl acetate:hexanes; 1:1) to give 3-methyl-1-phenyl-1H-pyrazol-5(4H)-one (7.60 g, 43.6 mmol, 67%) as a light yellow powder. $^1$H-NMR (400 MHz) CDCl$_3$: 7.87-7.85 (d, 2H), 7.41-7.37 (t, 2H), 7.19-7.16 (t, 1H), 3.42 (s, 2H), 2.19 (s, 3H), $^{13}$C-NMR (100 MHz) CDCl$_3$: 170.5, 156.2, 138.0, 128.8, 125.0, 118.8, 43.0, 17.0; LC/MS-MS: 175.0→77.1 m/z; GS1 and GS2 at 30, DP=56, CE=25, CXP=4, $t_R$=3.52 min.

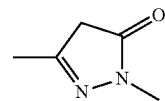

Chemical Formula: $C_5H_8N_2O$
Molecular Weight: 112.13

1,3-dimethyl-1H-pyrazol-5(4H)-one

Following the 'general procedure A'; ethyl acetoacetate (15.1 mL, 119 mmol, 1.1 equ.) in ethanol (200 mL) was treated at 0° C. with methylhydrazine (5.00 g, 109 mmol, 1.0 equ.) to afford 1,3-dimethyl-1H-pyrazol-5(4H)-one (8.02 g, 71.5 mmol, 66%) after purification by crystallization (DCM and n-hexanes) as a white off solid. $^1$H-NMR (400 MHz) CDCl$_3$: 3.25 (s, 3H), 3.16 (s, 2H), 2.08 (s, 3H), $^{13}$C-NMR (100 MHz) CDCl$_3$: 172.2, 155.4, 138.0, 41.3, 31.0, 16.8.

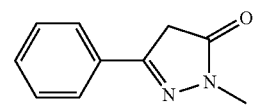

Chemical Formula: $C_{10}H_{10}N_2O$
Molecular Weight: 174.20

1-methyl-3-phenyl-1H-pyrazol-5(4H)-one

According to General Procedure A; ethyl benzoylacetate (18.4 mL, 95.5 mmol, 1.1 equ.) in ethanol (180 mL) was treated at 0° C. with methylhydrazine (4.57 mL, 86.8 mmol, 1.0 equ.) to give 1-methyl-3-phenyl-1H-pyrazol-5(4H)-one (11.0 g 63.1 mmol, 73%) after purification by crystallization (ethanol) as a light yellow solid. $^1$H-NMR (400 MHz) CDCl$_3$: 7.67-7.65 (m, 2H), 7.42-7.41 (m, 3H), 3.60 (s, 2H), 3.41 (s, 3H), $^{13}$C-NMR (100 MHz) CDCl$_3$: 171.8, 154.2, 131.0, 130.3, 128.8, 125.6, 37.9, 31.4. LC/MS-MS: 175.0→77.2 m/z; GS1 and GS2 at 30, DP=66, CE=43, CXP=4, $t_R$=3.45 min.

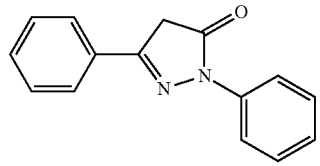 [SMILES: O=C1CC(c2ccccc2)=NN1c1ccccc1]

Chemical Formula: $C_{15}H_{12}N_2O$
Molecular Weight: 236.27

1,3-diphenyl-1H-pyrazol-5(4H)-one

According to General Procedure A; ethyl benzoylacetate (12.2 mL, 71.2 mmol, 1.1 equ.) in ethanol (130 mL) was treated at 0° C. with phenylhydrazine (7.00 g, 71.2 mmol, 1.0 equ.) to give 1,3-diphenyl-1H-pyrazol-5(4H)-one (6.75 g, 28.6 mmol, 44%) after purification by column chromatography on silica gel (hexanes:ethyl acetate; 4:1) and crystallization (ethanol) as a white off solid. ¹H-NMR (400 MHz) DMSO: 11.84 (s, 1H), 7.84-7.82 (d, 4H), 7.50-7.40 (m, 4H), 7.34-7.27 (m, 2H), 6.02 (s, 1H), ¹³C-NMR (100 MHz) DMSO: 154.2, 150.0, 139.3, 133.8, 129.3, 129.0, 128.2, 126.1, 125.5, 121.5, 85.5; LC/MS-MS: 237.0→77.1 m/z; GS1 and GS2 at 30, DP=81, CE=68, CXP=4, $t_R$=4.15 min.

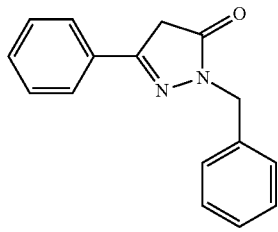 [SMILES: O=C1CC(c2ccccc2)=NN1Cc1ccccc1]

Chemical Formula: $C_{16}H_{14}N_2O$
Molecular Weight: 250.30

1-benzyl-3-phenyl-1H-pyrazol-5(4H)-one

A solution of ethyl benzoylacetate (4.80 mL, 28.2 mmol, 1.1 equ.) in ethanol (60 mL) was treated at 0° C. with benzlhydrazine (5.00 g, 25.6 mmol, 1.0 equ.). The mixture was slowly warmed to ambient temperature and heated to 60° C. (16 h). The reaction mixture was concentrated and diluted with ethanol (100 mL) and then 3.0 g of sodium ethoxide added and stirred (40 h). The solid was filtered off and the solvent removed in vacuo. The residue was purified by column chromatography on silica gel (4:1 n-hexanes: ethyl acetate to 100% ethyl acetate) to give 1-benzyl-3-phenyl-1H-pyrazol-5(4H)-one (0.255 g, 1.02 mmol, 4%) as a light orange solid. ¹H-NMR (400 MHz) DMSO: 11.17 (s, 1H), 7.71-7.70 (d, 2H), 7.37-7.31 (m, 4H), 7.27-7.20 (m, 4H), 5.85 (s, 1H), 5.13 (s, 2H), ¹³C-NMR (100 MHz) DMSO: 153.6, 148.6, 138.3, 134.4, 128.8, 128.8, 127.6, 127.6, 125.1, 83.7, 50.0; LC/MS-MS: 251.1→91.1 m/z; GS1 and GS2 at 30, DP=2, CE=33, CXP=14, $t_R$=4.01 min.

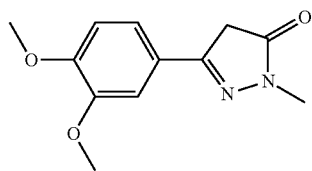

Chemical Formula: $C_{12}H_{14}N_2O$
Molecular Weight: 234.25

3-(3,4-dimethoxyphenyl)-1-methyl-1H-pyrazol-5(4H)-one

Using General Procedure A; ethyl 3,4-dimethoxybenzoylacetate (5.00 g, 19.8 mmol, 1.1 equ.) in ethanol (60 mL) was treated at 0° C. with methylhydrazine (0.95 mL, 19.8 mmol, 1.0 equiv.) to give 3-(3,4-dimethoxyphenyl)-1-methyl-1H-pyrazol-5(4H)-one (1.86 g, 7.94 mmol, 44%) after purification by chromatography on silica gel (hexanes: ethyl acetate; 4:1 to 1:1) as a light yellow powder. ¹H-NMR (400 MHz) CDCl₃: 7.35-7.35 (d, 1H), 7.06-7.04 (dd, 1H), 6.87-6.85 (d, 1H), 3.94 (s, 3H), 3.92 (s, 3H), 3.57 (s, 2H), 3.39 (s, 3H), ¹³C-NMR (100 MHz) CDCl₃: 171.6, 154.1, 151.1, 149.4, 124.1, 119.6, 110.7, 107.3, 55.9, 55.9, 38.0, 31.3; LC/MS-MS: 235.1→219.0 m/z; GS1 and GS2 at 30, DP=66, CE=33, CXP=14, $t_R$=3.26 min.

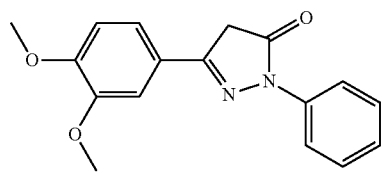 [SMILES: COc1ccc(C2=NN(c3ccccc3)C(=O)C2)cc1OC]

Chemical Formula: $C_{17}H_{16}N_2O_3$
Molecular Weight: 296.32

3-(3,4-dimethoxyphenyl)-1-phenyl-1H-pyrazol-5(4H)-one

Using General Procedure A; ethyl 3,4-dimethoxybenzoylacetate (3.00 g, 11.9 mmol, 1.1 equ.) in ethanol (60 mL) was treated at 0° C. with phenylhydrazine (1.17 mL, 10.8 mmol, 1.0 equ.) to afford 3-(3,4-dimethoxyphenyl)-1-phenyl-1H-pyrazol-5(4H)-one (920 mg, 2.32 mmol, 22%) after purification by crystallization (ethanol) as a yellow powder. ¹H-NMR (400 MHz) CDCl₃: 8.00-7.97 (d, 1H), 7.48-7.42 (m, 3H), 7.25-7.21 (t, 1H), 7.17-7.14 (dd, 1H), 6.91-6.89 (d, 1H), 3.98 (s, 3H), 3.95 (s, 3H), 3.83 (s, 2H), ¹³C-NMR (100 MHz) CDCl₃: 170.1, 154.4, 151.4, 149.4, 138.1, 128.8, 125.2, 123.8, 120.1, 119.1, 110.7, 107.6, 56.0, 56.0, 39.7; LC/MS-MS: 297.0→218.2 m/z; GS1 and GS2 at 30, DP=96, CE=37, CXP=18, $t_R$=3.98 min.

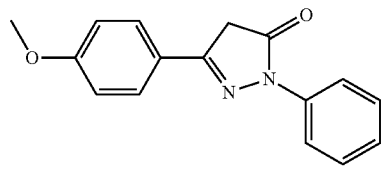 [SMILES: COc1ccc(C2=NN(c3ccccc3)C(=O)C2)cc1]

Chemical Formula: $C_{16}H_{14}N_2O_2$
Molecular Weight: 266.29

3-(4-methoxyphenyl)-1-phenyl-1H-pyrazol-5(4H)-one

Using General Procedure A; ethyl-4-methoxybenzoylacetate (7.00 g, 27.8 mmol, 1.1 equ.) in ethanol (100 mL) was treated at 0° C. with phenylhydrazine (2.50 mL, 25.3 mmol, 1.0 equ.) to give 3-(4-methoxyphenyl)-1-phenyl-1H-pyrazol-5(4H)-one (5.21 g, 19.6 mmol, 78%) after crystallization (ethanol) as a light yellow solid. ¹H-NMR (400 MHz) CDCl₃: 7.99-7.97 (d, 1H), 7.66-7.64 (d, 2H), 7.44-7.40 (t, 2H), 7.22-7.18 (t, 1H), 6.94-6.92 (d, 2H), 3.82 (s, 3H), 3.68 (s, 3H), ¹³C-NMR (100 MHz) CDCl₃: 170.1, 161.5, 154.4, 138.2, 128.8, 127.5, 125.0, 123.5, 118.8, 114.2, 55.3, 39.6; LC/MS-MS: 267.0→77.2 m/z; GS1 and GS2 at 30, DP=81, CE=65, CXP=4, $t_R$=4.15 min.

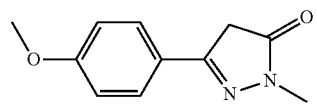

Chemical Formula: $C_{11}H_{12}N_2O_2$
Molecular Weight: 204.23

3-(4-methoxyphenyl)-1-methyl-1H-pyrazol-5(4H)-one

Using General Procedure A; ethyl-4-methoxybenzoylacetate (7.00 g, 27.8 mmol, 1.1 equ.) in ethanol (100 mL) was treated at 0° C. with methylhydrazine (1.30 mL, 25.2 mmol, 1.0 equ.) to give 3-(4-methoxyphenyl)-1-methyl-1H-pyrazol-5(4H)-one (3.00 g, 14.7 mmol, 58%) after crystallization from ethanol as a light yellow solid. $^1$H-NMR (400 MHz) DMSO: 10.94 (s, 1H), 7.63-7.60 (d, 2H), 6.92-6.90 (d, 2H), 5.70 (s, 1H), 3.76 (s, 3H), 3.54 (s, 3H), $^{13}$C-NMR (100 MHz) CDCl$_3$: 161.1, 153.4, 147.9, 126.3, 114.6, 114.4, 83.1, 59.7, 31.3; LC/MS-MS: 205.0→190.1 m/z; GS1 and GS2 at 30, DP=51, CE=29, CXP=12, $t_R$=3.44 min.

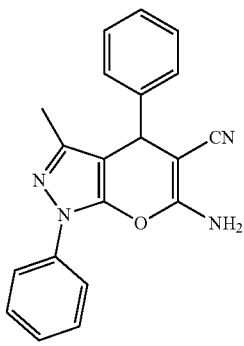 [SMILES: Cc1nn(-c2ccccc2)c2c1C(c1ccccc1)C(C#N)=C(N)O2]

Chemical Formula: C$_{20}$H$_{16}$N$_4$O
Molecular Weight: 328.37

6-amino-3-methyl-1,4-diphenyl-1,4-dihydropyrano[2,3-c]pyrazole-5-carbonitrile To a stirred solution of benzaldehyde (290 µL, 2.87 mmol), malononitrile (190 mg, 2.87 mmol) and 3-methyl-1-phenyl-1H-pyrazol-5(4H)-one (500 mg, 2.87 mmol) in anhydrous DCM (60 mL) was added anhydrous Na$_2$SO$_4$ (407 mg, 2.87 mmol) and ethylhydrocupreine hydrochloride (46 mg, 0.122 mmol). The reaction mixture was stirred at room temperature (25 h). After filtration and washing with DCM, the solvent was removed under reduced pressure. The crude mixture was subjected to flash column chromatography over silica gel (hexanes:ethyl acetate; 1:1) to give 6-amino-3-methyl-1,4-diphenyl-1,4-dihydropyrano[2,3-c]pyrazole-5-carbonitrile (270 mg, 0.822 mmol, 29%) as white solid. $^1$H-NMR (400 MHz) CDCl$_3$: 7.69-7.66 (d, 2H), 7.50-7.46 (t, 2H), 7.39-7.26 (m, 6H), 4.68 (s, 1H), 4.67 (s, 2H), 1.91 (s, 3H), $^{13}$C-NMR (100 MHz) CDCl$_3$: 158.1, 146.4, 143.8, 141.9, 137.5, 129.2, 128.8, 127.8, 127.5, 126.7, 121.2, 119.0, 98.3, 64.0, 37.4, 12.8; LC/MS-MS: 329.1→263.1 m/z; GS1 and GS2 at 30, DP=56, CE=31, CXP=18, $t_R$=4.18 min.

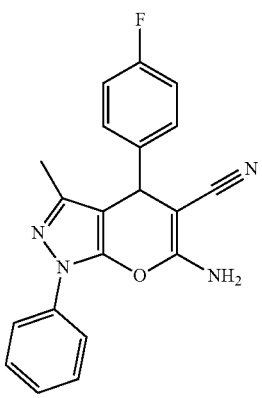 [SMILES: Cc1nn(-c2ccccc2)c2c1C(c1ccc(F)cc1)C(C#N)=C(N)O2]

Chemical Formula: C$_{20}$H$_{15}$FN$_4$O
Molecular Weight: 346.36

6-amino-4-(4-fluorophenyl)-3-methyl-1-phenyl-1,4-dihydropyrano[2,3-c]pyrazole-5-carbonitrile A mixture of the 4-fluourobenzaldehyde (356 mg, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of the 3-methyl-1-phenyl-1H-pyrazol-5(4H)-one (500 mg, 2.87 mmol, 1 equ.). The reaction mixture was concentrated and the precipitate filtered and re-crystallized from ethanol to give 6-amino-4-(4-fluorophenyl)-3-methyl-1-phenyl-1,4-dihydropyrano[2,3-c]pyrazole-5-carbonitrile (85.0 mg, 0.245 mmol, 9%) as a white solid. $^1$H-NMR (400 MHz) CDCl$_3$: 7.68-7.66 (d, 2H), 7.50-7.46 (t, 2H), 7.34-7.32 (t, 1H), 7.28-7.22 (m, 2H) 7.08-7.04 (t, 2H), 4.68 (s, 3H), 1.91 (s, 3H), $^{13}$C-NMR (100 MHz) CDCl$_3$: 158.0, 146.2, 143.7, 137.8, 137.5, 129.4, 129.2, 126.8, 121.2, 118.8, 115.8, 115.6, 98.1, 63.8, 36.7, 12.8; LC/MS-MS: 347.1→281.1 m/z; GS1 and GS2 at 30, DP=11, CE=31, CXP=18, $t_R$=4.16 min.

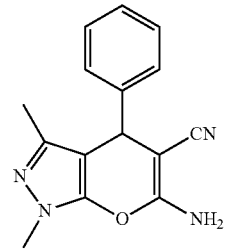 [SMILES: Cc1nn(C)c2c1C(c1ccccc1)C(C#N)=C(N)O2]

Chemical Formula: C$_{15}$H$_{14}$N$_4$O
Molecular Weight: 266.30

6-amino-1,3-dimethyl-4-phenyl-1,4-dihydropyrano[2,3-c]pyrazole-5-carbonitrile A mixture of benzaldehyde (290 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 1,3-dimethyl-1H-pyrazol-5(4H)-one (322 mg, 2.87 mmol, 1 equiv.). The reaction mixture was concentrated after 19 h and washed with ethanol and hexanes. The crude material was purified by column chromatography on SiO$_2$ (25% ethyl acetate in n-hexanes to 100% ethyl acetate) and then re-crystallized from ethanol to give 6-amino-1,3-dimethyl-4-phenyl-1,4-dihydropyrano[2,3-c]pyrazole-5-carbonitril (263 mg, 0.988 mmol, 34%) as a yellow powder. $^1$H-NMR (400 MHz) DMSO: 7.34-7.32 (m, 2H), 7.25-7.23 (t, 1H), 7.19-7.17 (d, 2H), 7.05 (s, 2H), 4.57 (s, 1H), 3.60 (s, 3H), 1.66 (s, 3H), $^{13}$C-NMR (100 MHz) DMSO: 159.9, 144.6, 144.4, 142.9, 128.8, 128.0, 127.3, 120.6, 96.5, 58.7, 37.5, 33.8, 12.8; LC/MS-MS: 267.0→201.3 m/z; GS1 and GS2 at 30, DP=61, CE=29, CXP=12, $t_R$=3.74 min.

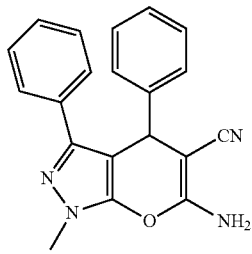 [SMILES: Cn1nc(-c2ccccc2)c2c1OC(N)=C(C#N)C2c1ccccc1]

Chemical Formula: $C_{20}H_{16}N_4O$
Molecular Weight: 328.37

6-amino-1-methyl-3,4-diphenyl-1,4-dihydropyrano [2,3-c]pyrazole-5-carbonitrile

A mixture consisting of benzaldehyde (290 μL, 2.87 mmol, 1.0 equ.), malononitrile (190 mg, 2.87 mmol, 1.0 equ.) and triethylamine (400 μL, 2.87 mmol, 1.0 equ.) in ethanol (10 mL) was stirred for 1 min, followed by the addition of 1-methyl-3-phenyl-1H-pyrazol-5(4H)-one (500 mg, 2.87 mmol, 1 equ.). The reaction mixture was concentrated after 21 h and washed with ethanol and hexanes; re-crystallized from ethanol, and washed with hexanes and ethanol to give 6-amino-1-methyl-3,4-diphenyl-1,4-dihydropyrano[2,3-c]pyrazole-5-carbonitrile (282 mg, 8.58 mmol, 30%) as a white solid. $^1$H-NMR (400 MHz) DMSO: 7.41-7.38 (m, 2H), 7.28-7.24 (m, 2H), 7.21-7.18 (m, 6H), 4.88 (s, 1H), 4.77 (s, 2H), 3.83 (s, 3H), $^{13}$C-NMR (100 MHz) DMSO: 158.1, 146.0, 144.8, 144.6, 133.2, 128.7, 128.5, 127.9, 127.8, 127.1, 126.4, 120.5, 95.7, 59.9, 38.2, 34.5; LC/MS-MS: 329.1→263.1 m/z; GS1 and GS2 at 30, DP=71, CE=31, CXP=18, $t_R$=4.00 min.

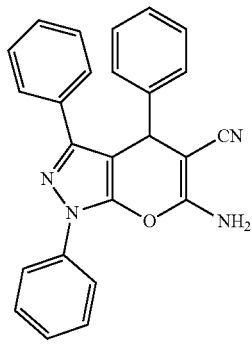 [SMILES: N#CC1=C(N)Oc2c(c(-c3ccccc3)nn2-c2ccccc2)C1c1ccccc1]

Chemical Formula: $C_{25}H_{18}N_4O$
Molecular Weight: 390.44

6-amino-1,3,4-triphenyl-1,4-dihydropyrano[2,3-c] pyrazole-5-carbonitrile

A mixture of benzaldehyde (290 μL, 2.87 mmol, 1.0 equ.), malononitrile (190 mg, 2.87 mmol, 1.0 equ.) and triethylamine (400 μL, 2.87 mmol, 1.0 equ.) in ethanol (10 mL) was stirred for 1 min, followed by the addition of 1,3-diphenyl-1H-pyrazol-5(4H)-one (678 mg, 2.87 mmol, 1 equ.). The precipitate was filtered off and washed with ethanol and hexanes, and re-crystallized from ethanol to give 6-amino-1,3,4-triphenyl-1,4-dihydropyrano[2,3-c]pyrazole-5-carbonitrile (330 mg, 0.845 mmol, 29%) as a white solid. $^1$H-NMR (400 MHz) CDCl$_3$: 7.82-7.80 (d, 2H), 7.55-7.50 (m, 4H), 7.41-7.37 (t, 1H), 7.32-7.22 (m, 8H), 4.96 (s, 1H), 4.68 (s, 2H), $^{13}$C-NMR (100 MHz) CDCl$_3$: 157.5, 147.7, 144.9, 142.6, 137.5, 132.2, 129.3, 128.8, 128.2, 128.2, 127.5, 127.4, 127.1, 126.9, 121.6, 118.9, 97.5, 64.8, 38.2; LC/MS-MS: 391.1→325.0 m/z; GS1 and GS2 at 30, DP=91, CE=33, CXP=22, $t_R$=4.33 min.

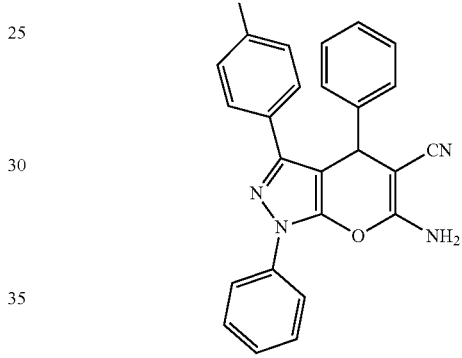

Chemical Formula: $C_{26}H_{20}N_4O_2$
Molecular Weight: 420.46

6-amino-3-(4-methoxyphenyl)-1,4-diphenyl-1,4-dihydropyrano[2,3-c]pyrazole-5-carbonitrile A mixture of benzaldehyde (290 μL, 2.87 mmol, 1.0 equ.), malononitrile (190 mg, 2.87 mmol, 1.0 equ.) and triethylamine (400 μL, 2.87 mmol, 1.0 equ.) in ethanol (10 mL) was stirred for 1 min, followed by the addition of 3-(4-methoxyphenyl)-1-phenyl-1H-pyrazol-5(4H)-one (764 mg, 2.87 mmol, 1 equ.). The reaction mixture was concentrated after 19 h and washed with ethanol and hexanes, re-crystallized from ethanol, and washed with hexanes and ethanol to give 6-amino-3-(4-methoxyphenyl)-1,4-diphenyl-1,4-dihydropyrano[2,3-c]pyrazole-5-carbonitrile (695 mg, 1.65 mmol, 58%) as a white solid. $^1$H-NMR (400 MHz) DMSO: 7.94-7.92 (d, 2H), 7.58-7.53 (m, 2H), 7.41-7.37 (t, 1H), 7.27-7.16 (m, 7H), 6.83-6.81 (d, 2H), 5.04 (s, 1H), 3.71 (s, 3H), $^{13}$C-NMR (100 MHz) DMSO: 159.5, 159.0, 146.6, 145.6, 144.5, 137.9, 129.8, 128.9, 128.3, 128.0, 127.3, 127.1, 125.1, 121.1, 120.3, 114.1, 97.5, 59.8, 55.5, 37.9; LC/MS-MS: 421.2→355.0 m/z; GS1 and GS2 at 30, DP=71, CE=33, CXP=24, $t_R$=4.28 min.

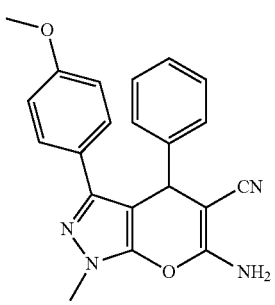 [SMILES: COc1ccc(-c2nn(C)c3c2C(c2ccccc2)C(C#N)=C(N)O3)cc1]

Chemical Formula: $C_{21}H_{18}N_4O_2$
Molecular Weight: 358.39

6-amino-3-(4-methoxyphenyl)-1-methyl-4-phenyl-1,4-dihydropyrano[2,3-c]pyrazole-5-carbonitrile A mixture of benzaldehyde (290 μL, 2.87 mmol, 1.0 equ.), malononitrile (190 mg, 2.87 mmol, 1.0 equ.) and triethylamine (400 μL, 2.87 mmol, 1.0 equ.) in ethanol (10 mL) was stirred for 1 min, followed by the addition of 3-(4-methoxyphenyl)-1-methyl-1H-pyrazol-5(4H)-one (583 mg, 2.87 mmol, 1 equ.). The reaction mixture was concentrated after 24 h. The crude material was purified by column chromatography (25% ethyl acetate in hexanes to 100% ethyl acetate), then re-crystallized from ethanol and washed with hexanes and ethanol to give 6-amino-3-(4-methoxyphenyl)-1-methyl-4-phenyl-1,4-dihydropyrano[2,3-c]pyrazole-5-carbonitrile (80.9 mg, 8%, 0.226 mmol) as a yellow solid. $^1$H-NMR (400 MHz) DMSO: 7.42-7.40 (d, 2H), 7.23-7.21 (m, 2H), 7.15-7.13 (d, 3H), 7.06 (s, 1H), 6.77-6.75 (d, 2H), 4.93 (s, 1H), 3.76 (s, 3H), 3.69 (s, 3H), $^{13}$C-NMR (100 MHz) DMSO: 159.1, 159.0, 145.9, 144.8, 144.5, 128.8, 127.8, 127.7, 127.1, 125.8, 120.5, 113.9, 95.0, 59.9, 55.4, 38.2, 34.4; LC/MS-MS: 359.1→293.0 m/z; GS1 and GS2 at 30, DP=76, CE=31, CXP=20, $t_R$=3.96 min.

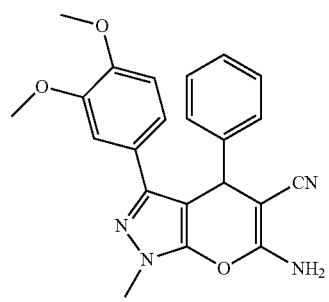 [SMILES: COc1ccc(-c2nn(C)c3c2C(c2ccccc2)C(C#N)=C(N)O3)cc1OC]

Chemical Formula: $C_{22}H_{20}N_4O_3$
Molecular Weight: 388.42

6-amino-3-(3,4-dimethoxyphenyl)-1-methyl-4-phenyl-1,4-dihydropyrano[2,3-c]pyrazole-5-carbonitrile A mixture of benzaldehyde (145 μL, 1.44 mmol, 1.0 equ.), malononitrile (90.0 mg, 1.44 mmol, 1.0 equ.) and triethylamine (200 μL, 1.44 mmol, 1.0 equ.) in ethanol (5.0 mL) was stirred for 1 min, followed by the addition of 3-(3,4-dimethoxyphenyl)-1-methyl-1H-pyrazol-5(4H)-one (336 mg, 1.44 mmol, 1 equ.). The reaction mixture was concentrated after 24 h. The crude material was purified by column chromatography. (25% ethyl acetate in hexanes to 100% ethyl acetate), then re-crystallized from ethanol and washed with hexanes and ethanol to give 6-amino-3-(3,4-dimethoxyphenyl)-1-methyl-4-phenyl-1,4-dihydropyrano[2,3-c]pyrazole-5-carbonitrile (48.5 mg, 9%, 0.124 mmol) as a yellow solid. $^1$H-NMR (400 MHz) CDCl$_3$: 7.29-7.28 (d, 2H), 7.23-7.21 (d, 2H), 7.00-6.98 (d, 1H), 6.88 (s, 1H), 6.72-6.70 (d, 2H), 4.84 (s, 1H), 4.75 (s, 2H), 3.82 (s, 6H), 3.60 (s, 3H), $^{13}$C-NMR (100 MHz) CDCl$_3$: 157.6, 148.7, 148.6, 146.1, 145.7, 143.1, 128.9, 127.5, 127.4, 125.6, 119.3, 119.3, 110.9, 109.7, 94.7, 64.4, 55.7, 55.6, 38.3, 34.1; LC/MS-MS: 389.1→323.0 m/z; GS1 and GS2 at 30, DP=66, CE=31, CXP=22, $t_R$=3.82 min.

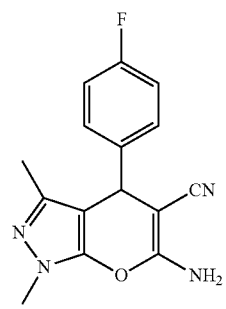 [SMILES: Cc1nn(C)c2c1C(c1ccc(F)cc1)C(C#N)=C(N)O2]

Chemical Formula: $C_{15}H_{13}FN_4O$
Molecular Weight: 284.29

6-amino-4-(4-fluorophenyl)-1,3-dimethyl-1,4-dihydropyrano[2,3-c]pyrazole-5-carbonitrile A mixture of 4-fluorobenzaldehyde (300 μL, 2.87 mmol, 1.0 equ.), malononitrile (190 mg, 2.87 mmol, 1.0 equ.) and triethylamine (400 mL, 2.87 mmol, 1.0 equ.) in ethanol (8.0 mL) was stirred for 1 min, followed by the addition of 1,3-dimethyl-1H-pyrazol-5(4H)-one (322 mg, 2.87 mmol, 1 equ.). The reaction mixture was concentrated after 24 h and washed with ethanol and hexanes, and re-crystallized from ethanol to give 6-amino-4-(4-fluorophenyl)-1,3-dimethyl-1,4-dihydropyrano[2,3-c]pyrazole-5-carbonitrile (335 mg, 41%, 1.17 mmol) as a white solid. $^1$H-NMR (400 MHz) DMSO: 7.23-7.20 (m, 2H), 7.16-7.12 (m, 2H), 7.07 (s, 2H), 4.61 (s, 1H), 3.60 (s, 3H), 1.67 (s, 3H), $^{13}$C-NMR (100 MHz) DMSO: 162.7, 159.9, 144.6, 142.9, 140.7, 129.9, 120.6, 115.6, 115.4, 96.3, 59.6, 56.4, 36.7, 33.8, 12.8; LC/MS-MS: 285.1→219.1 m/z; GS1 and GS2 at 30, DP=61, CE=27, CXP=14, $t_R$=3.80 min.

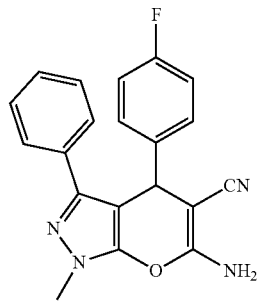 [SMILES: Cn1nc(-c2ccccc2)c2c1OC(N)=C(C#N)C2c1ccc(F)cc1]

Chemical Formula: $C_{20}H_{15}FN_4O$
Molecular Weight: 346.36

6-amino-4-(4-fluorophenyl)-1-methyl-3-phenyl-1,4-dihydropyrano[2,3-c]pyrazole-5-carbonitrile A mixture of the 4-fluorobenzaldehyde (300 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 1-methyl-3-phenyl-1H-pyrazol-5(4H)-one (500 mg, 2.87 mmol, 1 equ.). The reaction mixture was concentrated after 20 h in vacuo and washed with ethanol and hexanes, and re-crystallized from ethanol to give 6-amino-4-(4-fluorophenyl)-1-methyl-3-phenyl-1,4-dihydropyrano[2,3-c]pyrazole-5-carbonitrile (182 mg, 0.525 mmol, 18%) as a light yellow solid. $^1$H-NMR (400 MHz) DMSO: 7.50-7.48 (d, 2H), 7.22-7.18 (m, 5H), 7.11 (s, 2H), 7.05-6.98 (t, 2H) 5.04 (s, 1H), 3.78 (s, 3H), $^{13}$C-NMR (100 MHz) DMSO: 162.5, 159.1, 146.0, 144.6, 140.9, 133.1, 129.8, 128.5, 127.9, 126.5, 120.4, 115.5, 115.3, 95.5, 59.7, 37.4, 34.5; LC/MS-MS: 347.1→281.0 m/z; GS1 and GS2 at 30, DP=66, CE=31, CXP=14, $t_R$=4.00 min.

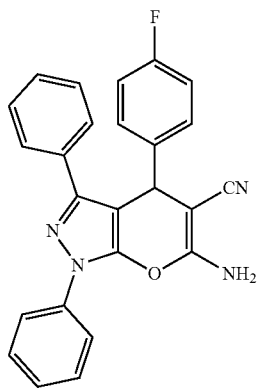 [SMILES: N#CC1=C(N)Oc2c(c(-c3ccccc3)nn2-c2ccccc2)C1c1ccc(F)cc1]

Chemical Formula: $C_{25}H_{17}FN_4O$
Molecular Weight: 408.43

6-amino-4-(4-fluorophenyl)-1,3-diphenyl-1,4-dihydropyrano[2,3-c]pyrazole-5-carbonitrile A mixture of 4-fluorobenzaldehyde (300 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 1,3-diphenyl-1H-pyrazol-5(4H)-one (678 mg, 2.87 mmol, 1 equ.). The precipitate formed was filtered out and washed with ethanol and hexanes, and re-crystallized from ethanol to afford 6-amino-4-(4-fluorophenyl)-1,3-diphenyl-1,4-dihydropyrano[2,3-c]pyrazole-5-carbonitrile (240 mg, 0.588 mmol, 20%) as a white powder. $^1$H-NMR (400 MHz) DMSO: 7.94-7.92 (d, 2H), 7.61-7.55 (m, 4H), 7.42-7.38 (t, 1H), 7.28-7.24 (m, 7H), 7.06-7.02 (t, 2H), 5.15 (s, 1H), $^{13}$C-NMR (100 MHz) DMSO: 162.6, 159.0, 146.8, 145.6, 140.6, 137.8, 132.5, 130.0, 129.9, 129.8, 128.6, 128.6, 127.3, 127.0, 121.3, 120.2, 115.6, 115.4, 97.9, 59.6, 37.0; LC/MS-MS: 410.4→242.2 m/z; GS1 and GS2 at 30, DP=21, CE=47, CXP=16, $t_R$=4.63 min.

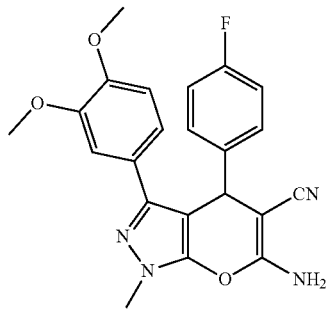 [SMILES: COc1ccc(-c2nn(C)c3c2C(c2ccc(F)cc2)C(C#N)=C(N)O3)cc1OC]

Chemical Formula: $C_{22}H_{19}FN_4O_3$
Molecular Weight: 406.41

6-amino-3-(3,4-dimethoxyphenyl)-4-(4-fluorophenyl)-1-methyl-1,4-dihydropyrano[2,3-c]pyrazole-5-carbonitrile A mixture of 4-fluorobenzaldehyde (300 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 3-(3,4-dimethoxyphenyl)-1-methyl-1H-pyrazol-5(4H)-one (672 mg, 2.87 mmol, 1 equ.). The precipitate formed was filtered out and washed with ethanol and hexanes, and re-crystallized from ethanol to give 6-amino-3-(3,4-dimethoxyphenyl)-4-(4-fluorophenyl)-1-methyl-1,4-dihydropyrano[2,3-c]pyrazole-5-carbonitrile (782 mg, 1.93 mmol, 67%) as a white powder. $^1$H-NMR (400 MHz) DMSO: 7.20-7.18 (m, 2H), 7.09-7.03 (m, 5H), 6.96-6.95 (d, 1H), 6.80-6.78 (d, 2H), 5.02 (s, 1H), 3.77 (s, 3H), 3.69 (s, 3H), 3.62 (s, 3H)$^{13}$C-NMR (100 MHz) DMSO: 162.6, 159.0, 148.7, 146.0, 144.6, 141.0, 141.0, 129.8, 129.7, 125.9, 120.4, 119.0, 115.7, 115.4, 111.8, 109.8, 94.7, 55.8, 55.7, 37.3, 34.4; LC/MS-MS: 407.1→341.1 m/z; GS1 and GS2 at 30, DP=71, CE=33, CXP=22, $t_R$=3.86 min.

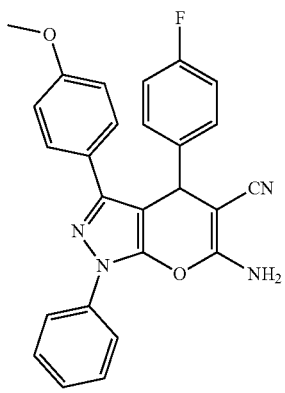 [SMILES: COc1ccc(-c2nn(-c3ccccc3)c3c2C(c2ccc(F)cc2)C(C#N)=C(N)O3)cc1]

Chemical Formula: $C_{26}H_{19}FN_4O_2$
Molecular Weight: 438.45

6-amino-4-(4-fluorophenyl)-3-(4-methoxyphenyl)-1-phenyl-1,4-dihydropyrano[2,3-c]pyrazole-5-carbonitrile A mixture of 4-fluorobenzaldehyde (300 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 3-(4-methoxyphenyl)-1-phenyl-1H-pyrazol-5(4H)-one (764 mg, 2.87 mmol, 1 equ.). The precipitate formed was filtered off and washed with ethanol and hexanes, and re-crystallized from ethanol to afford 6-amino-4-(4-fluorophenyl)-3-(4-methoxyphenyl)-1-phenyl-1,4-dihydropyrano[2,3-c]pyrazole-5-carbonitrile (800 mg, 1.83 mmol, 64%) as white solid. $^1$H-NMR (400 MHz) DMSO: 7.93-7.91 (d, 2H), 7.55-7.53 (m, 4H), 7.41-7.37 (t, 1H), 7.26-7.23 (m, 4H), 7.07-7.05 (t, 2H), 6.84-6.82 (d, 2H), 5.11 (s, 1H), 3.72 (s, 3H) $^{13}$C-NMR (100 MHz) DMSO: 162.6, 159.6, 159.0, 146.6, 145.5, 140.7, 140.6, 137.9, 130.0, 129.9, 129.8, 128.3, 127.1, 125.0, 121.1, 120.2, 115.6, 115.4, 114.1, 97.3, 59.6, 55.5, 37.0; LC/MS-MS: 439.2→373.0 m/z; GS1 and GS2 at 30, DP=61, CE=35, CXP=24, $t_R$=4.28 min.

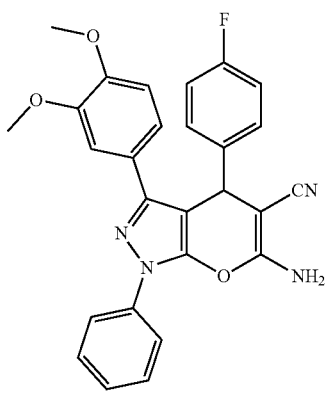 [SMILES: COc1ccc(-c2nn(-c3ccccc3)c3c2C(c2ccc(F)cc2)C(C#N)=C(N)O3)cc1OC]

Chemical Formula: $C_{27}H_{21}FN_4O_3$
Molecular Weight: 468.48

6-amino-3-(3,4-dimethoxyphenyl)-4-(4-fluorophenyl)-1-phenyl-1,4-dihydropyrano[2,3-c]pyrazole-5-carbonitrile A mixture of 4-fluorobenzaldehyde (70.0 µL, 0.675 mmol, 1.0 equ.), malononitrile (45.0 mg, 0.675 mmol, 1.0 equ.) and triethylamine (90.0 µL, 0.675 mmol, 1.0 equ.) in ethanol (3.0 mL) was stirred for 1 min, followed by the addition of the 3-(3,4-dimethoxyphenyl)-1-phenyl-1H-pyrazol-5(4H)-one (200 mg, 0.675 mmol, 1 equ.). The reaction mixture was concentrated after 19 h and the crude material was purified by column chromatography (25% ethyl acetate in hexanes to 100% ethyl acetate). The yellow solid was further purified by re-crystallization from ethanol to give 6-amino-3-(3,4-dimethoxyphenyl)-4-(4-fluorophenyl)-1-phenyl-1,4-dihydropyrano[2,3-c]pyrazole-5-carbonitrile (164 mg, 0.350 mmol, 12%) as a white solid. $^1$H-NMR (400 MHz) CDCl$_3$: 7.80-7.78 (d, 2H), 7.52-7.48 (t, 2H), 7.38-7.35 (t, 1H), 7.25-7.21 (m, 2H), 7.05-6.95 (m, 4H), 6.75-6.73 (d, 1H), 4.91 (s, 1H), 4.84 (s, 1H), 3.84 (s, 3H), 3.71 (s, 3H), $^{13}$C-NMR (100 MHz) CDCl$_3$: 163.2, 157.8, 149.2, 148.7, 147.5, 144.9, 138.6, 137.4, 129.3, 129.1, 129.0, 127.1, 125.0, 121.5, 119.8, 119.0, 115.9, 115.7, 110.8, 109.9, 96.6, 64.0, 55.8, 55.7, 37.5; LC/MS-MS: 469.3→403.1 m/z; GS1 and GS2 at 30, DP=6, CE=35, CXP=26, $t_R$=4.16 min.

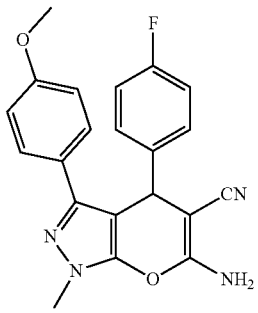 [SMILES: COc1ccc(-c2nn(C)c3c2C(c2ccc(F)cc2)C(C#N)=C(N)O3)cc1]

Chemical Formula: $C_{21}H_{17}FN_4O_2$
Molecular Weight: 376.38

6-amino-4-(4-fluorophenyl)-3-(4-methoxyphenyl)-1-methyl-1,4-dihydropyrano[2,3-c]pyrazole-5-carbonitrile A mixture of 4-fluorobenzaldehyde (300 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 3-(4-methoxyphenyl)-1-methyl-1H-pyrazol-5(4H)-one (586 mg, 2.87 mmol, 1 equ.). The reaction mixture was concentrated after 19 h and the precipitate formed was washed with ethanol and hexanes, re-crystallized from ethanol, and washed with hexanes and ethanol to give 6-amino-4-(4-fluorophenyl)-3-(4-methoxyphenyl)-1-methyl-1,4-dihydropyrano[2,3-c]pyrazole-5-carbonitrile (350 mg, 0.930 mmol, 32%) as a white solid. $^1$H-NMR (400 MHz) DMSO: 7.43-7.40 (d, 2H), 7.20-7.16 (m, 2H), 7.10 (s, 2H), 7.06-7.02 (t, 2H), 6.78-6.76 (d, 2H), 4.99 (s, 1H), 3.75 (s, 3H), 3.69 (s, 3H), $^{13}$C-NMR (100 MHz) DMSO: 162.5, 159.1, 145.8, 144.6, 141.0, 141.0, 129.8, 129.7, 127.8, 125.7, 120.5, 115.6, 115.4, 113.9, 94.9, 59.7, 55.4, 37.4, 34.4; LC/MS-MS: 377.1→311.1 m/z; GS1 and GS2 at 30, DP=66, CE=33, CXP=20, $t_R$=3.98 min.

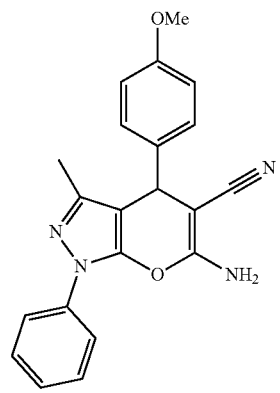 [SMILES: COc1ccc(C2C(C#N)=C(N)Oc3c2c(C)nn3-c2ccccc2)cc1]

Chemical Formula: $C_{21}H_{18}N_4O_2$
Molecular Weight: 358.39

6-amino-4-(4-methoxyphenyl)-3-methyl-1-phenyl-1,4-dihydropyrano[2,3-c]pyrazole-5-carbonitrile A mixture of anisaldehyde (350 µL, 2.87 mmol, 1.0 equ.), malononitrile (190 mg, 2.87 mmol, 1.0 equ.) and triethylamine (400 µL, 2.87 mmol, 1.0 equ.) in ethanol (10 mL) was stirred for 1 min, followed by the addition of 6-amino-4-(4-methoxyphenyl)-3-methyl-1-phenyl-1,4-dihydropyrano[2,3-c]pyrazole-5-carbonitrile (500 mg, 2.87 mmol, 1 equ.). The reaction mixture was concentrated after 24 h and the precipitate was washed with ethanol and hexanes, and re-crystallized from ethanol to give 6-amino-4-(4-methoxyphenyl)-3-methyl-1-phenyl-1,4-dihydropyrano[2,3-c]pyrazole-5-carbonitrile (800 mg, 78%, 2.23 mmol) as a white solid. $^1$H-NMR (400 MHz) DMSO: 7.80-7.78 (d, 2H), 7.51-7.47 (t, 2H), 7.32-7.28 (t, 1H), 7.18-7.16 (m, 4H), 6.91-6.89 (d, 2H), 4.62 (s, 1H), 3.74 (s, 3H), 1.79 (s, 3H), $^{13}$C-NMR (100 MHz) DMSO: 159.7, 158.6, 145.7, 144.2, 138.0, 136.0, 129.7, 129.2, 126.5, 120.5, 120.3, 114.3, 99.3, 59.0, 55.4, 36.4, 13.0; LC/MS-MS: 359.2→293.0 m/z; GS1 and GS2 at 30, DP=71, CE=29, CXP=20, $t_R$=4.14 min.

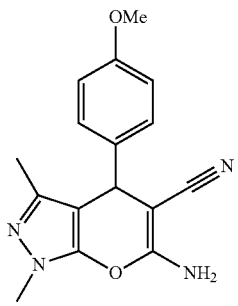 [SMILES: COc1ccc(C2C(C#N)=C(N)Oc3c2c(C)nn3C)cc1]

Chemical Formula: $C_{16}H_{16}N_4O_2$
Molecular Weight: 296.32

6-amino-4-(4-methoxyphenyl)-1,3-dimethyl-1,4-dihydropyrano[2,3-c]pyrazole-5-carbonitrile A mixture of anisaldehyde (350 μL, 2.87 mmol, 1.0 equ.), malononitrile (190 mg, 2.87 mmol, 1.0 equ.) and triethylamine (400 μL, 2.87 mmol, 1.0 equ.) in ethanol (10 mL) was stirred for 1 min, followed by the addition of 1,3-dimethyl-1H-pyrazol-5(4H)-one (321 mg, 2.87 mmol, 1 equ.). The reaction mixture was concentrated after 24 h and the crude material was purified by column chromatography (25% ethyl acetate in hexanes to 100% ethyl acetate). The yellow solid was washed with ethanol and hexanes, and re-crystallized from ethanol to give 6-amino-4-(4-methoxyphenyl)-1,3-dimethyl-1,4-dihydropyrano[2,3-c]pyrazole-5-carbonitrile (370 mg, 1.25 mmol, 44%) as a white solid. $^1$H-NMR (400 MHz) CDCl$_3$: 7.12-7.10 (d, 2H), 6.85-6.83 (d, 2H), 4.61 (s, 2H), 4.55 (s, 1H), 3.79 (s, 3H), 3.69 (s, 3H), 1.80 (s, 3H)$^{13}$C-NMR (100 MHz) CDCl$_3$: 158.8, 157.9, 144.5, 144.4, 134.5, 128.8, 119.3, 114.0, 96.4, 64.2, 55.2, 36.7, 33.7, 12.7; LC/MS-MS: 297.0→231.2 m/z; GS1 and GS2 at 30, DP=61, CE=27, CXP=16, $t_R$=3.71 min.

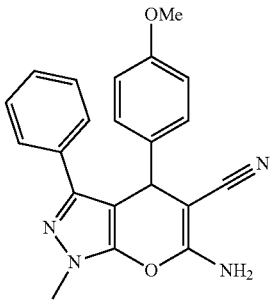 [SMILES: COc1ccc(C2C(C#N)=C(N)Oc3c2c(-c2ccccc2)nn3C)cc1]

Chemical Formula: $C_{21}H_{18}N_4O_2$
Molecular Weight: 358.39

6-amino-4-(4-methoxyphenyl)-1-methyl-3-phenyl-1,4-dihydropyrano[2,3-c]pyrazole-5-carbonitrile A mixture of anisaldehyde (350 μL, 2.87 mmol, 1.0 equ.), malononitrile (190 mg, 2.87 mmol, 1.0 equ.) and triethylamine (400 μL, 2.87 mmol, 1.0 equ.) in ethanol (10 mL) was stirred for 1 min, followed by the addition of 1-methyl-3-phenyl-1H-pyrazol-5(4H)-one (500 mg, 2.87 mmol, 1 equ.). The reaction mixture was concentrated after 24 h and the precipitate was washed with ethanol and hexanes, and product re-crystallized from ethanol to give 6-amino-4-(4-methoxyphenyl)-1-methyl-3-phenyl-1,4-dihydropyrano[2,3-c]pyrazole-5-carbonitrile (210 mg, 20%, 0.586 mmol) as a white solid. $^1$H-NMR (400 MHz) DMSO: 7.50-7.48 (d, 2H), 7.21-7.17 (m, 3H), 7.05-7.02 (m, 4H), 6.76-6.74 (d, 2H), 4.91 (s, 1H), 3.76 (s, 3H), 3.64 (s, 3H), $^{13}$C-NMR (100 MHz) DMSO: 158.9, 158.3, 146.0, 144.6, 136.9, 133.2, 128.9, 128.5, 127.8, 126.4, 120.6, 114.1, 95.9, 60.3, 55.3, 37.5, 34.5; LC/MS-MS: 359.2→293.0 m/z; GS1 and GS2 at 30, DP=66, CE=29, CXP=20, $t_R$=3.98 min.

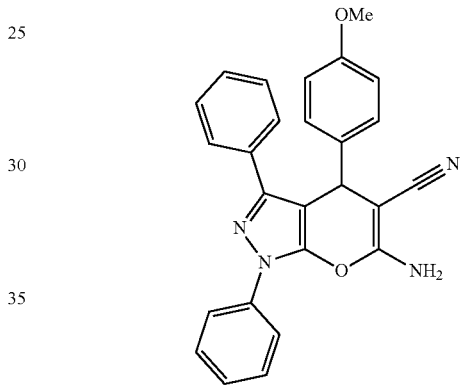

Chemical Formula: $C_{26}H_{20}N_4O_2$
Molecular Weight: 420.46

6-amino-4-(4-methoxyphenyl)-1-methyl-3-phenyl-1,4-dihydropyrano[2,3-c]pyrazole-5-carbonitrile A mixture of anisaldehyde (350 μL, 2.87 mmol, 1.0 equ.), malononitrile (190 mg, 2.87 mmol, 1.0 equ.) and triethylamine (400 μL, 2.87 mmol, 1.0 equ.) in ethanol (10 mL) is stirred for 1 min, followed by the addition of 1,3-diphenyl-1H-pyrazol-5(4H)-one (678 mg, 2.87 mmol, 1 equ.). The reaction mixture was concentrated after 24 h and the precipitate was washed with ethanol and hexanes. The product was re-crystallized from ethanol to afford 6-amino-4-(4-methoxyphenyl)-1-methyl-3-phenyl-1,4-dihydropyrano[2,3-c]pyrazole-5-carbonitrile (1.05 g, 87%, 2.50 mmol) as a white solid. $^1$H-NMR (400 MHz) DMSO: 7.94-7.92 (d, 2H), 7.63-7.61 (d, 2H), 7.57-7.53 (t, 2H), 7.40-7.36 (t, 1H), 7.29-7.23 (m, 3H) 7.15 (s, 2H), 7.13-7.11 (d, 2H), 6.78-6.76 (d, 2H), 5.02 (s, 1H), 3.65 (s, 3H), $^{13}$C-NMR (100 MHz) DMSO: 158.9, 158.4, 146.7, 145.6, 137.9, 136.5, 132.6, 129.8, 129.0, 128.7, 128.5, 127.2, 127.0, 121.2, 120.3, 114.2, 98.3, 60.2, 55.3, 37.1; LC/MS-MS: 421.2→355.0 m/z; GS1 and GS2 at 30, DP=81, CE=35, CXP=24, $t_R$=4.32 min.

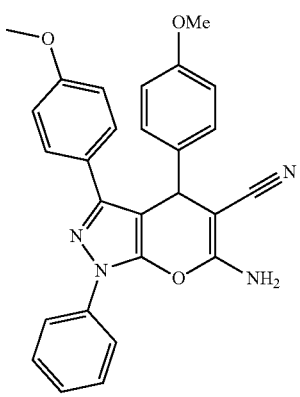 [SMILES: COc1ccc(-c2nn(-c3ccccc3)c3c2C(c2ccc(OC)cc2)C(C#N)=C(N)O3)cc1]

Chemical Formula: C₂₇H₂₂N₄O₃
Molecular Weight: 450.49

6-amino-3,4-bis(4-methoxyphenyl)-1-phenyl-1,4-dihydropyrano[2,3-c]pyrazole-5-carbonitrile A mixture of anisaldehyde (350 μL, 2.87 mmol, 1.0 equ.), malononitrile (190 mg, 2.87 mmol, 1.0 equ.) and triethylamine (400 μL, 2.87 mmol, 1.0 equ.) in ethanol (10 mL) was stirred for 1 min, followed by the addition of 3-(4-methoxyphenyl)-1-phenyl-1H-pyrazol-5(4H)-one (764 mg, 2.87 mmol, 1 equ.). The reaction mixture was concentrated after 24 h and the precipitate was washed with ethanol and hexanes, and then re-crystallized from ethanol to give 6-amino-3,4-bis(4-methoxyphenyl)-1-phenyl-1,4-dihydropyrano[2,3-c]pyrazole-5-carbonitrile (1.06 g, 2.35 mmol, 82%) as a white solid. $^{1}$H-NMR (400 MHz) DMSO: 7.93-7.91 (d, 2H), 7.56-7.52 (m, 4H), 7.38-7.35 (t, 1H), 7.15-7.11 (m, 4H), 6.83-6.78 (m, 4H), 4.98 (s, 1H), 3.70 (s, 3H), 3.66 (s, 3H), $^{13}$C-NMR (100 MHz) DMSO: 159.5, 158.9, 158.4, 146.6, 145.5, 137.9, 136.6, 129.8, 129.0, 128.3, 127.0, 125.2, 121.0, 120.4, 114.2, 114.1, 97.7, 60.3, 55.5, 55.3, 37.1; LC/MS-MS: 452.3→89.1 m/z; GS1 and GS2 at 30, DP=36, CE=39, CXP=4, $t_R$=3.47 min.

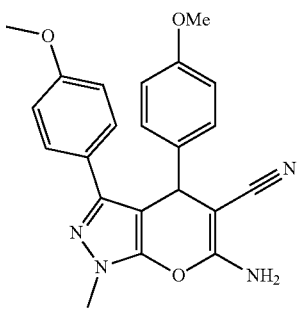 [SMILES: COc1ccc(-c2nn(C)c3c2C(c2ccc(OC)cc2)C(C#N)=C(N)O3)cc1]

Chemical Formula: C₂₂H₂₀N₄O₃
Molecular Weight: 388.42

6-amino-3,4-bis(4-methoxyphenyl)-1-methyl-1,4-dihydropyrano[2,3-c]pyrazole-5-carbonitrile A mixture of anisaldehyde (350 μL, 2.87 mmol, 1.0 equ.), malononitrile (190 mg, 2.87 mmol, 1.0 equ.) and triethylamine (400 μL, 2.87 mmol, 1.0 equ.) in ethanol (10 mL) was stirred for 1 min, followed by the addition of 3-(4-methoxyphenyl)-1-methyl-1H-pyrazol-5(4H)-one (689 mg, 2.87 mmol, 1 equiv.). The reaction mixture was concentrated after 24 h and the precipitate was washed with ethanol and hexanes, and then re-crystallized from ethanol to give 6-amino-3,4-bis(4-methoxyphenyl)-1-methyl-1,4-dihydropyrano[2,3-c]pyrazole-5-carbonitrile (690 mg, 1.78 mmol, 62%) as a white solid. (400 MHz) DMSO: 7.42-7.40 (d, 2H), 7.05-7.03 (d, 2H), 7.00 (s, 2H), 6.78-6.75 (dd, 4H), 4.86 (s, 1H), 3.73 (s, 3H), 3.68 (s, 3H), 3.66 (s, 3H), $^{13}$C-NMR (100 MHz) DMSO: 159.0, 158.9, 158.3, 145.9, 144.5, 136.9, 128.9, 127.7, 125.9, 120.6, 114.1, 113.9, 95.3, 60.3, 55.4, 55.3, 37.5, 34.3; LC/MS-MS: 389.2→323.0 m/z; GS1 and GS2 at 30, DP=66, CE=29, CXP=22, $t_R$=3.94 min.

Example 3

ELISA Screen

Figure 2:
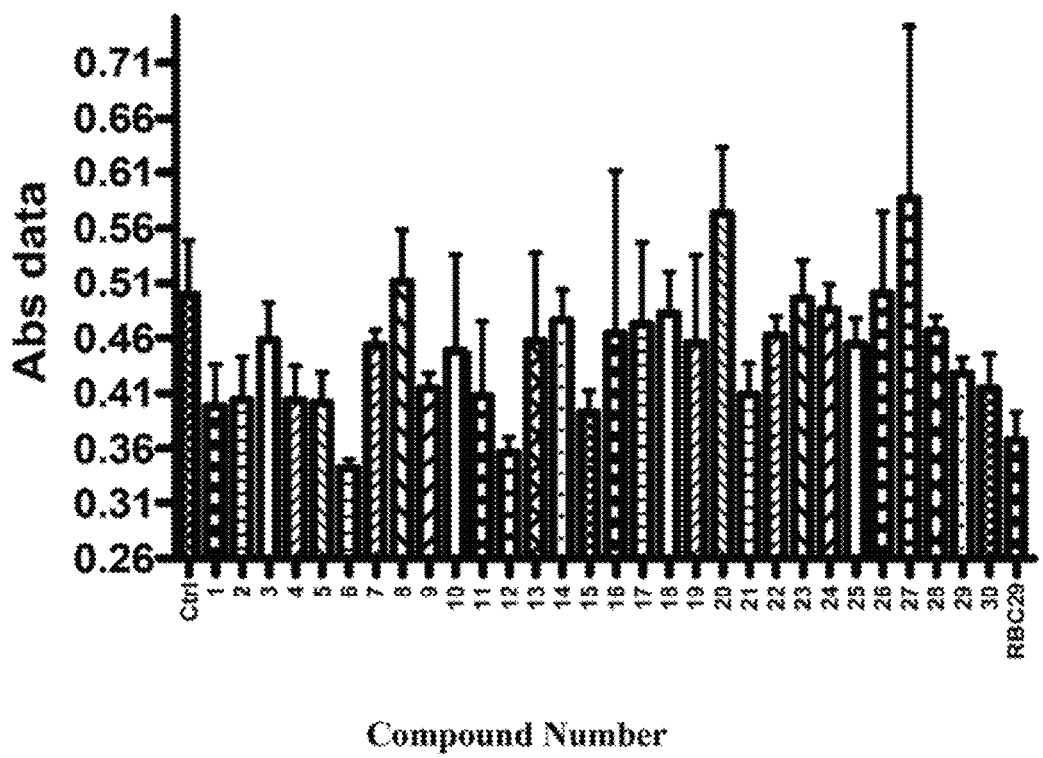
FIG. 2 shows the results of the Elisa screen of putative Ral GTPase inhibitors of the invention.

The Elisa screen is based upon the canonical binding principle wherein activated (GTP-bound) protein forms a complex with either RalA or RalB to RalBP1. The ELISA assay was adapted from the widely used Ral activation pull-down assays (Cancer Res. 2005; 65: 7111-7120). Recombinant GST-His6-RalBP1 fusion protein was purified from bacteria by GST affinity and then adsorbed via a His6 tag directly onto metal-chelate derivatized 96-well microplates. Stably transfected UMUC3 cell lines expressing either FLAG-RalA or FLAG-RalB were created, where the ectopic protein functions as a reporter for Ral activation and the FLAG tag allows highly sensitive and specific detection of the protein; we resorted to stable expression of FLAG-Ral in UMUC3. A robust signal to noise ratio (>100:1) using anti-FLAG primary antibody and HRP-conjugated anti-mouse secondary antibody with signal proportional to input protein from 0.3 up to 10 mcg of total cell lysate was obtained from cells cultured in 96 well microplates where enough total cell protein can be recovered for analysis. The inventors used this assay to screen compounds for Ral GTPase inhibitory activity. FIG. 2 shows the Elisa screening data for 31 putative Ral GTPase inhibitors of the invention. Ral GTPase inhibitor RBC10 was used in combination testing of Ral GTPase inhibitors in conjunction with MEK Inhibitor AZD6244 in bladder cancer cell lines A549, H358, H460, H2009, SW1573, CRL2169, J82, KU7, MGHU4, LULU2, UMUC3 and showed synergistic efficacy. Ral GTPase inhibitor RBC10 was used in combination testing of Ral GTPase inhibitors in conjunction with MEK Inhibitor AZD6244 in lung cancer cell lines A549, H2009, H358, H460, SW1573 and showed synergistic efficacy. Thereafter, dose response curves were determined for Ral GTPase inhibitors of the invention and RalA GTPase inhibition. Additionally, cell spreading assays following treatment with Ral GTPase inhibitors of the invention in mouse embryonic fibroblasts (MEFs), including a dose response curve for cell spreading in these cells. Testing of cell survival of colon cancer cells WiDr, HT29, HCT116, HCT15, DLD1, and Caco-2, treated in vitro with four Ral GTPase inhibitors of the invention showed significant reduction in cell growth in treated cells versus vehicle control.

Figure 3:
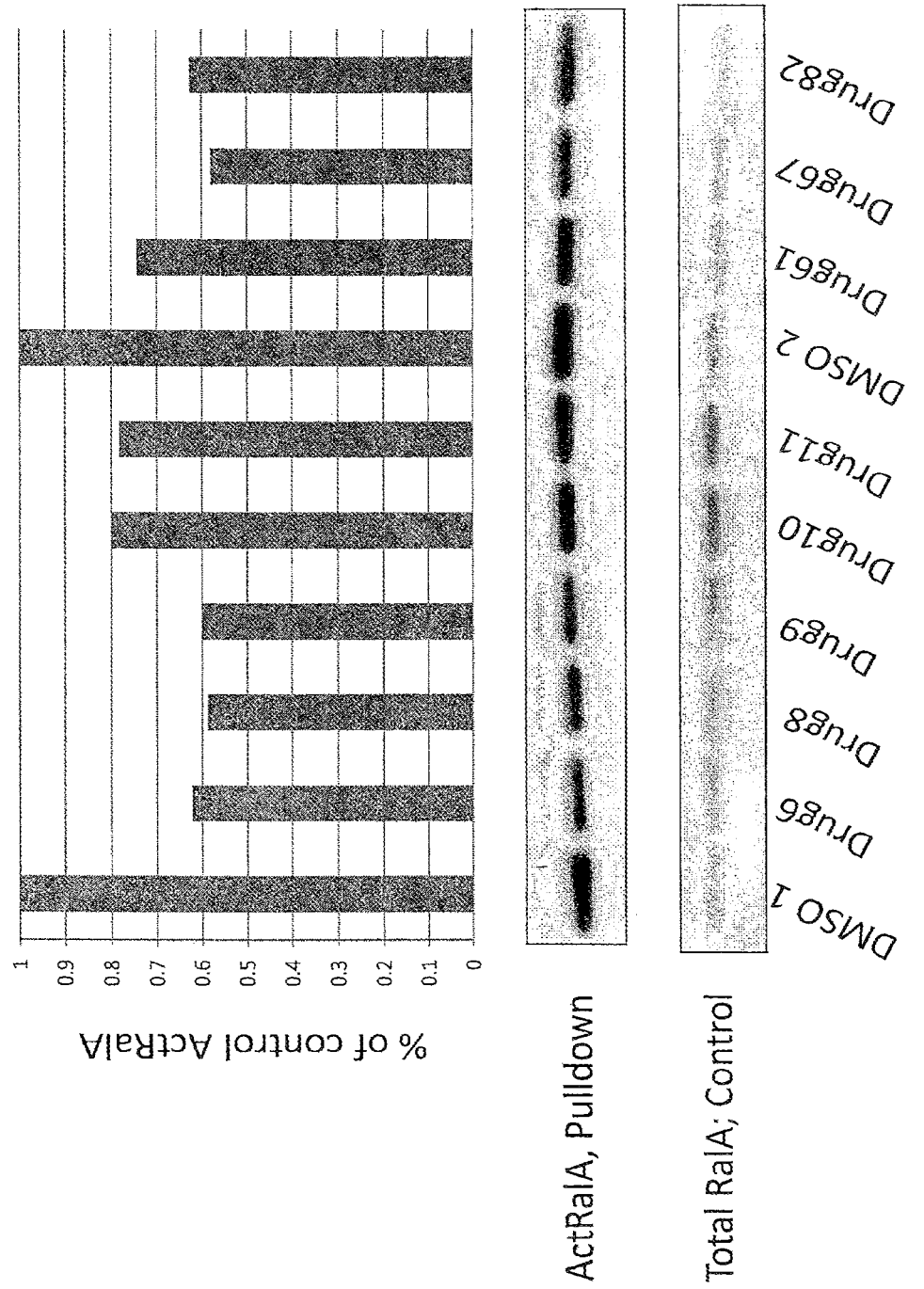
FIG. 3 shows the results of a Ral activation pull-down assay for eight Ral GTPase inhibitors of the invention.

Similarly, testing of cell survival of pancreatic cancer cells BXPC3, HPAC, and MiaPACA2, treated in vitro with seven Ral GTPase inhibitors of the invention showed significant reduction in cell growth in treated cells versus vehicle control. FIG. 3 shows the results of a Ral activation pull-down assay for eight Ral GTPase inhibitors of the invention. Each drug tested underwent two-hour incubation at 50 um in regular 10% J82 medium. The DMSO control lysate was used for two pulldowns, which were averaged and % control calculated against this average.

Example 4

ALPHA Screen

An Amplified Luminescent Proximity Homogeneous Assay (Alpha) screen was conducted to measure the disruption of Ral protein-protein interactions caused by the Ral-GTPase inhibiting compounds of the present invention. The ALPHA assay involves an acceptor bead that binds to one analyte of interest (for example, His-tagged BP1) and a donor bead bound to a second analyte of interest (for example, BP2). With excitation, a photosensitizer in the donor bead converts ambient oxygen to reactive singlet oxygen. When donor and acceptor are within 200 nm, singlet oxygen species reacts with thioxene compounds in the acceptor bead to generate a chemiluminescent signal that emits at 370 nm. The energy is immediately transferred to fluorophores contained in the same acceptor bead, which effectively shifts the emission wavelength to 520-620 nm. The donor bead is excited at 680 nm and in proximity of the acceptor bead will emit light at a range of 520 nm-620 nm (GST-tagged BP2). This chemiluminescent reaction can be measured immediately following incubation of the proteins. Chemiluminescence is only observed when beads are in close proximity and thus protein-protein interaction between the test proteins is intact. In this way, the Ral-BP1→RalA binding disruption caused by the Ral-GTPase inhibiting compounds of the present invention was evaluated.

Figure 4:
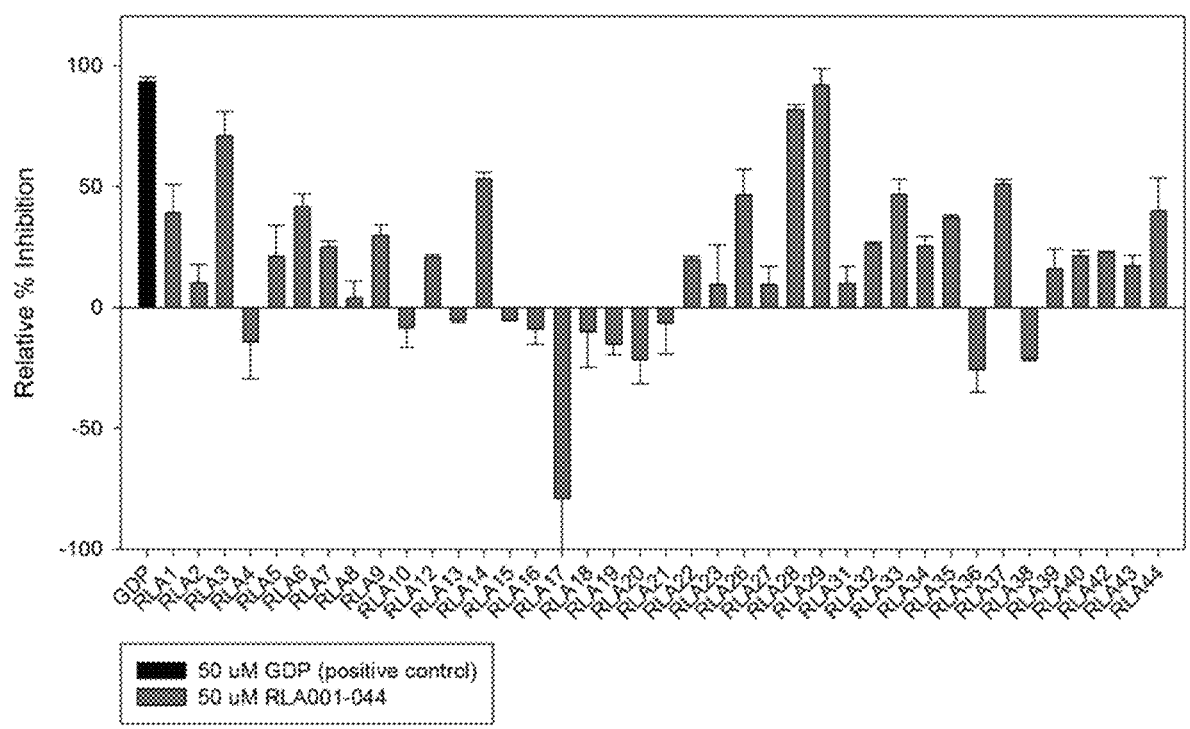
FIG. 4 shows the results of an ALPHA screen of RalBP1-RalA binding inhibition in the presence of 50 µM of the Ral GTPase inhibiting compounds of the invention.
Figure 4:
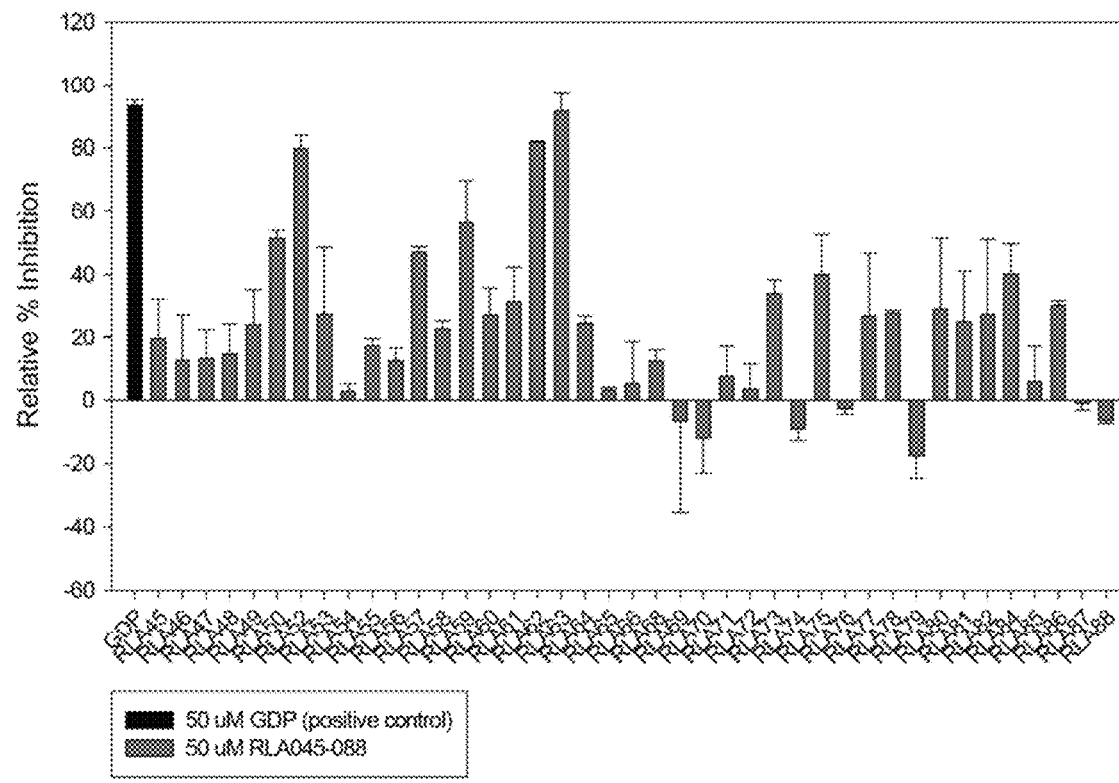
Figure 5:
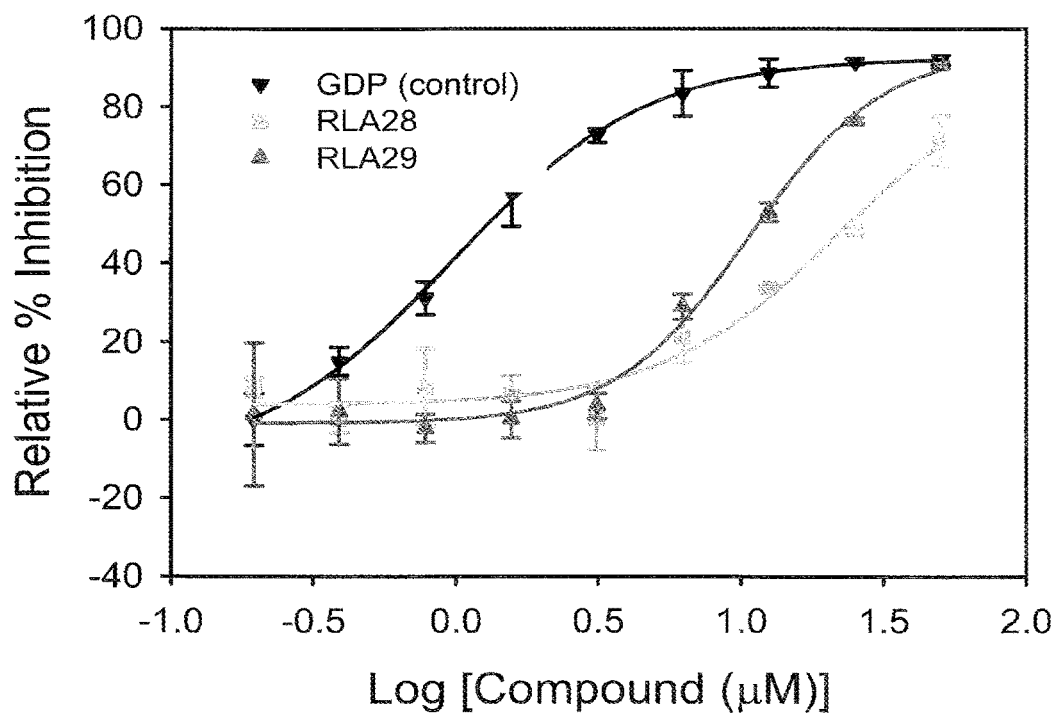
FIG. 5 shows the results of an ALPHA screen of RalBP1-RalA binding inhibition of eight Ral GTPase inhibiting compounds of the invention, over a micromolar dosage range.
Figure 5:
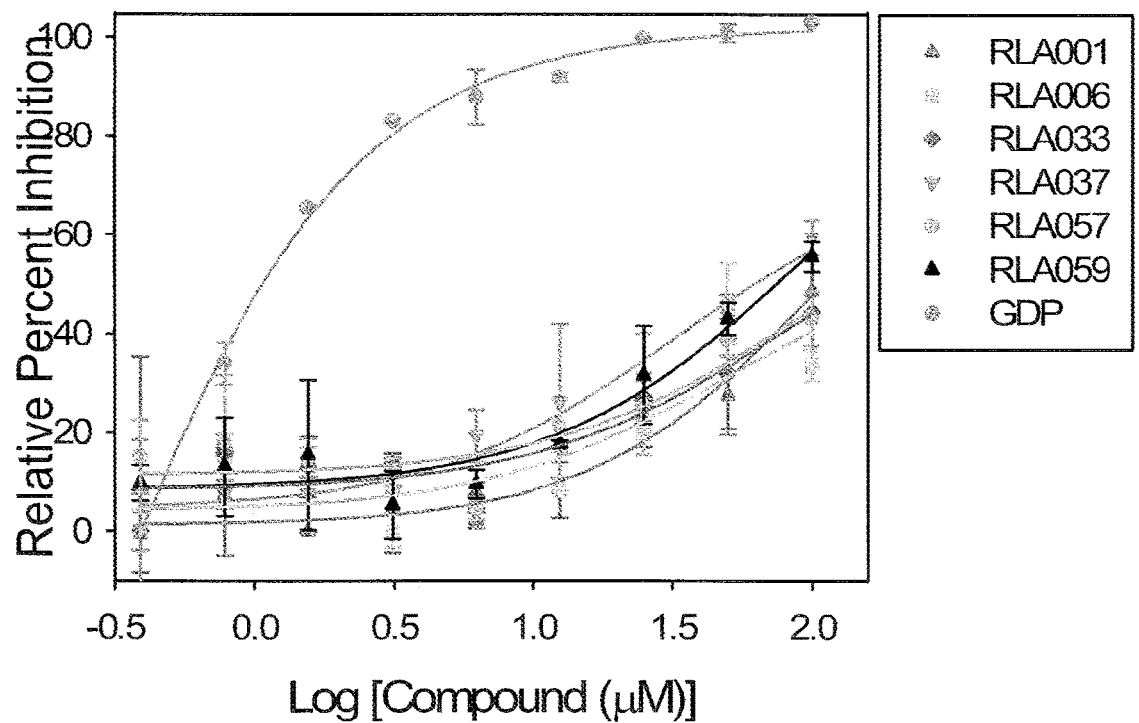

An initial ALPHA screen was conducted to measure RalBP1-RalA binding inhibition in the presence of 50 µM of the Ral GTPase inhibiting compounds of the invention (FIG. 4). Thereafter, an ALPHA screen was conducted in a dose-response manner to measure the protein binding inhibition of certain Ral-GTPase inhibiting compounds of the invention over a micromolar compound concentration range (FIG. 5).

Example 5

In Vivo Pharmacokinetics Evaluation

The pharmacokinetics of certain Ral-GTPase inhibiting compounds of the invention were evaluated in mice. Following intraperitoneal injection or oral administration, blood samples were collected over several hours and drug concentrations were evaluated by capillary coupled with Time of Flight (TOF) spectrometry. Exemplary results for three tests are shown in Table 2:

TABLE 2

Pharmacokinetic parameters following oral (PO) or intraperitoneal (IP) administration of compound of the invention.

| Compound-route | Cmax (µM) | tmax (hr) | $AUC_{0-t}$ (ng · mL-1 · hr) | $AUC_{0-\infty}$ (ng · mL-1 · hr) | $t^{1/2}$ (hr) | Cl/F (mL · hr-1) |
|---|---|---|---|---|---|---|
| RBC8-IP | 1.3 | 2 | 1964 | 2204 | 4.6 | 0.476 |
| RBC10-IP | 23.4 | 1 | 30329 | 30540 | 3.7 | 0.033 |
| RBC10-PO | 2.3 | 1 | 4752 | 5225 | 1.9 | 0.191 |

Example 6

In Vitro Evaluation of Human Cancer Cell Growth Inhibition

Figure 6:
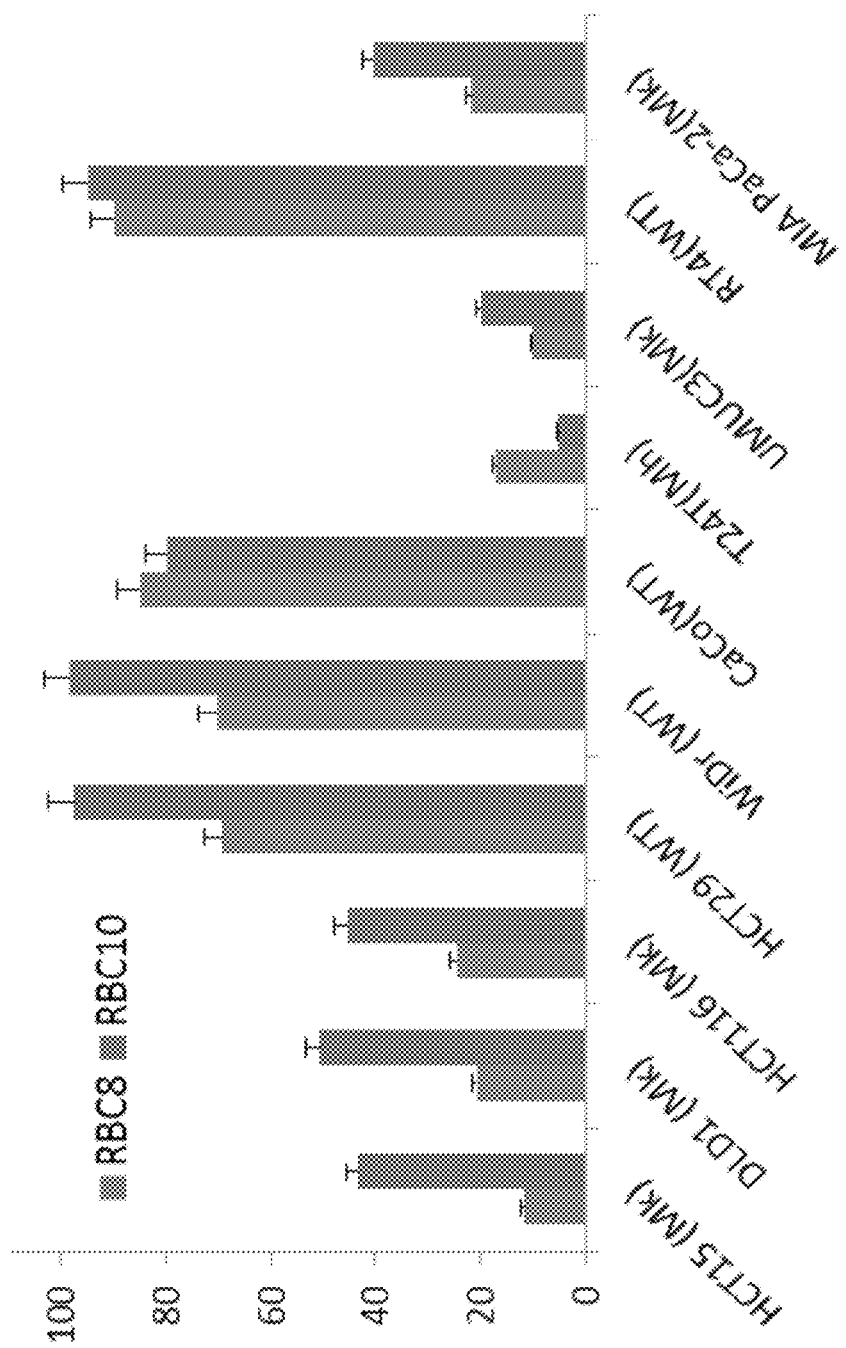
FIG. 6 shows the in vitro cancer cell growth inhibitory effect of a 1 µM concentration of Ral-GTPase inhibiting compounds of the invention.

The growth inhibition properties of certain Ral-GTPase inhibiting compounds of the invention were evaluated in vitro. Human cancer cell lines with different histologies and K-Ras mutant status were used to examine the in vitro growth inhibitory effect of a 1 µM concentration of two Ral-GTPase inhibiting compounds of the invention (FIG. 6).

Example 7

In Vitro Dose Response Curves in Human Cancer Cells

Figure 7A:
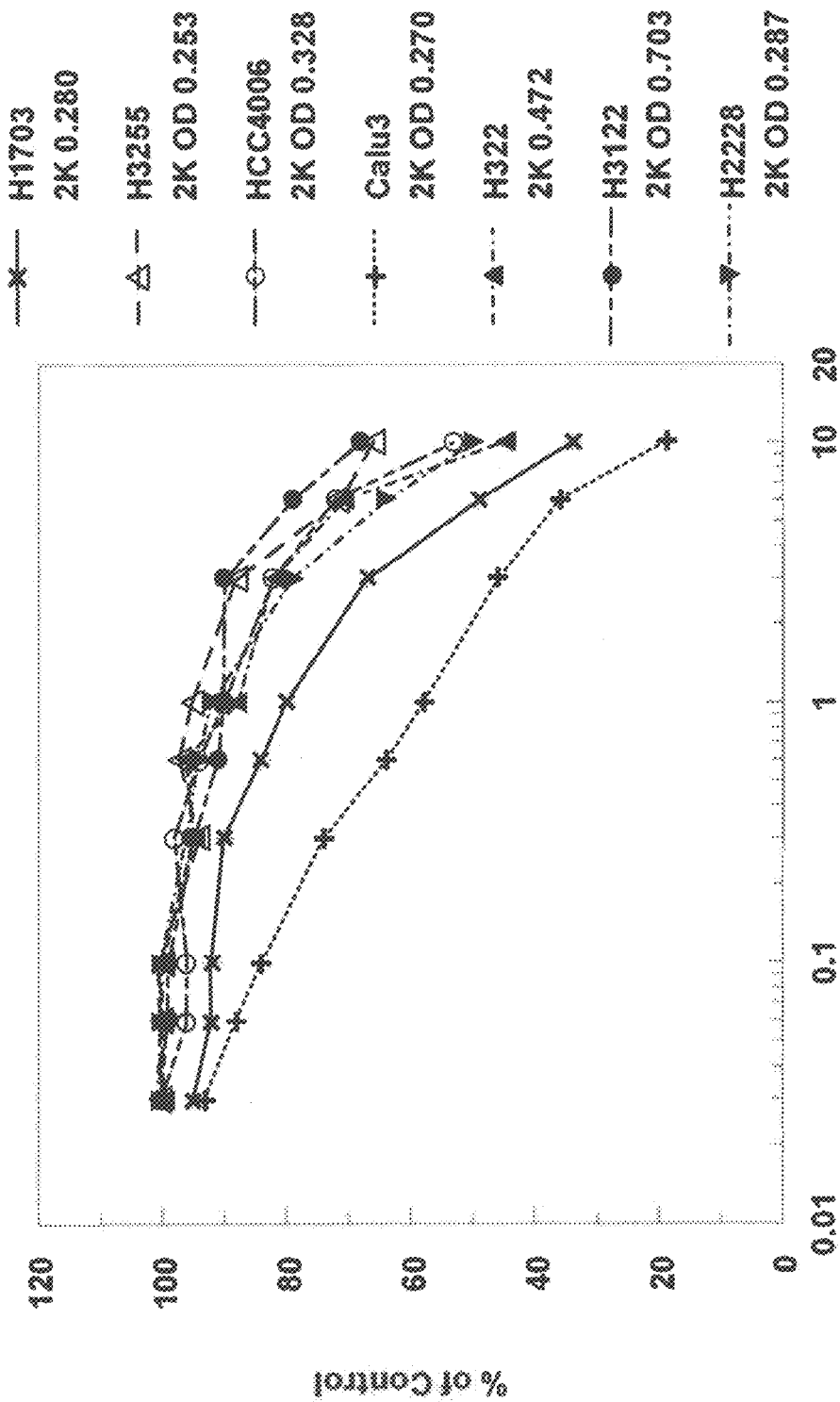
FIG. 7A shows the in vitro growth inhibitory effect of Ral-GTPase inhibiting compounds of the invention over a concentration range in KRAS wildtype cancer cell lines.
Figure 7B:
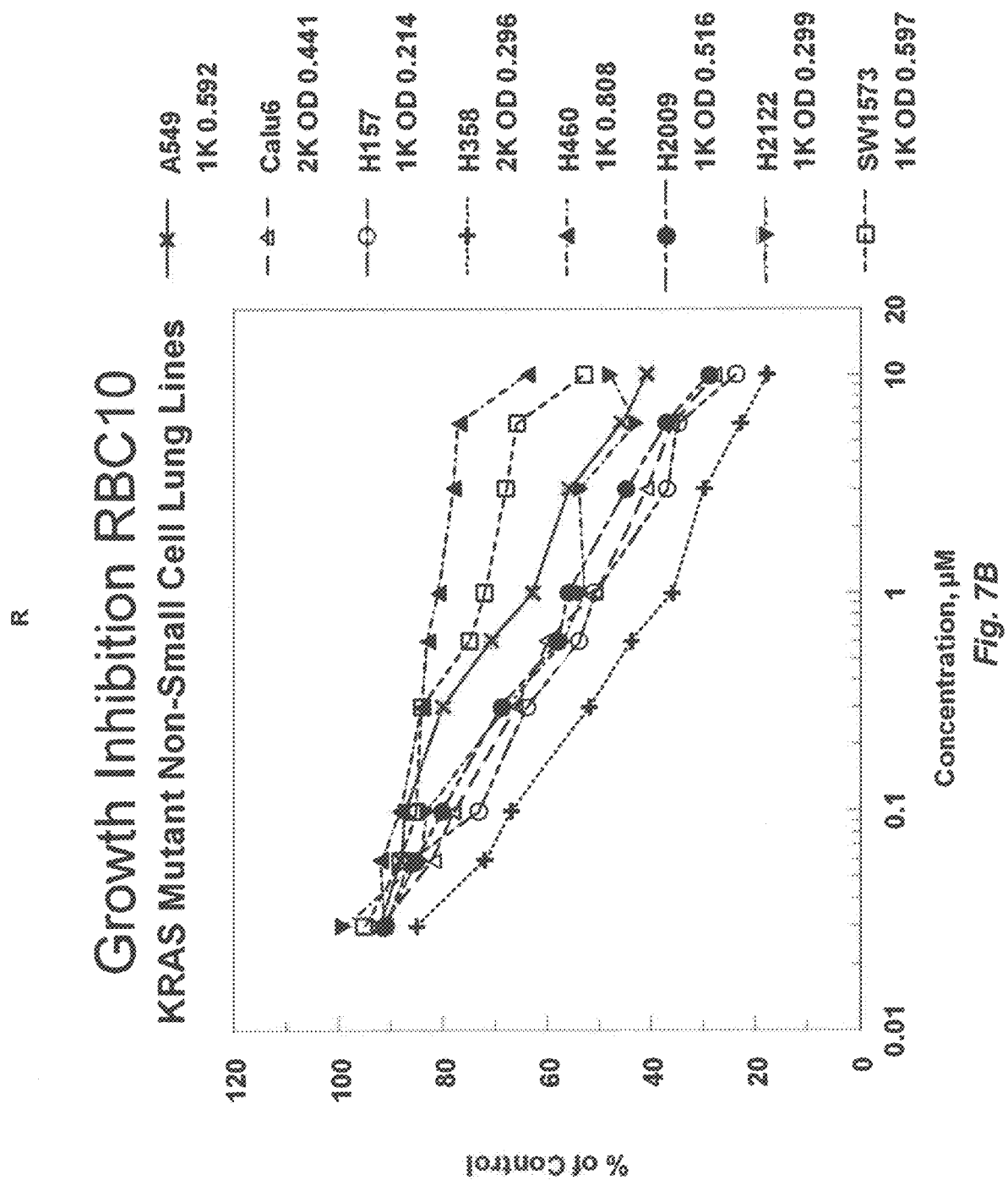
FIG. 7B shows the in vitro growth inhibitory effect of Ral-GTPase inhibiting compounds of the invention over a concentration range in KRAS mutant cancer cell lines.

Human lung cancer cell lines with different K-Ras mutant status were used to examine the in vitro growth inhibitory effect over a micromolar concentration range of Ral-GTPase inhibiting compounds of the invention (FIGS. 7A and 7B).

Example 8

Cell Uptake Experiments

Figure 8:
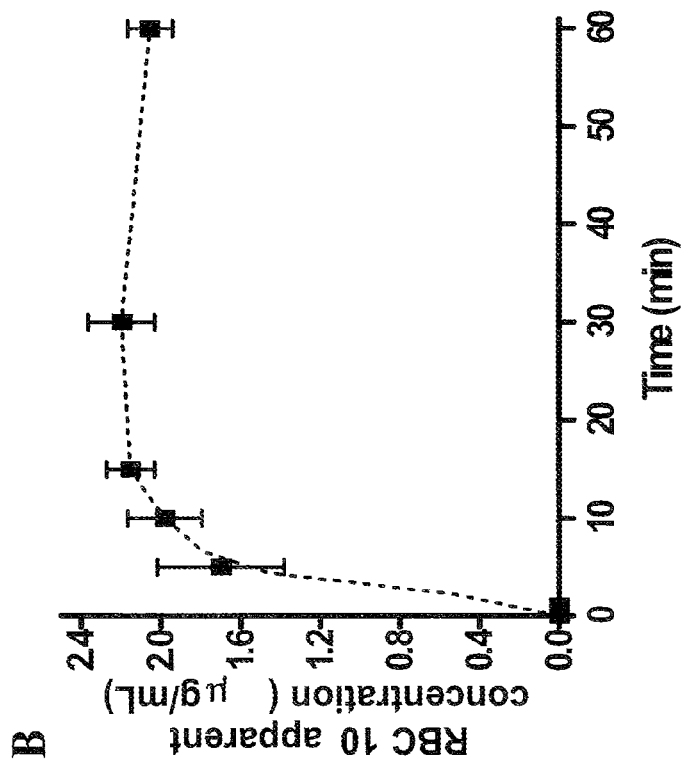
FIG. 8 shows the in vitro cellular uptake of Ral-GTPase inhibiting compounds of the invention in H2122 cells.
Figure 8:
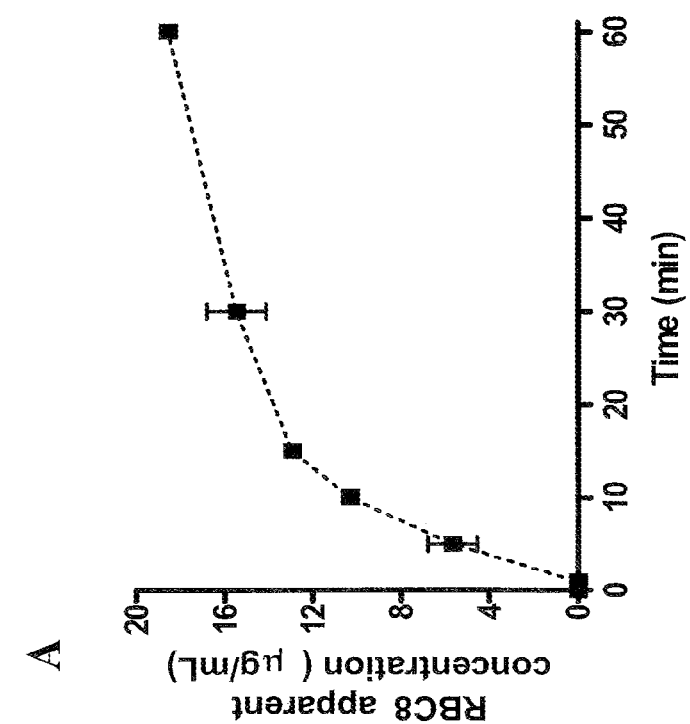

H2122 cells were used to measure in vitro cell uptake of RBC8 and RBC10 over 1 hour. RBC8 and RBC10 compounds were individually dosed (10 µM) in triplicate, and the cells were isolated at different time points (1, 5, 15, 30 and 60 min). RBC8 and RBC10 concentrations were determined using LC/MS-MS methods. FIG. 8A shows the cellular uptake of RBC8 over 1 hour. FIG. 8B shows the cellular uptake of RBC10 over 1 hour. n=3+/−SD at each time point.

Example 9

In Vivo Pharmacokinetic Data

Figure 9:
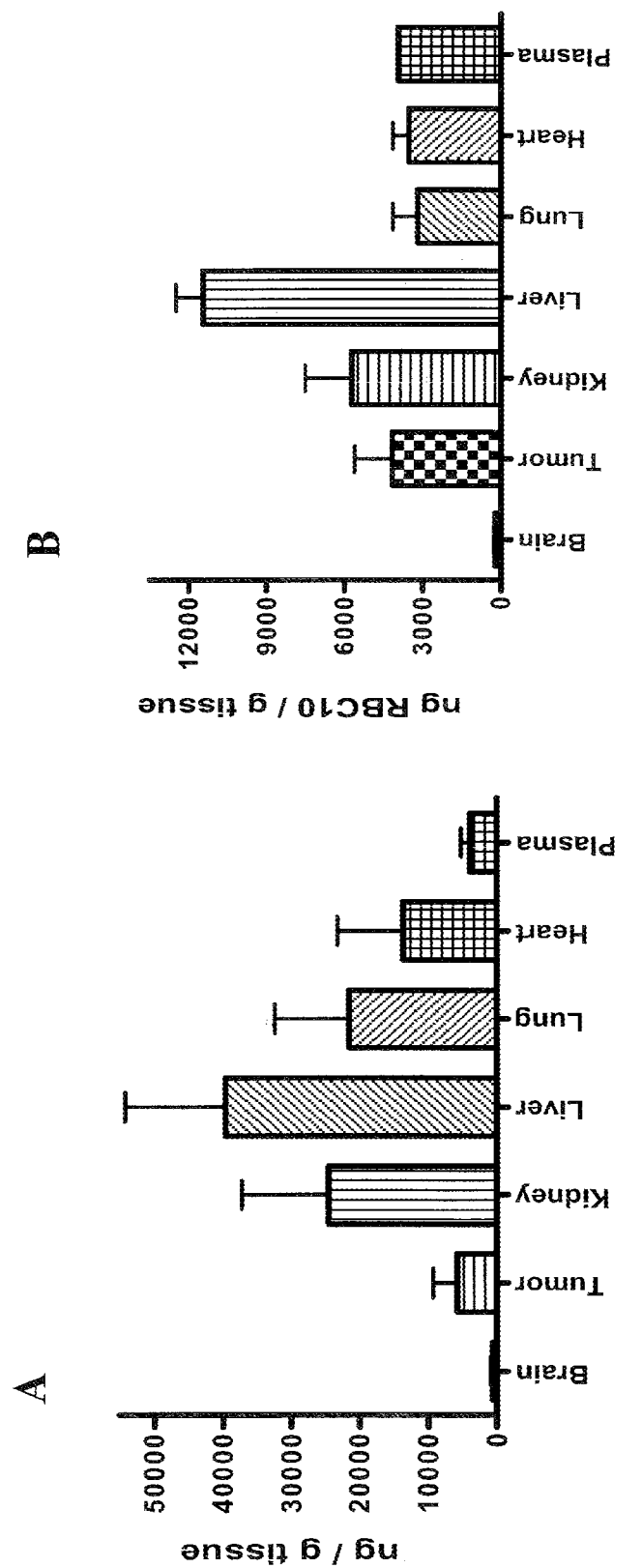
FIG. 9 shows the tissue concentrations of Ral-GTPase inhibiting compounds of the invention in H2122 xenografts following IP administration.

H2122 cells were used to generate xenografts in mice. RBC8 and RBC10 were delivered at 50 mg/kg IP and tissue samples were collected at 1 and 2 hours post inoculation. RBC8 and RBC10 concentrations were determined using LC/MS-MS methods. FIG. 9A shows the tissue concentrations of RBC8 at Tmax. FIG. 9B shows the tissue concentrations of RBC10 at Tmax. (Plasma data is ng/ml. To appropriately compare to tissue data, plasma concentration must be multiplied by plasma volume.)

Example 10

In Vivo Efficacy Data

Figure 10:
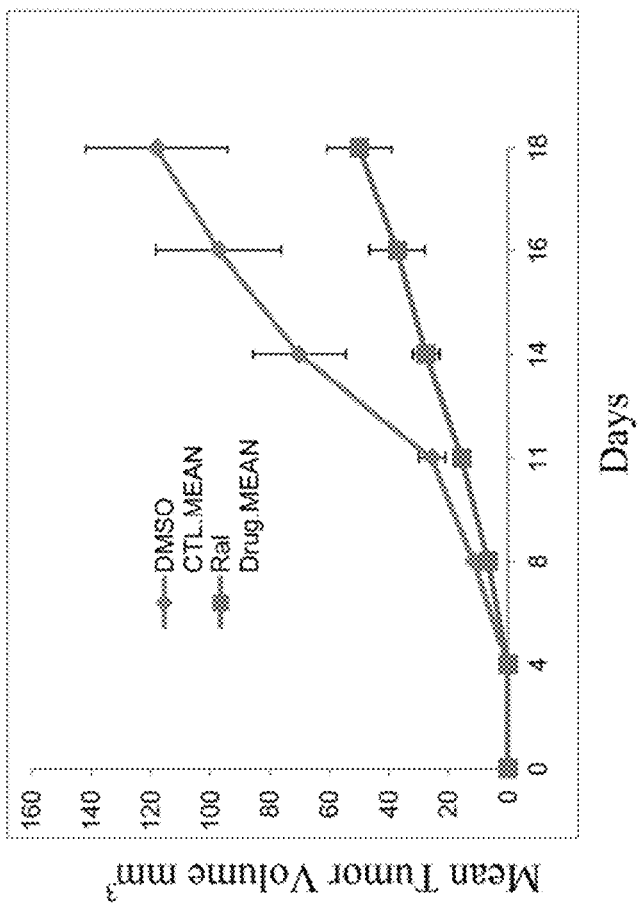
FIG. 10 shows H2122 mouse xenograft tumor volume following daily administration of Ral-GTPase inhibiting compounds of the invention.
Figure 10:
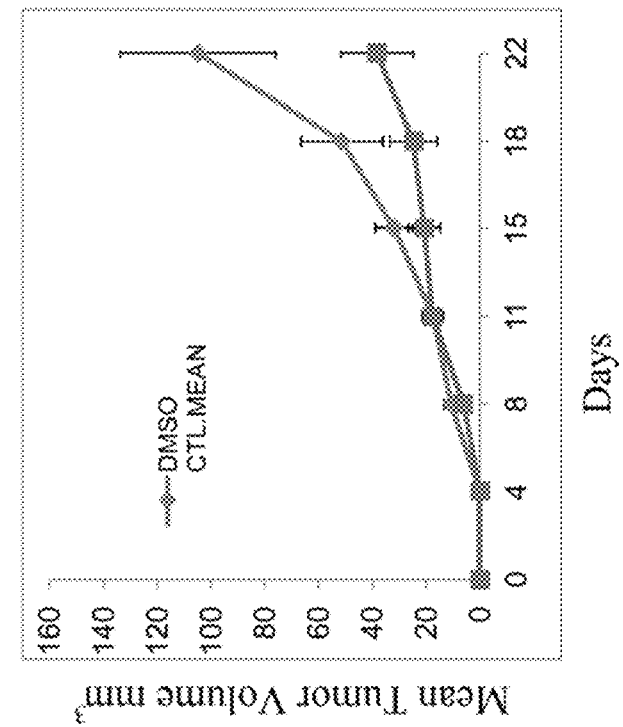

Ten nude mice per group were each given one inoculation of 200,000 H2122 human lung cancer cells. Drug treatment started on the day of the inoculation at 50 mg/kg/day, delivered IP daily, except on weekends. FIG. 10A shows the tumor volume following RBC8 treatment over 22 days. FIG. 10B shows the tumor volume following RBC10 treatment over 18 days.

Example 11

In Vivo Ral Inhibition Data (siRNA)

Figure 11:
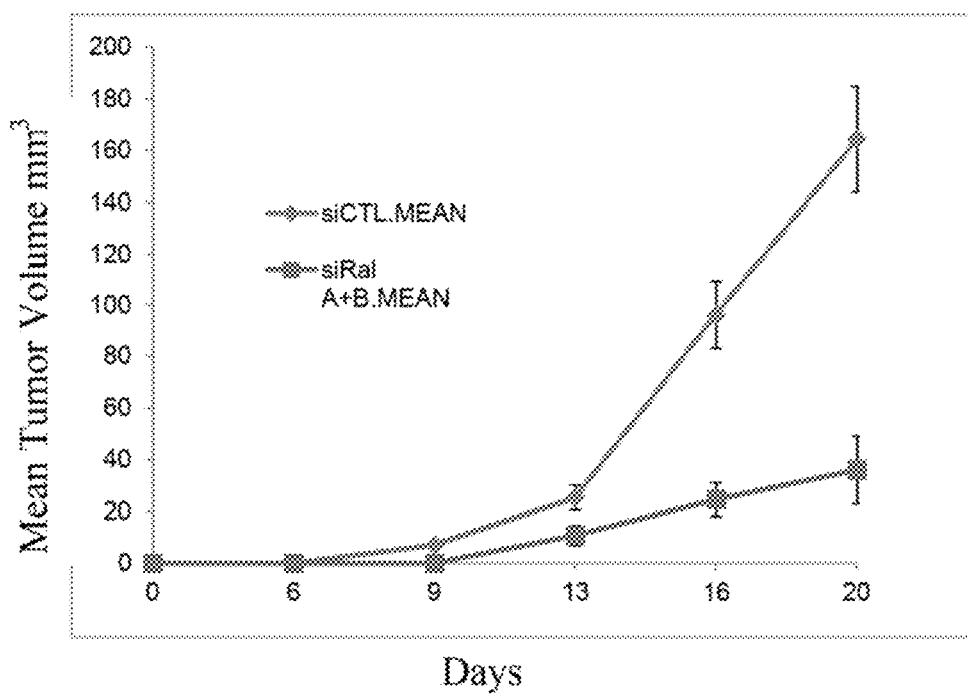
FIG. 11 shows H2122 mouse xenograft tumor volume following treatment of the cells with RalA- and RalB-depleting siRNA.

Ten nude mice per group were each given one inoculation of 200,000 H2122 human lung cancer cells 24 hours after the cells were treated with siRNA depleting both RalA and RalB. FIG. 11 shows tumor volume of treated and untreated cells over 20 days.

Example 12

In Vivo Ral Inhibition Data (Compounds of the Invention)

Figure 12:
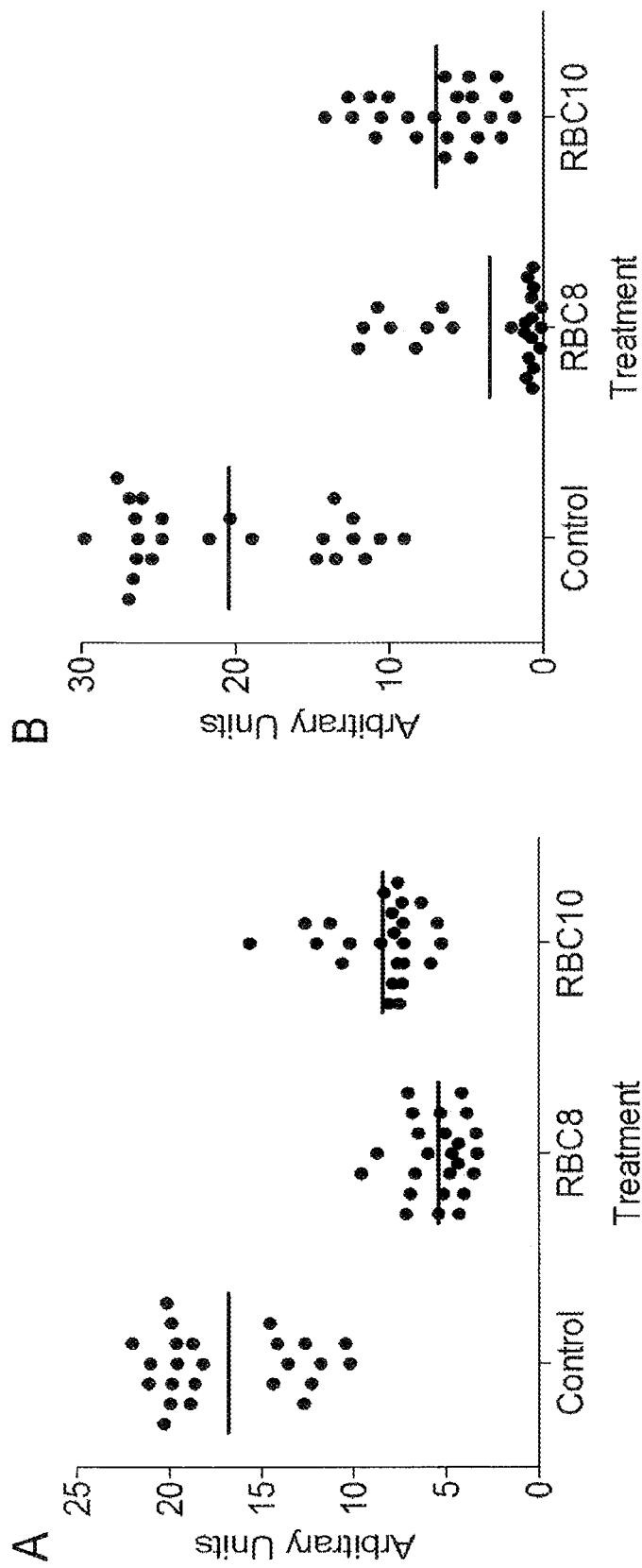
FIG. 12 shows inhibition of RalA and RalB GTPase activity in vivo in H2122 mouse xenografts by compounds of the invention.

Human lung cancer cell line H2122 was inoculated subcutaneously into female nude mice and allowed to grow until tumors reached an average size of 200 mm$^3$. Mice were given a single IP dose of 50 mg/Kg RBC8, RBC10, or DMSO control. Xenograft tumors were collected 2 h (RBC10) or 3 h (RBC8) after injection. RalA and RalB activity in tumors were measured by pull-down assay using RalBP1 agarose beads and normalized to total protein. FIG. 12A shows inhibition of RalA in tumors by RBC8 and RBC10. FIG. 12B shows inhibition of RalB in tumors by RBC8 and RBC10.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A compound selected from the group consisting of:
   3-(3,4-dimethoxyphenyl)-1-methyl-1H-pyrazol-5(4H)-one
   3-(3,4-dimethoxyphenyl)-1-phenyl-1H-pyrazol-5(4H)-one
   3-(4-methoxyphenyl)-1-methyl-1H-pyrazol-5(4H)-one
   6-amino-3-methyl-1,4-diphenyl-1,4-dihydropyrano[2,3-c]pyrazole-5-carbonitrile
   6-amino-4-(4-fluorophenyl)-3-methyl-1-phenyl-1,4-dihydropyrano[2,3-c]pyrazole-5-carbonitrile
   6-amino-1,3-dimethyl-4-phenyl-1,4-dihydropyrano[2,3-c]pyrazole-5-carbonitrile
   6-amino-1-methyl-3,4-diphenyl-1,4-dihydropyrano[2,3-c]pyrazole-5-carbonitrile
   6-amino-1,3,4-triphenyl-1,4-dihydropyrano[2,3-c]pyrazole-5-carbonitrile
   6-amino-3-(4-methoxyphenyl)-1,4-diphenyl-1,4-dihydropyrano[2,3-c]pyrazole-5-carbonitrile
   6-amino-3-(4-methoxyphenyl)-1-methyl-4-phenyl-1,4-dihydropyrano[2,3-c]pyrazole-5-carbonitrile
   6-amino-3-(3,4-dimethoxyphenyl)-1-methyl-4-phenyl-1,4-dihydropyrano[2,3-c]pyrazole-5-carbonitrile
   6-amino-4-(4-fluorophenyl)-1,3-dimethyl-1,4-dihydropyrano[2,3-c]pyrazole-5-carbonitrile
   6-amino-4-(4-fluorophenyl)-1-methyl-3-phenyl-1,4-dihydropyrano[2,3-c]pyrazole-5-carbonitrile
   6-amino-4-(4-fluorophenyl)-1,3-diphenyl-1,4-dihydropyrano[2,3-c]pyrazole-5-carbonitrile
   6-amino-3-(3,4-dimethoxyphenyl)-4-(4-fluorophenyl)-1-methyl-1,4-dihydropyrano[2,3-c]pyrazole-5-carbonitrile
   6-amino-4-(4-fluorophenyl)-3-(4-methoxyphenyl)-1-phenyl-1,4-dihydropyrano[2,3-c]pyrazole-5-carbonitrile
   6-amino-3-(3,4-dimethoxyphenyl)-4-(4-fluorophenyl)-1-phenyl-1,4-dihydropyrano[2,3-c]pyrazole-5-carbonitrile
   6-amino-4-(4-fluorophenyl)-3-(4-methoxyphenyl)-1-methyl-1,4-dihydropyrano[2,3-c]pyrazole-5-carbonitrile
   6-amino-4-(4-methoxyphenyl)-3-methyl-1-phenyl-1,4-dihydropyrano[2,3-c]pyrazole-5-carbonitrile
   6-amino-4-(4-methoxyphenyl)-1,3-dimethyl-1,4-dihydropyrano[2,3-c]pyrazole-5-carbonitrile
   6-amino-4-(4-methoxyphenyl)-1-methyl-3-phenyl-1,4-dihydropyrano[2,3-c]pyrazole-5-carbonitrile
   6-amino-4-(4-methoxyphenyl)-1,3-diphenyl-1,4-dihydropyrano[2,3-c]pyrazole-5-carbonitrile
   6-amino-3,4-bis(4-methoxyphenyl)-1-phenyl-1,4-dihydropyrano[2,3-c]pyrazole-5-carbonitrile
   6-amino-3,4-bis(4-methoxyphenyl)-1-methyl-1,4-dihydropyrano[2,3-c]pyrazole-5-carbonitrile and salts thereof.

2. A pharmaceutical composition comprising at least one compound selected from the group consisting of:
   3-(3,4-dimethoxyphenyl)-1-methyl-1H-pyrazol-5(4H)-one
   3-(3,4-dimethoxyphenyl)-1-phenyl-1H-pyrazol-5(4H)-one
   3-(4-methoxyphenyl)-1-methyl-1H-pyrazol-5(4H)-one
   6-amino-3-methyl-1,4-diphenyl-1,4-dihydropyrano[2,3-c]pyrazole-5-carbonitrile
   6-amino-4-(4-fluorophenyl)-3-methyl-1-phenyl-1,4-dihydropyrano[2,3-c]pyrazole-5-carbonitrile
   6-amino-1,3-dimethyl-4-phenyl-1,4-dihydropyrano[2,3-c]pyrazole-5-carbonitrile
   6-amino-1-methyl-3,4-diphenyl-1,4-dihydropyrano[2,3-c]pyrazole-5-carbonitrile
   6-amino-1,3,4-triphenyl-1,4-dihydropyrano[2,3-c]pyrazole-5-carbonitrile
   6-amino-3-(4-methoxyphenyl)-1,4-diphenyl-1,4-dihydropyrano[2,3-c]pyrazole-5-carbonitrile
   6-amino-3-(4-methoxyphenyl)-1-methyl-4-phenyl-1,4-dihydropyrano[2,3-c]pyrazole-5-carbonitrile
   6-amino-3-(3,4-dimethoxyphenyl)-1-methyl-4-phenyl-1,4-dihydropyrano[2,3-c]pyrazole-5-carbonitrile
   6-amino-4-(4-fluorophenyl)-1,3-dimethyl-1,4-dihydropyrano[2,3-c]pyrazole-5-carbonitrile
   6-amino-4-(4-fluorophenyl)-1-methyl-3-phenyl-1,4-dihydropyrano[2,3-c]pyrazole-5-carbonitrile
   6-amino-4-(4-fluorophenyl)-1,3-diphenyl-1,4-dihydropyrano[2,3-c]pyrazole-5-carbonitrile
   6-amino-3-(3,4-dimethoxyphenyl)-4-(4-fluorophenyl)-1-methyl-1,4-dihydropyrano[2,3-c]pyrazole-5-carbonitrile
   6-amino-4-(4-fluorophenyl)-3-(4-methoxyphenyl)-1-phenyl-1,4-dihydropyrano[2,3-c]pyrazole-5-carbonitrile
   6-amino-3-(3,4-dimethoxyphenyl)-4-(4-fluorophenyl)-1-phenyl-1,4-dihydropyrano[2,3-c]pyrazole-5-carbonitrile
   6-amino-4-(4-fluorophenyl)-3-(4-methoxyphenyl)-1-methyl-1,4-dihydropyrano[2,3-c]pyrazole-5-carbonitrile
   6-amino-4-(4-methoxyphenyl)-3-methyl-1-phenyl-1,4-dihydropyrano[2,3-c]pyrazole-5-carbonitrile 6-amino-4-(4-methoxyphenyl)-1,3-dimethyl-1,4-dihydropyrano[2,3-c]pyrazole-5-carbonitrile 6-amino-4-(4-methoxyphenyl)-1-methyl-3-phenyl-1,4-dihydropyrano[2,3-c]pyrazole-5-carbonitrile 6-amino-4-(4-methoxyphenyl)-1,3-diphenyl-1,4-dihydropyrano[2,3-c]pyrazole-5-carbonitrile 6-amino-3,4-bis(4-methoxyphenyl)-1-phenyl-1,4-dihydropyrano[2,3-c]pyrazole-5-carbonitrile 6-amino-3,4-bis(4-methoxyphenyl)-1-methyl-1,4-dihydropyrano[2,3-c]pyrazole-5-carbonitrile and salts thereof, and at least one pharmaceutical excipient.

3. A pharmaceutical composition comprising at least one compound selected from the group consisting of:

1-benzyl-3-phenyl-1H-pyrazol-5(4H)-one 3-(3,4-dimethoxyphenyl)-1-methyl-1H-pyrazol-5 (4H)-one 3-(3,4-dimethoxyphenyl)-1-phenyl-1H-pyrazol-5 (4H)-one 3-(4-methoxyphenyl)-1-phenyl-1H-pyrazol-5 (4H)-one 3-(4-methoxyphenyl)-1-methyl-1H-pyrazol-5 (4H)-one 6-amino-3-methyl-1,4-diphenyl-1,4-dihydropyrano[2,3-c]pyrazole-5-carbonitrile 6-amino-4-(4-fluorophenyl)-3-methyl-1-phenyl-1,4-dihydropyrano[2,3-c]pyrazole-5-carbonitrile 6-amino-1,3-dimethyl-4-phenyl-1,4-dihydropyrano[2,3-c]pyrazole-5-carbonitrile 6-amino-1-methyl-3,4-diphenyl-1,4-dihydropyrano[2,3-c]pyrazole-5-carbonitrile 6-amino-1,3,4-triphenyl-1,4-dihydropyrano[2,3-c]pyrazole-5-carbonitrile 6-amino-3-(4-methoxyphenyl)-1,4-diphenyl-1,4-dihydropyrano[2,3-c]pyrazole-5-carbonitrile 6-amino-3-(4-methoxyphenyl)-1-methyl-4-phenyl-1,4-dihydropyrano[2,3-c]pyrazole-5-carbonitrile 6-amino-3-(3,4-dimethoxyphenyl)-1-methyl-4-phenyl-1,4-dihydropyrano[2,3-c]pyrazole-5-carbonitrile 6-amino-4-(4-fluorophenyl)-1,3-dimethyl-1,4-dihydropyrano[2,3-c]pyrazole-5-carbonitrile 6-amino-4-(4-fluorophenyl)-1-methyl-3-phenyl-1,4-dihydropyrano[2,3-c]pyrazole-5-carbonitrile 6-amino-4-(4-fluorophenyl)-1,3-diphenyl-1,4-dihydropyrano[2,3-c]pyrazole-5-carbonitrile 6-amino-3-(3,4-dimethoxyphenyl)-4-(4-fluorophenyl)-1-methyl-1,4-dihydropyrano[2,3-c]pyrazole-5-carbonitrile 6-amino-4-(4-fluorophenyl)-3-(4-methoxyphenyl)-1-phenyl-1,4-dihydropyrano[2,3-c]pyrazole-5-carbonitrile 6-amino-3-(3,4-dimethoxyphenyl)-4-(4-fluorophenyl)-1-phenyl-1,4-dihydropyrano[2,3-c]pyrazole-5-carbonitrile 6-amino-4-(4-fluorophenyl)-3-(4-methoxyphenyl)-1-methyl-1,4-dihydropyrano[2,3-c]pyrazole-5-carbonitrile 6-amino-4-(4-methoxyphenyl)-3-methyl-1-phenyl-1,4-dihydropyrano[2,3-c]pyrazole-5-carbonitrile 6-amino-4-(4-methoxyphenyl)-1,3-dimethyl-1,4-dihydropyrano[2,3-c]pyrazole-5-carbonitrile 6-amino-4-(4-methoxyphenyl)-1-methyl-3-phenyl-1,4-dihydropyrano[2,3-c]pyrazole-5-carbonitrile 6-amino-4-(4-methoxyphenyl)-1,3-diphenyl-1,4-dihydropyrano[2,3-c]pyrazole-5-carbonitrile 6-amino-3,4-bis(4-methoxyphenyl)-1-phenyl-1,4-dihydropyrano[2,3-c]pyrazole-5-carbonitrile 6-amino-3,4-bis(4-methoxyphenyl)-1-methyl-1,4-dihydropyrano[2,3-c]pyrazole-5-carbonitrile and salts thereof, and at least one pharmaceutical excipient, wherein the pharmaceutical composition is an oral dosage form, a parenteral dosage form, or an inhalation dosage form.

4. The pharmaceutical composition of claim 3, wherein the oral dosage form is at least one dosage form selected from the group consisting of: capsules, tablets, pills, dragees, powders, and granules.

5. The pharmaceutical composition of claim 3, wherein the parenteral dosage form is at least one dosage form selected from the group consisting of: liquid solutions, liquid suspensions, and solutions or suspensions of powders, granules, or tablets.

6. The pharmaceutical composition of claim 3, wherein the inhalation dosage form is at least one dosage form selected from the group consisting of: aerosol sprays, liquid sprays, drops, and powders.

7. The pharmaceutical composition of claim 3, wherein the pharmaceutical excipient is at least one selected from the group consisting of: sodium citrate, dicalcium phosphate, fillers, extenders, binders, humectants, disintegrating agents, solution retarding agents, absorption accelerators, wetting agents, absorbents, lubricants, coloring agents, propellants, volatile unsubstituted hydrocarbons, and combinations thereof.

8. The pharmaceutical composition of claim 7, wherein the pharmaceutical excipient is at least one selected from the group consisting of: starches, lactose, sucrose, glucose, mannitol, silicic acid, carboxymethylcellulose, alginates, gelatin, polyvinyl pyrrolidone, sucrose, acacia, glycerol, agar-agar, calcium carbonate, potato or tapioca starch, alginic acid, silicates, silicic acid, aluminum hydroxide, sodium carbonate, paraffin, quaternary ammonium compounds, cetyl alcohol, glycerol monosterate, kaolin, bentonite clay, talc, polyamide powder, calcium stearate, magnesium stearate, solid polyethylene glycols, sodium lauryl sulfate, chlorofluorohydrocarbons, butane, propane, and mixtures thereof.

9. The pharmaceutical composition of claim 3, further comprising at least one additive selected from the group consisting of: solubilizing agents, emulsifiers, wetting agents, dispersing agents, suspending agents, sweetening agents, flavoring agents, coloring agents, preservative agents, and mixtures thereof.

* * * * *